(12) United States Patent
Shelton, IV et al.

(10) Patent No.: US 9,968,354 B2
(45) Date of Patent: *May 15, 2018

(54) SURGICAL STAPLES AND METHODS FOR MAKING THE SAME

(71) Applicant: Ethicon LLC, Guaynabo, PR (US)

(72) Inventors: Frederick E. Shelton, IV, Hillsboro, OH (US); Chester O. Baxter, III, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 462 days.

This patent is subject to a terminal disclaimer.

(21) Appl. No.: 14/138,481

(22) Filed: Dec. 23, 2013

(65) Prior Publication Data

US 2015/0173750 A1    Jun. 25, 2015

(51) Int. Cl.
*A61B 17/08* (2006.01)
*A61B 17/064* (2006.01)
*A61B 17/072* (2006.01)
*A61B 17/068* (2006.01)
*A61B 17/00* (2006.01)

(52) U.S. Cl.
CPC ........ *A61B 17/0644* (2013.01); *A61B 17/068* (2013.01); *A61B 17/07207* (2013.01); *A61B 17/064* (2013.01); *A61B 17/0682* (2013.01); *A61B 17/072* (2013.01); *A61B 2017/00398* (2013.01); *A61B 2017/00526* (2013.01); *A61B 2017/00734* (2013.01); *A61B 2017/07228* (2013.01); *A61B 2017/07271* (2013.01); *A61B 2017/07278* (2013.01); *A61B 2017/07285* (2013.01); *Y10T 29/49995* (2015.01)

(58) Field of Classification Search
CPC .............. A61B 17/0644; A61B 17/068; A61B 17/07207; A61B 17/064; A61B 17/072; A61B 17/0682; A61B 2017/00398; A61B 2017/07285; A61B 2017/07271; A61B 2017/00734; A61B 2017/07228
See application file for complete search history.

(56) References Cited

U.S. PATENT DOCUMENTS

| 4,060,089 | A | 11/1977 | Noiles |
| 4,434,796 | A | 3/1984 | Karapetian et al. |
| 4,505,273 | A | 3/1985 | Braun et al. |
| 4,531,522 | A | 7/1985 | Bedi et al. |
| 4,532,927 | A | 8/1985 | Miksza, Jr. |
| D286,180 | S | 10/1986 | Korthoff |
| D286,442 | S | 10/1986 | Korthoff et al. |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

U.S. Appl. No. 14/138,554, filed Dec. 23, 2013.

(Continued)

*Primary Examiner* — Richard Louis

(57) ABSTRACT

A surgical staple and staple cartridge for removably storing the surgical staple. The staple can be formed and/or stamped from a sheet of material. The staple can include a base and staple legs extending from the base. The base can be non-linear and/or laterally contoured intermediate the staple legs.

13 Claims, 55 Drawing Sheets

(56) References Cited

U.S. PATENT DOCUMENTS

| | | | |
|---|---|---|---|
| 4,655,222 A | 4/1987 | Florez et al. |
| 4,890,613 A | 1/1990 | Golden et al. |
| 4,932,960 A | 6/1990 | Green et al. |
| 5,042,707 A | 8/1991 | Taheri |
| 5,071,430 A | 12/1991 | de Salis et al. |
| D327,323 S | 6/1992 | Hunt |
| 5,122,156 A | 6/1992 | Granger et al. |
| 5,139,513 A | 8/1992 | Segato |
| 5,156,614 A | 10/1992 | Green et al. |
| 5,158,567 A | 10/1992 | Green |
| 5,222,975 A | 6/1993 | Crainich |
| D338,729 S | 8/1993 | Sprecklemeier et al. |
| 5,236,440 A | 8/1993 | Hlavacek |
| 5,258,009 A | 11/1993 | Conners |
| 5,258,012 A | 11/1993 | Luscombe et al. |
| 5,282,829 A | 2/1994 | Hermes |
| 5,304,204 A | 4/1994 | Bregen |
| D347,474 S | 5/1994 | Olson |
| D348,930 S | 7/1994 | Olson |
| 5,342,395 A | 8/1994 | Jarrett et al. |
| 5,342,396 A | 8/1994 | Cook |
| 5,350,400 A | 9/1994 | Esposito et al. |
| 5,352,229 A | 10/1994 | Goble et al. |
| 5,352,238 A | 10/1994 | Green et al. |
| 5,358,510 A | 10/1994 | Luscombe et al. |
| 5,366,479 A | 11/1994 | McGarry et al. |
| D357,981 S | 5/1995 | Green et al. |
| 5,425,745 A | 6/1995 | Green et al. |
| 5,439,479 A | 8/1995 | Schichman et al. |
| 5,478,354 A | 12/1995 | Tovey et al. |
| 5,549,628 A | 8/1996 | Cooper et al. |
| 5,554,169 A | 9/1996 | Green et al. |
| 5,571,285 A | 11/1996 | Chow et al. |
| D381,077 S | 7/1997 | Hunt |
| 5,667,527 A | 9/1997 | Cook |
| 5,695,524 A | 12/1997 | Kelley et al. |
| 5,704,534 A | 1/1998 | Huitema et al. |
| 5,725,554 A | 3/1998 | Simon et al. |
| 5,730,758 A | 3/1998 | Allgeyer |
| 5,919,198 A * | 7/1999 | Graves, Jr. ........ A61B 17/07207 227/176.1 |
| 5,941,890 A | 8/1999 | Voegele et al. |
| D416,089 S | 11/1999 | Barton et al. |
| 6,015,417 A | 1/2000 | Reynolds, Jr. |
| 6,033,427 A | 3/2000 | Lee |
| 6,083,242 A | 7/2000 | Cook |
| 6,099,551 A | 8/2000 | Gabbay |
| 6,171,330 B1 | 1/2001 | Benchetrit |
| 6,197,042 B1 | 3/2001 | Ginn et al. |
| 6,338,737 B1 | 1/2002 | Toledano |
| 6,387,113 B1 | 5/2002 | Hawkins et al. |
| 6,387,114 B2 | 5/2002 | Adams |
| RE37,814 E | 8/2002 | Allgeyer |
| 6,443,973 B1 | 9/2002 | Whitman |
| 6,494,896 B1 | 12/2002 | D'Alessio et al. |
| 6,517,565 B1 | 2/2003 | Whitman et al. |
| 6,517,566 B1 | 2/2003 | Hovland et al. |
| 6,616,686 B2 | 9/2003 | Coleman et al. |
| 6,629,988 B2 | 10/2003 | Weadock |
| 6,638,297 B1 | 10/2003 | Huitema |
| 6,685,727 B2 | 2/2004 | Fisher et al. |
| 6,716,233 B1 | 4/2004 | Whitman |
| 6,767,356 B2 | 7/2004 | Kanner et al. |
| D502,994 S | 3/2005 | Blake, III |
| 6,921,412 B1 | 7/2005 | Black et al. |
| D509,297 S | 9/2005 | Wells |
| D509,589 S | 9/2005 | Wells |
| 7,056,330 B2 | 6/2006 | Gayton |
| 7,077,856 B2 | 7/2006 | Whitman |
| 7,112,214 B2 | 9/2006 | Peterson et al. |
| 7,156,863 B2 | 1/2007 | Sonnenschein et al. |
| 7,220,272 B2 | 5/2007 | Weadock |
| 7,238,195 B2 | 7/2007 | Viola |
| 7,328,828 B2 | 2/2008 | Ortiz et al. |
| 7,341,591 B2 | 3/2008 | Grinberg |
| 7,354,447 B2 | 4/2008 | Shelton, IV et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,682 B2 | 11/2008 | Viola |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,506,791 B2 | 3/2009 | Omaits et al. |
| 7,510,107 B2 | 3/2009 | Timm et al. |
| 7,517,356 B2 | 4/2009 | Heinrich |
| 7,549,564 B2 | 6/2009 | Boudreaux |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,644,848 B2 | 1/2010 | Swayze et al. |
| 7,651,498 B2 | 1/2010 | Shifrin et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,744,628 B2 | 6/2010 | Viola |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,426 B2 | 11/2010 | Racenet et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,902 B2 | 3/2011 | Huitema et al. |
| 7,909,220 B2 | 3/2011 | Viola |

(56) References Cited

U.S. PATENT DOCUMENTS

| | | |
|---|---|---|
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,743 B2 | 4/2011 | Heinrich et al. |
| 7,934,630 B2 | 5/2011 | Shelton, IV et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,967,839 B2 | 6/2011 | Flock et al. |
| 7,980,443 B2 | 7/2011 | Scheib et al. |
| 8,002,795 B2 | 8/2011 | Beetel |
| 8,016,858 B2 | 9/2011 | Whitman |
| 8,020,743 B2 | 9/2011 | Shelton, IV |
| 8,034,077 B2 | 10/2011 | Smith et al. |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,097,017 B2 | 1/2012 | Viola |
| 8,113,410 B2 | 2/2012 | Hall et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,781 B2 | 6/2012 | Baxter, III et al. |
| 8,220,688 B2 | 6/2012 | Laurent et al. |
| 8,210,411 B2 | 7/2012 | Yates et al. |
| 8,215,531 B2 | 7/2012 | Shelton, IV et al. |
| 8,220,690 B2 | 7/2012 | Hess et al. |
| 8,236,010 B2 | 8/2012 | Ortiz et al. |
| 8,267,300 B2 | 9/2012 | Boudreaux |
| 8,292,155 B2 | 10/2012 | Shelton, IV et al. |
| 8,292,888 B2 | 10/2012 | Whitman |
| 8,308,040 B2 | 11/2012 | Huang et al. |
| 8,317,070 B2 | 11/2012 | Hueil et al. |
| 8,317,790 B2 | 11/2012 | Bell et al. |
| 8,322,455 B2 | 12/2012 | Shelton, IV et al. |
| 8,322,589 B2 | 12/2012 | Boudreaux |
| 8,333,313 B2 | 12/2012 | Boudreaux et al. |
| 8,348,129 B2 | 1/2013 | Bedi et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,365,976 B2 | 2/2013 | Hess et al. |
| 8,371,491 B2 | 2/2013 | Huitema et al. |
| 8,393,514 B2 | 3/2013 | Shelton, IV et al. |
| 8,397,971 B2 | 3/2013 | Yates et al. |
| 8,408,439 B2 | 4/2013 | Huang et al. |
| 8,414,577 B2 | 4/2013 | Boudreaux et al. |
| 8,424,740 B2 | 4/2013 | Shelton, IV et al. |
| 8,444,036 B2 | 5/2013 | Shelton, IV |
| 8,453,907 B2 | 6/2013 | Laurent et al. |
| 8,453,908 B2 | 6/2013 | Bedi et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,923 B2 | 6/2013 | Shelton, IV |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,937 B2 | 11/2013 | Gresham |
| 8,584,919 B2 | 11/2013 | Hueil et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,736 B2 | 1/2014 | Yates et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,130 B2 | 3/2014 | Hess et al. |
| 8,672,207 B2 | 3/2014 | Shelton, IV et al. |
| 8,672,208 B2 | 3/2014 | Hess et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,728,119 B2 | 5/2014 | Cummins |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,808,294 B2 | 8/2014 | Fox et al. |
| 8,814,024 B2 | 8/2014 | Woodard, Jr. et al. |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,903 B2 | 9/2014 | Shelton, IV et al. |

(56) References Cited

U.S. PATENT DOCUMENTS

| | | |
|---|---|---|
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,911,471 B2 | 12/2014 | Spivey et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,016,542 B2 | 4/2015 | Shelton, IV et al. |
| 9,028,494 B2 | 5/2015 | Shelton, IV et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,515 B2 | 7/2015 | Hall et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,089,330 B2 | 7/2015 | Widenhouse et al. |
| 9,095,339 B2 | 8/2015 | Moore et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,883 B2 | 8/2015 | Aronhalt et al. |
| 9,113,884 B2 | 8/2015 | Shelton, IV et al. |
| 9,119,957 B2 | 9/2015 | Shelton, IV et al. |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,186,143 B2 | 11/2015 | Timm et al. |
| 2004/0006372 A1 | 1/2004 | Racenet et al. |
| 2004/0028502 A1* | 2/2004 | Cummins .......... A61B 17/0644 411/457 |
| 2004/0044364 A1 | 3/2004 | DeVries et al. |
| 2004/0073222 A1 | 4/2004 | Koseki |
| 2004/0093024 A1 | 5/2004 | Lousararian et al. |
| 2004/0167572 A1 | 8/2004 | Roth et al. |
| 2004/0254608 A1 | 12/2004 | Huitema et al. |
| 2004/0267310 A1 | 12/2004 | Racenet et al. |
| 2005/0010213 A1 | 1/2005 | Stad et al. |
| 2005/0049600 A1* | 3/2005 | Groiso .................. A61B 17/68 606/75 |
| 2005/0059997 A1 | 3/2005 | Bauman et al. |
| 2005/0187576 A1 | 8/2005 | Whitman et al. |
| 2005/0192628 A1 | 9/2005 | Viola |
| 2005/0216055 A1 | 9/2005 | Scirica et al. |
| 2005/0240222 A1 | 10/2005 | Shipp |
| 2005/0283188 A1 | 12/2005 | Loshakove et al. |
| 2006/0047307 A1 | 3/2006 | Ortiz et al. |
| 2006/0052825 A1 | 3/2006 | Ransick et al. |
| 2006/0085033 A1 | 4/2006 | Criscuolo et al. |
| 2006/0235469 A1 | 10/2006 | Viola |
| 2006/0241692 A1 | 10/2006 | McGuckin, Jr. et al. |
| 2007/0073341 A1 | 3/2007 | Smith |
| 2007/0093869 A1 | 4/2007 | Bloom et al. |
| 2007/0102472 A1 | 5/2007 | Shelton, IV |
| 2007/0106317 A1 | 5/2007 | Shelton, IV et al. |
| 2007/0118175 A1 | 5/2007 | Butler et al. |
| 2007/0170225 A1 | 7/2007 | Shelton, IV et al. |
| 2007/0175950 A1 | 8/2007 | Shelton, IV et al. |
| 2007/0175951 A1* | 8/2007 | Shelton, IV ..... A61B 17/07207 227/176.1 |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2007/0225562 A1 | 9/2007 | Spivey et al. |
| 2007/0239028 A1 | 10/2007 | Houser et al. |
| 2007/0260278 A1 | 11/2007 | Wheeler et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0065153 A1 | 3/2008 | Allard et al. |
| 2008/0078802 A1 | 4/2008 | Hess et al. |
| 2008/0082124 A1* | 4/2008 | Hess ................ A61B 17/064 606/219 |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0161808 A1* | 7/2008 | Fox .................... A61B 17/0642 606/75 |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0065552 A1* | 3/2009 | Knodel ................ A61B 17/072 227/180.1 |
| 2009/0090763 A1 | 4/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2010/0016888 A1 | 1/2010 | Calabrese et al. |
| 2010/0069942 A1 | 3/2010 | Shelton, IV |
| 2010/0133317 A1 | 6/2010 | Shelton, IV et al. |
| 2010/0193566 A1 | 8/2010 | Scheib et al. |
| 2010/0222901 A1 | 9/2010 | Swayze et al. |
| 2010/0305552 A1 | 12/2010 | Shelton, IV et al. |
| 2010/0331880 A1 | 12/2010 | Stopek |
| 2011/0006101 A1 | 1/2011 | Hall et al. |
| 2011/0024477 A1 | 2/2011 | Hall et al. |

(56) References Cited

U.S. PATENT DOCUMENTS

| | | |
|---|---|---|
| 2011/0024478 A1 | 2/2011 | Shelton, IV |
| 2011/0046666 A1 | 2/2011 | Sorrentino et al. |
| 2011/0060363 A1 | 3/2011 | Hess et al. |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0125176 A1 | 5/2011 | Yates et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0174861 A1 | 7/2011 | Shelton, IV et al. |
| 2011/0192882 A1 | 8/2011 | Hess et al. |
| 2011/0226837 A1* | 9/2011 | Baxter, III ......... A61B 17/0644 227/175.1 |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2012/0029272 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074198 A1 | 3/2012 | Huitema et al. |
| 2012/0074200 A1 | 3/2012 | Schmid et al. |
| 2012/0080336 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080478 A1 | 4/2012 | Morgan et al. |
| 2012/0080488 A1 | 4/2012 | Shelton, IV et al. |
| 2012/0080498 A1 | 4/2012 | Shelton, IV et al. |
| 2012/0199632 A1 | 8/2012 | Spivey et al. |
| 2012/0223123 A1 | 9/2012 | Baxter, III et al. |
| 2012/0228355 A1 | 9/2012 | Combrowski et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0238823 A1 | 9/2012 | Hagerty et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 9/2012 | Widenhouse et al. |
| 2012/0253298 A1 | 9/2012 | Henderson et al. |
| 2012/0283707 A1 | 11/2012 | Giordano et al. |
| 2012/0283748 A1 | 11/2012 | Ortiz et al. |
| 2012/0292367 A1 | 11/2012 | Morgan et al. |
| 2012/0298719 A1 | 11/2012 | Shelton, IV et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0030438 A1* | 1/2013 | Fox .................... A61B 17/0642 606/75 |
| 2013/0161374 A1 | 2/2013 | Swayze et al. |
| 2013/0056518 A1 | 3/2013 | Swensgard |
| 2013/0075449 A1 | 3/2013 | Schmid et al. |
| 2013/0079814 A1 | 3/2013 | Hess et al. |
| 2013/0087597 A1 | 4/2013 | Shelton, IV et al. |
| 2013/0116668 A1 | 5/2013 | Shelton, IV et al. |
| 2013/0116669 A1 | 5/2013 | Shelton, IV et al. |
| 2013/0126582 A1 | 5/2013 | Shelton, IV et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0310873 A1 | 11/2013 | Stopek et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005708 A1 | 1/2014 | Shelton, IV |

(56) References Cited

U.S. PATENT DOCUMENTS

| | | |
|---|---|---|
| 2014/0005718 A1 | 1/2014 | Shelton, IV et al. |
| 2014/0008414 A1 | 1/2014 | Shelton, IV et al. |
| 2014/0014705 A1 | 1/2014 | Baxter, III |
| 2014/0018832 A1 | 1/2014 | Shelton, IV |
| 2014/0042205 A1 | 2/2014 | Baxter, III et al. |
| 2014/0048582 A1 | 2/2014 | Shelton, IV et al. |
| 2014/0061279 A1 | 3/2014 | Laurent et al. |
| 2014/0097227 A1 | 4/2014 | Aronhalt et al. |
| 2014/0103093 A1 | 4/2014 | Koch, Jr. et al. |
| 2014/0107640 A1 | 4/2014 | Yates et al. |
| 2014/0128850 A1 | 5/2014 | Kerr et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263564 A1 | 9/2014 | Leimbach et al. |
| 2014/0263565 A1 | 9/2014 | Lytle, IV et al. |
| 2014/0263571 A1 | 9/2014 | Morgan et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |
| 2014/0309666 A1 | 10/2014 | Shelton, IV et al. |
| 2014/0326777 A1 | 11/2014 | Zingman |
| 2014/0330161 A1 | 11/2014 | Swayze et al. |
| 2014/0352463 A1 | 12/2014 | Parihar |
| 2014/0353358 A1 | 12/2014 | Shelton, IV et al. |
| 2014/0353359 A1 | 12/2014 | Hall et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0090765 A1 | 4/2015 | Hess et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0144678 A1 | 5/2015 | Hall et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |

(56) References Cited

U.S. PATENT DOCUMENTS

| | | | |
|---|---|---|---|
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289870 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101541251 A | 9/2009 |
| CN | 101675898 A | 3/2010 |
| CN | 102188270 A | 9/2011 |
| CN | 101507633 B | 2/2013 |
| CN | 101023879 B | 3/2013 |
| CN | 101401736 B | 6/2013 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 273689 C | 5/1984 |
| DE | 3709067 A1 | 9/1988 |
| DE | 4228909 A1 | 3/1994 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |

(56) References Cited

FOREIGN PATENT DOCUMENTS

| | | |
|---|---|---|
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |

(56) References Cited

FOREIGN PATENT DOCUMENTS

| | | | |
|---|---|---|---|
| EP | 1728475 | A2 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1806103 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 2030579 | B1 | 8/2008 |
| EP | 1970014 | A1 | 9/2008 |
| EP | 1980213 | A2 | 10/2008 |
| EP | 1982657 | B1 | 10/2008 |
| EP | 1759645 | B1 | 11/2008 |
| EP | 1987780 | A2 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000102 | A2 | 12/2008 |
| EP | 2005894 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | A1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090244 | A2 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110084 | A2 | 10/2009 |
| EP | 2111803 | A2 | 10/2009 |
| EP | 1762190 | B8 | 11/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165656 | A2 | 3/2010 |
| EP | 2165660 | A2 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |
| EP | 2030578 | B1 | 11/2010 |
| EP | 2036505 | B1 | 11/2010 |
| EP | 2245993 | A2 | 11/2010 |
| EP | 1627605 | B1 | 12/2010 |
| EP | 2027811 | B1 | 12/2010 |
| EP | 2130498 | B1 | 12/2010 |
| EP | 2263568 | A2 | 12/2010 |
| EP | 1994890 | B1 | 1/2011 |
| EP | 2005900 | B1 | 1/2011 |
| EP | 2286738 | A2 | 2/2011 |
| EP | 1690502 | B1 | 3/2011 |
| EP | 2292153 | A1 | 3/2011 |
| EP | 1769755 | B1 | 4/2011 |
| EP | 2090240 | B1 | 4/2011 |
| EP | 2305135 | A1 | 4/2011 |
| EP | 2308388 | A1 | 4/2011 |
| EP | 2314254 | A1 | 4/2011 |
| EP | 2316345 | A1 | 5/2011 |
| EP | 2316366 | A2 | 5/2011 |
| EP | 1813205 | B1 | 6/2011 |
| EP | 2090243 | B1 | 6/2011 |
| EP | 2329773 | A1 | 6/2011 |
| EP | 2090239 | B1 | 7/2011 |
| EP | 2340771 | A2 | 7/2011 |
| EP | 2353545 | A1 | 8/2011 |
| EP | 2361562 | A1 | 8/2011 |
| EP | 1836986 | B1 | 11/2011 |
| EP | 1908414 | B1 | 11/2011 |
| EP | 2153781 | B1 | 11/2011 |

(56) References Cited

FOREIGN PATENT DOCUMENTS

| | | |
|---|---|---|
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1616549 B1 | 10/2012 |
| EP | 2090252 B1 | 10/2012 |
| EP | 2517637 A1 | 10/2012 |
| EP | 2517638 A1 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| EP | 2090238 B1 | 4/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | 50-33988 U | 4/1975 |
| JP | S 58500053 A | 1/1983 |
| JP | S 58-501360 A | 8/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | 63-203149 A | 8/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 7-47070 A | 2/1995 |
| JP | 7-124166 A | 5/1995 |
| JP | H 7-163574 A | 6/1995 |
| JP | 07-171163 A | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 A | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 U | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344663 A | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |

(56) References Cited

FOREIGN PATENT DOCUMENTS

| | | |
|---|---|---|
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 4001860 B2 | 10/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-259860 A | 10/2008 |
| JP | 2008-264535 A | 11/2008 |
| JP | 2008-283459 A | 11/2008 |
| JP | 2009-502351 A | 1/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-536082 A | 10/2009 |
| JP | 2009-261944 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/17737 A1 | 8/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94-24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |

(56) References Cited

FOREIGN PATENT DOCUMENTS

| | | |
|---|---|---|
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 2003/079909 A3 | 3/2003 |
| WO | WO 03/030743 A2 | 4/2003 |
| WO | WO 03/037193 A1 | 5/2003 |
| WO | WO 2003/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 2003/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 2003/094746 A1 | 11/2003 |
| WO | WO 2003/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/004578 A1 | 1/2004 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/058079 A2 | 7/2004 |
| WO | WO 2004/062516 A1 | 7/2004 |
| WO | WO 2004/064600 A2 | 8/2004 |
| WO | WO 2004/078050 A2 | 9/2004 |

(56) References Cited

FOREIGN PATENT DOCUMENTS

| | | |
|---|---|---|
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2009/152307 A1 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/058213 A2 | 5/2012 |
| WO | WO 2012/068156 A2 | 5/2012 |
| WO | WO 2012/143913 A2 | 10/2012 |
| WO | WO 2012/148667 A2 | 11/2012 |
| WO | WO 2012/148703 A2 | 11/2012 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/148762 A2 | 10/2013 |
| WO | WO 2013/167427 A1 | 11/2013 |

OTHER PUBLICATIONS

U.S. Appl. No. 14/138,465, filed Dec. 23, 2013.
U.S. Appl. No. 14/138,485, filed Dec. 23, 2013.
U.S. Appl. No. 14/138,475, filed Dec. 23, 2013.
U.S. Appl. No. 14/138,489, filed Dec. 23, 2013.
U.S. Appl. No. 29/477,488, filed Dec. 23, 2013.
U.S. Appl. No. 14/138,518, filed Dec. 23, 2013.
U.S. Appl. No. 14/138,530, filed Dec. 23, 2013.
U.S. Appl. No. 14/138,507, filed Dec. 23, 2013.
U.S. Appl. No. 14/138,497, filed Dec. 23, 2013.
U.S. Appl. No. 14/138,516, filed Dec. 23, 2013.
U.S. Appl. No. 14/138,474, filed Dec. 23, 2013.
U.S. Appl. No. 14/138,505, filed Dec. 23, 2013.
U.S. Appl. No. 13/851,676, filed Mar. 27, 2013.
European Search Report for Application No. 14200137.9, dated Jul. 29, 2015 (9 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/ abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).

(56) References Cited

OTHER PUBLICATIONS

Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 a Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 30-12.
Hoffman, "Hydrogels for Biomedical Applications," Advanced Drug Delivery Reviews, 54 (2002) pp. 30-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
U.S. Appl. No. 13/763,054, filed Feb. 8, 2013.
U.S. Appl. No. 13/763,021, filed Feb. 8, 2013.
U.S. Appl. No. 13/763,037, filed Feb. 8, 2013.
U.S. Appl. No. 13/851,703, filed Mar. 27, 2013.
U.S. Appl. No. 13/851,693, filed Mar. 27, 2013.
U.S. Appl. No. 13/851,684, filed Mar. 27, 2013.
U.S. Appl. No. 13/803,097, filed Mar. 14, 2013.
U.S. Appl. No. 13/974,205, filed Aug. 23, 2013.
U.S. Appl. No. 13/974,166, filed Aug. 23, 2013.
Partial European Search Report for Application No. 14200137.9, dated Apr. 8, 2015 (6 pages).
International Search Report for Application No. PCT/US2014/069269, dated May 8, 2015 (7 pages).
International Preliminary Report on Patentability for Application No. PCT/US2014/069269, dated Jun. 28, 2016 (10 pages).

\* cited by examiner

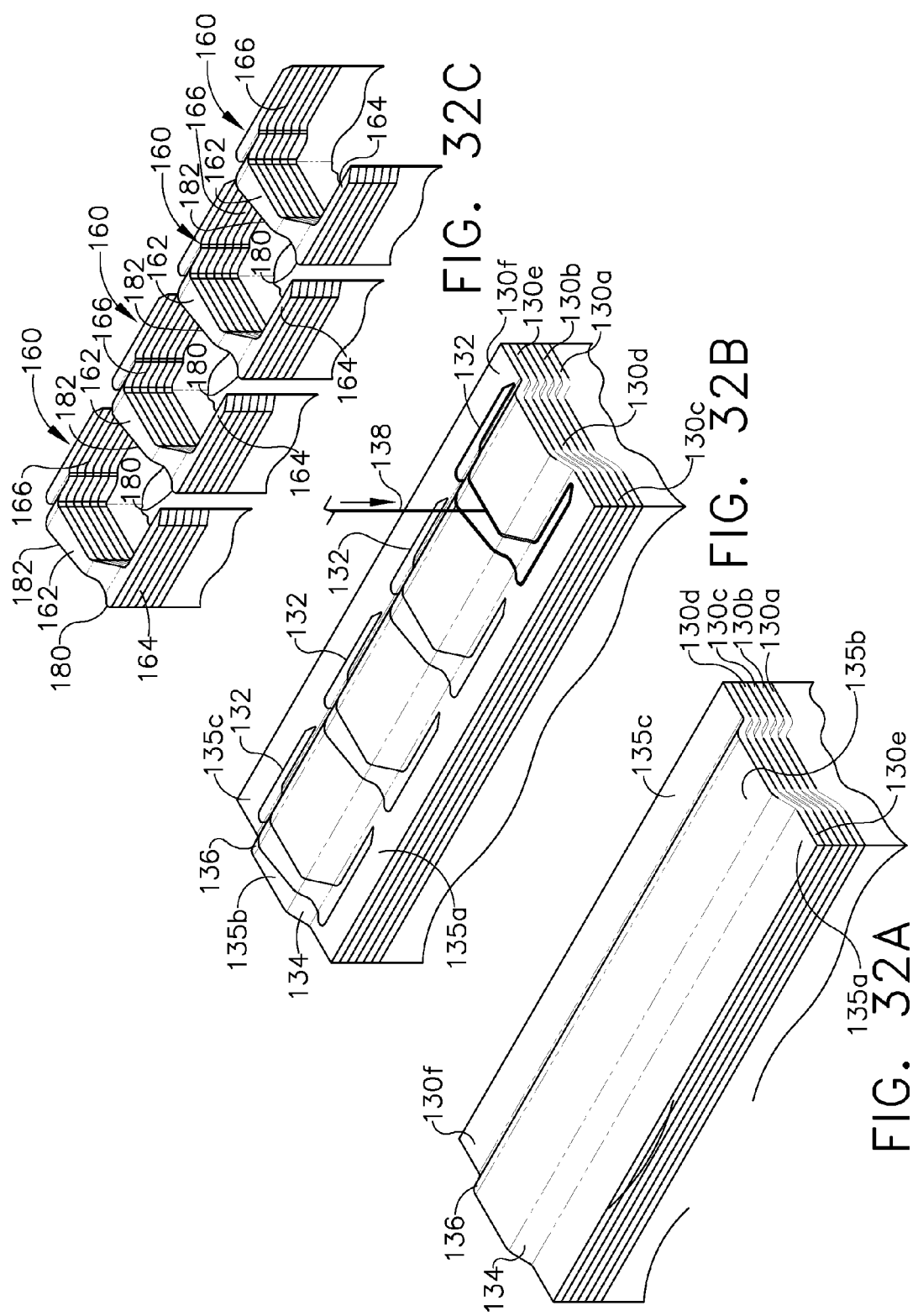

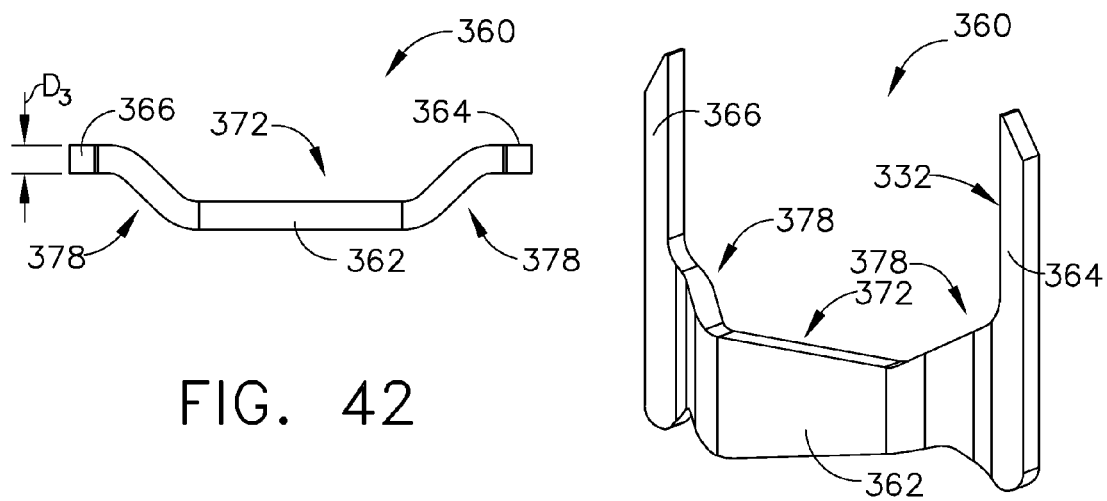
FIG. 42
FIG. 41
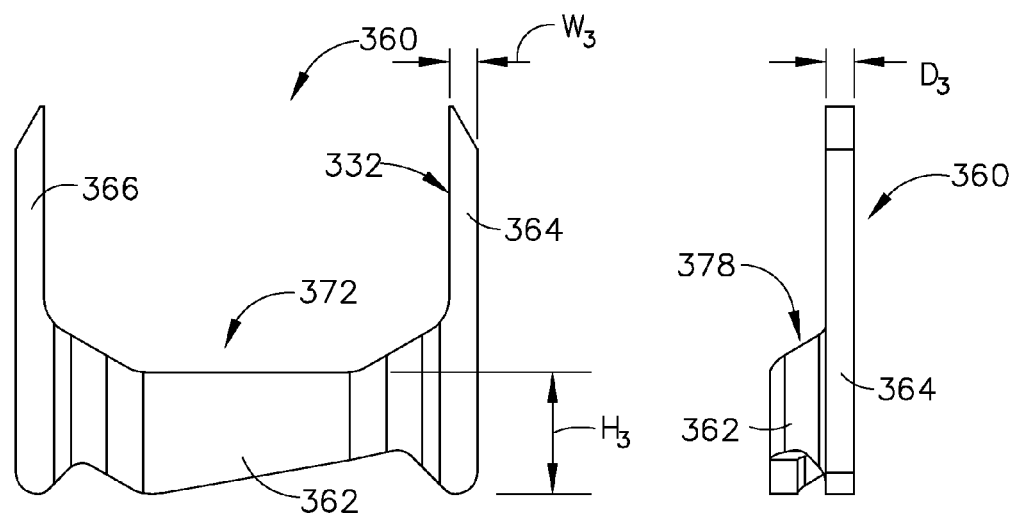
FIG. 43
FIG. 44

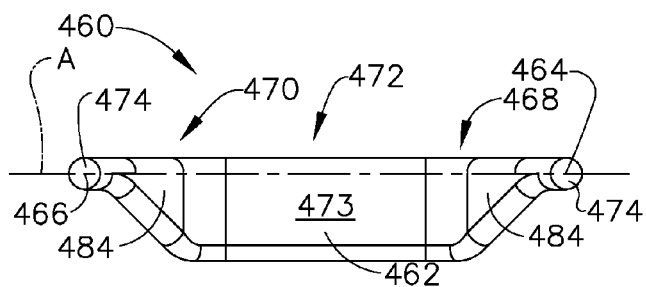
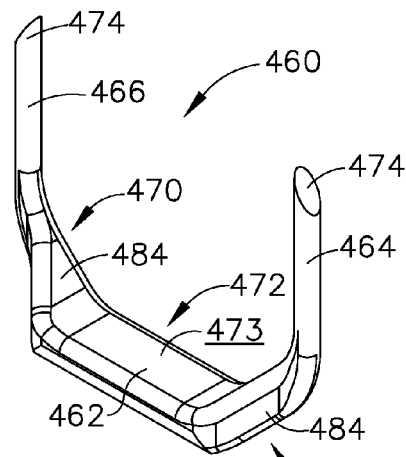
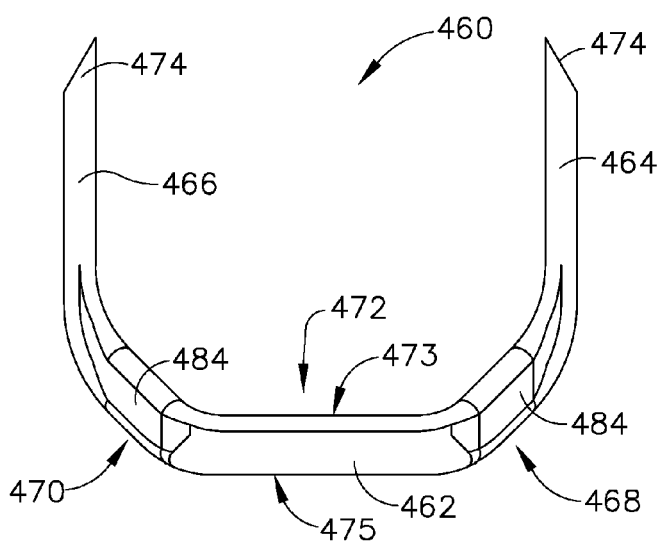
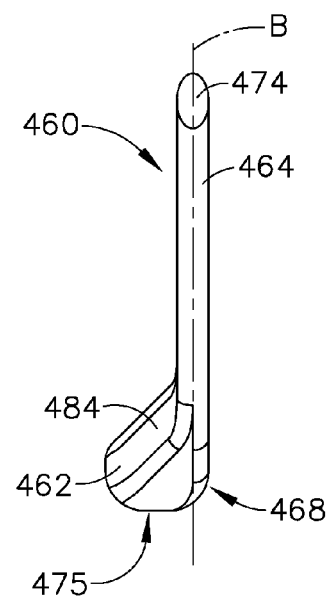
FIG. 49
FIG. 48
FIG. 50
FIG. 51

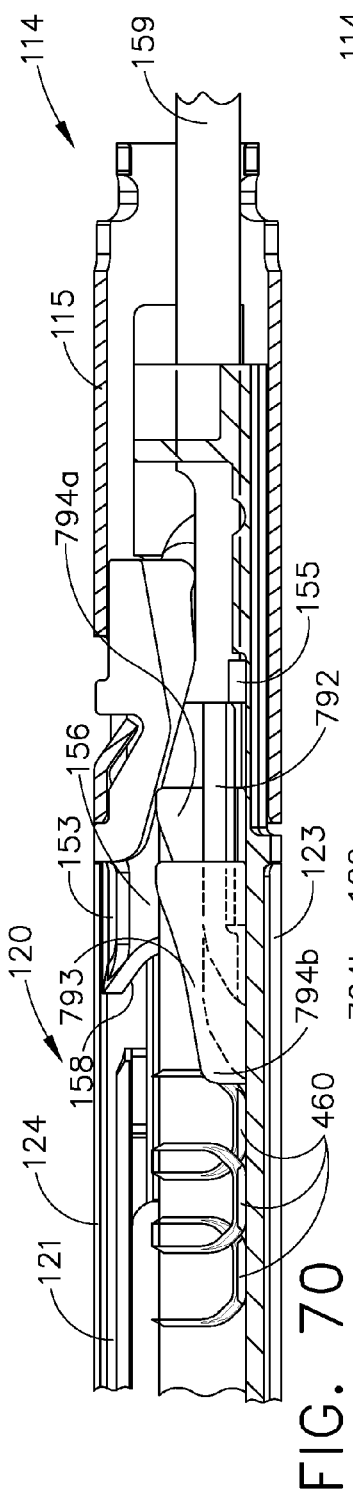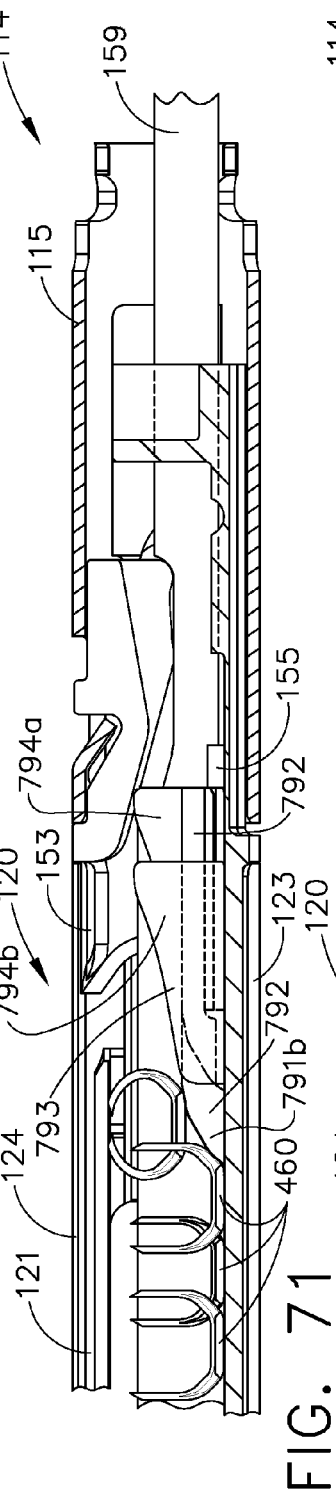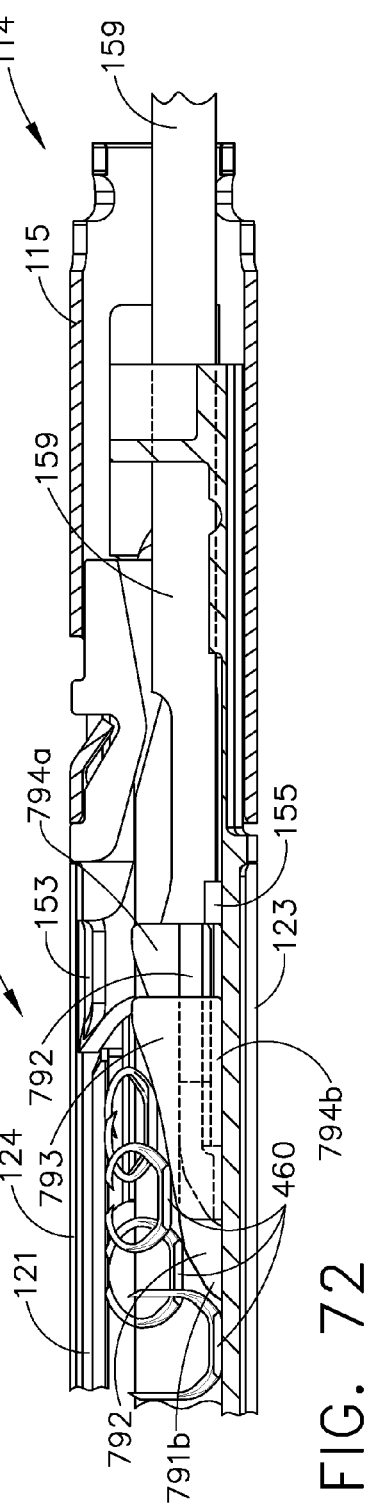

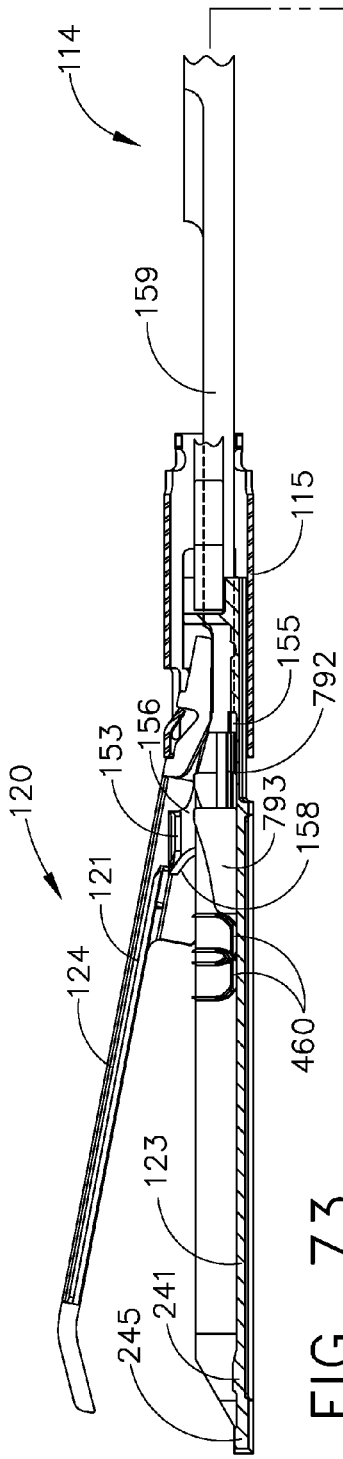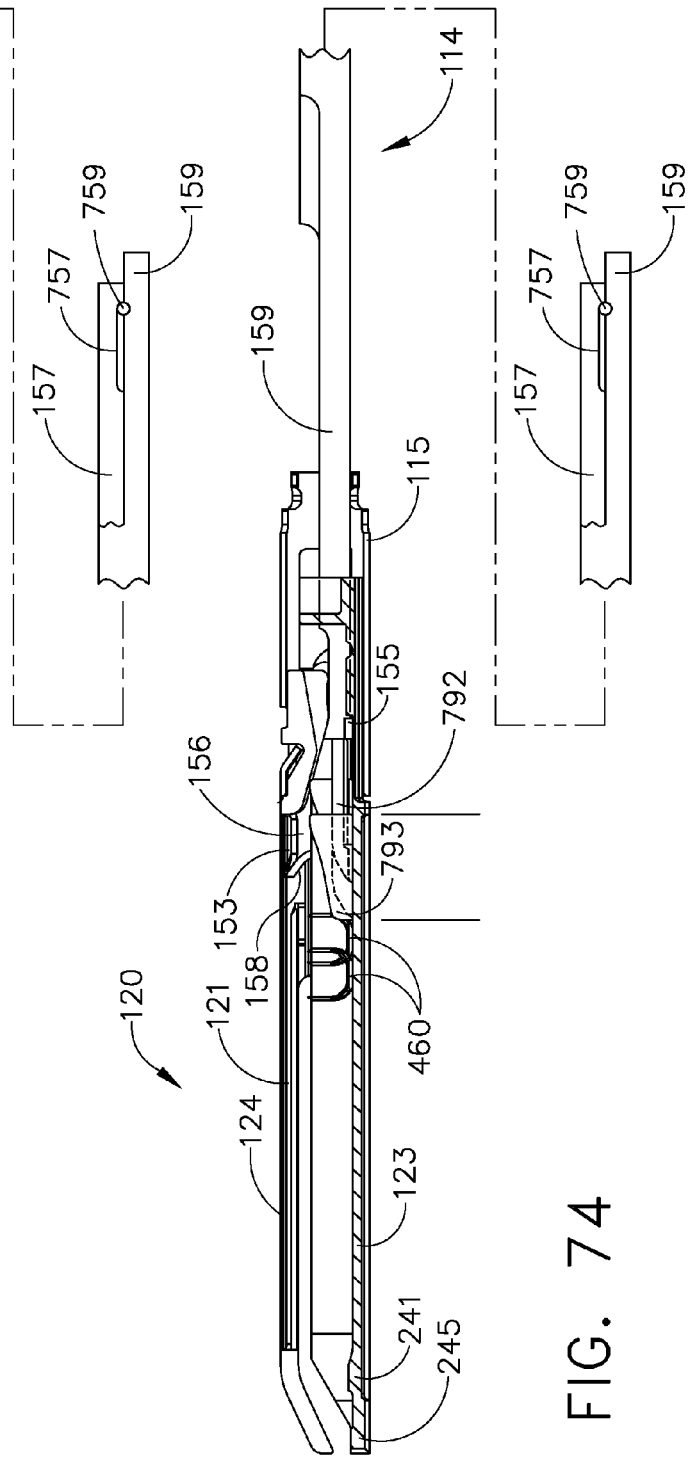

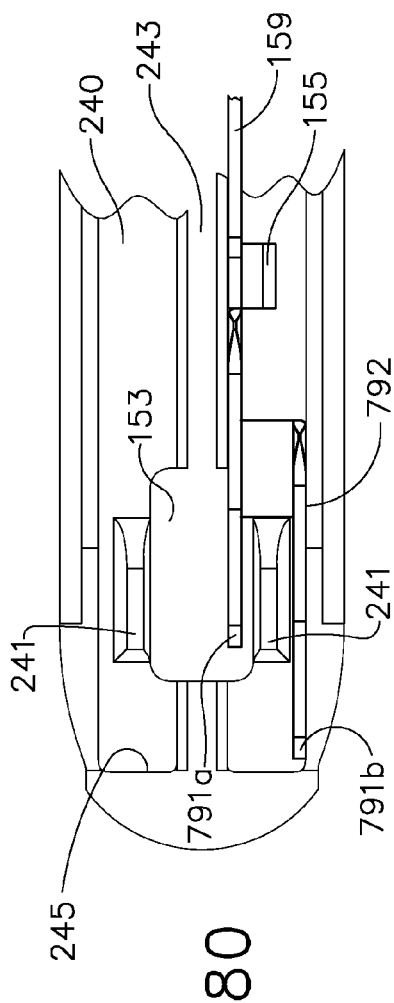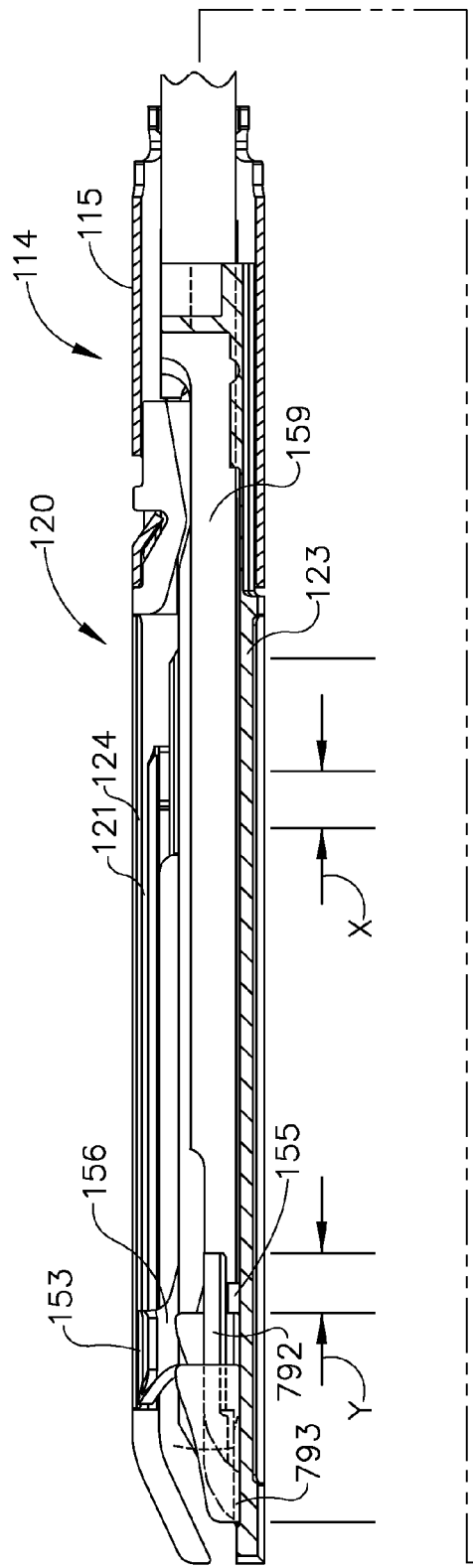

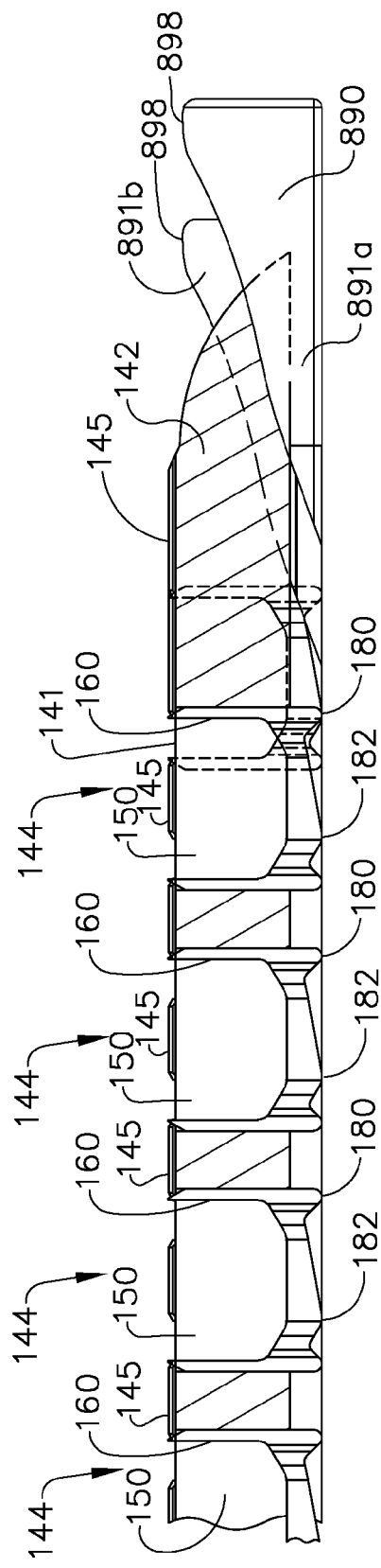
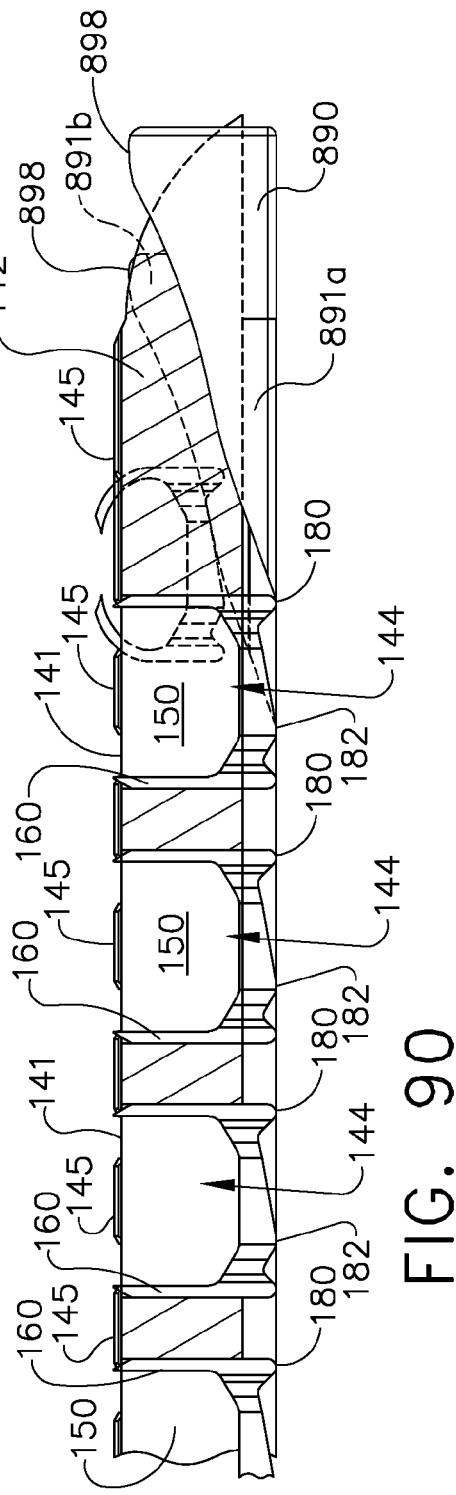
FIG. 89
FIG. 90

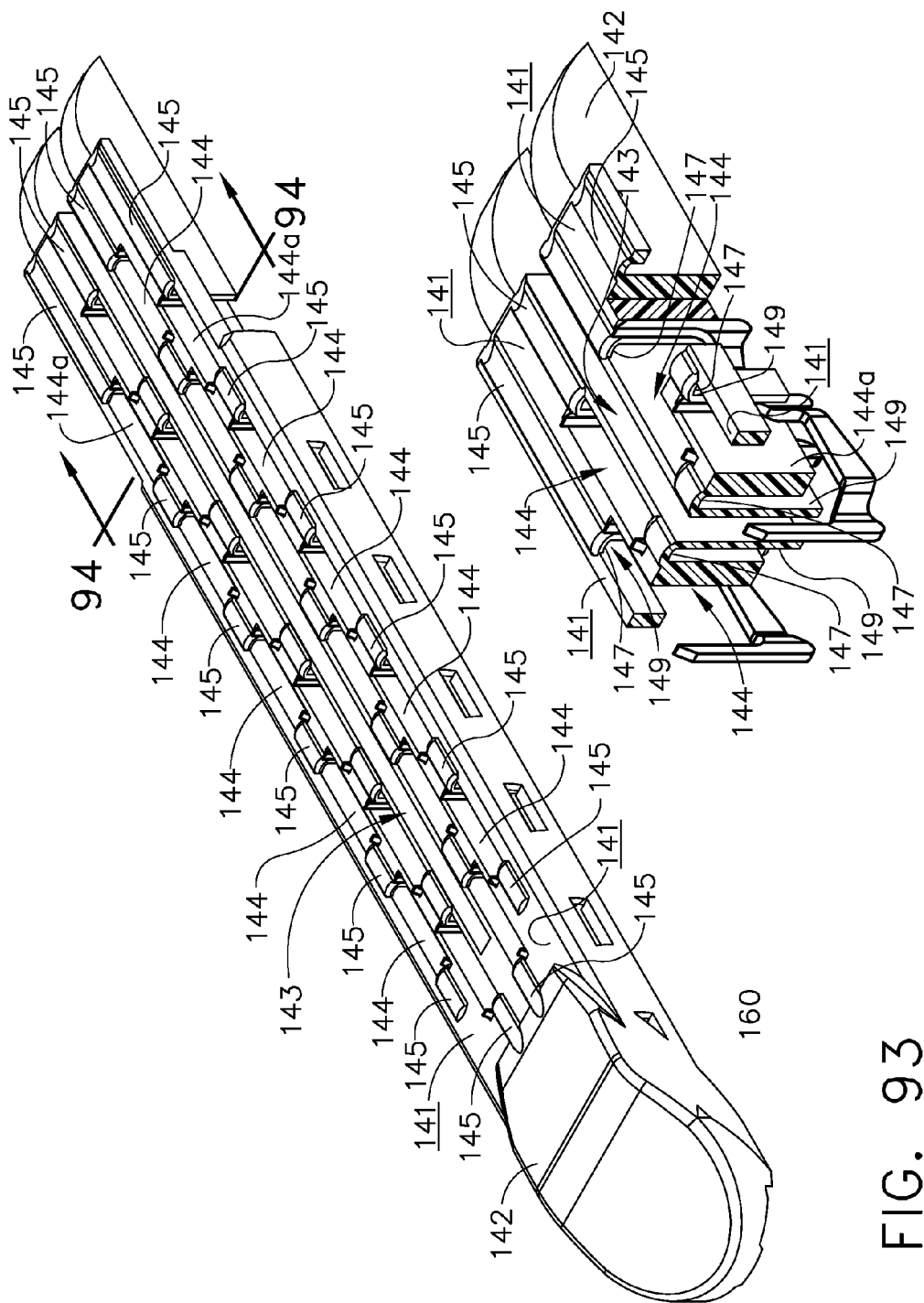

SURGICAL STAPLES AND METHODS FOR MAKING THE SAME

FIELD

The present invention relates to surgical instruments and, in various arrangements, to surgical cutting and fastening instruments that are designed to cut and fasten tissue, fastener cartridges therefor, and surgical fasteners that are designed for use therewith.

BACKGROUND

Surgical staplers are often used to deploy staples into soft tissue to reduce or eliminate bleeding from the soft tissue, especially as the tissue is being transected, for example. Surgical staplers, such as an endocutter, for example, can comprise an end effector which can be moved, or articulated, with respect to an elongated shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a sled which traverses a channel in the staple cartridge and causes the staples to be deformed against the anvil and secures layers of the soft tissue together. The sled can engage drivers positioned between the staples and the sled to deploy the staples from the staple cartridge. Often, as known in the art, the staples are deployed in several staple lines, or rows, in order to more reliably secure the layers of tissue together. Staples are typically deformed to a "B-form" by the anvil of the end effector. The end effector may also include a cutting member, such as a knife, for example, which is advanced between rows of the staples to resect the soft tissue after the layers of the soft tissue have been stapled together.

Such surgical staplers and end effectors may be sized and configured to be inserted into a body cavity through a trocar or other access opening. The end effector is typically coupled to an elongated shaft that is sized to pass through the trocar or opening. The elongated shaft assembly is often operably coupled to a handle that supports control systems and/or triggers for controlling the operation of the end effector. To facilitate proper location and orientation of the end effector within the body, many surgical instruments are configured to facilitate articulation of the end effector relative to a portion of the elongated shaft.

The foregoing discussion is intended only to illustrate various aspects of the related art in the field of the invention at the time, and should not be taken as a disavowal of claim scope.

DESCRIPTION OF THE FIGURES

The features and advantages of this invention, and the manner of attaining them, will become more apparent and the invention itself will be better understood by reference to the following description of embodiments of the invention taken in conjunction with the accompanying drawings, wherein:

FIGS. 32A-32C illustrate a method for forming staples from a sheet of material according to various embodiments of the present disclosure;

FIG. 41 is a perspective view of a staple according to various embodiments of the present disclosure;

FIG. 42 is a plan view of the staple of FIG. 41;

FIG. 43 is a front elevation view of the staple of FIG. 41;

FIG. 44 is a side elevation view of the staple of FIG. 41;

FIG. 48 is a perspective view of a staple according to various embodiments of the present disclosure;

FIG. 49 is a plan view of the staple of FIG. 48;

FIG. 50 is a front elevation view of the staple of FIG. 48;

FIG. 51 is a side elevation view of the staple of FIG. 48;

FIG. 70 is a cross-sectional view of the end effector of FIG. 65 illustrating the firing actuator in an unfired, unextended condition;

FIG. 71 is a cross-sectional view of the end effector of FIG. 65 illustrating the firing actuator in an extended condition;

FIG. 72 is a cross-sectional view of the end effector of FIG. 65 illustrating the firing actuator in an extended, advanced condition;

FIG. 73 is a cross-sectional view of the end effector of FIG. 65 illustrating an anvil of the end effector in an open position and the firing actuator in an unfired, unextended condition;

FIG. 74 is a cross-sectional view of the end effector of FIG. 65 illustrating the anvil in a closed position and the firing actuator in an unfired, unextended condition;

FIG. 80 is a partial cross-sectional plan view of the end effector of FIG. 65 illustrated in a fully-fired condition;

FIG. 81 is a cross-sectional elevational view of the end effector of FIG. 65 illustrated in the configuration depicted in FIG. 80;

FIG. 89 is a cross-sectional view of an end effector including a firing actuator configured to eject fasteners from a fastener cartridge illustrating the firing actuator in an unfired position;

FIG. 90 is a cross-sectional view of the end effector of FIG. 89 illustrating the firing actuator in a partially fired position;

FIG. 93 is a perspective view of the cartridge body of FIG. 91; and

FIG. 94 is a cross-sectional view of the cartridge body of FIG. 91 taken along line 94-94 in FIG. 93.

DETAILED DESCRIPTION

Figure 1:
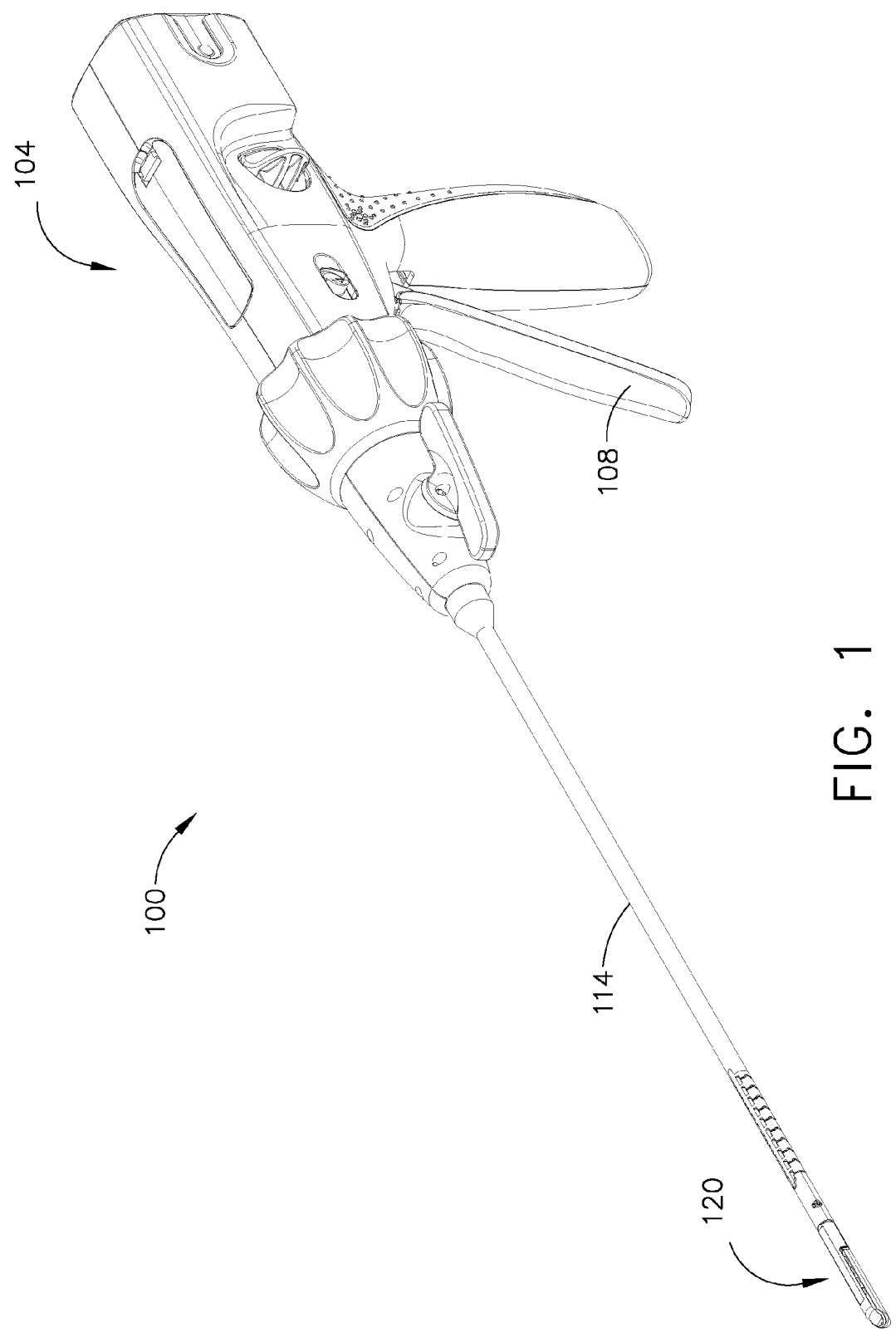
FIG. 1 is a perspective view of a surgical instrument according to various embodiments of the present disclosure.

Applicant of the present application also owns the following patent applications that were filed on Dec. 23, 2013 and which are each incorporated by reference herein in their respective entireties:

U.S. patent application Ser. No. 14/138,554, entitled Surgical Instruments With Articulatable Shaft Arrangements;

U.S. patent application Ser. No. 14/138,465, entitled SURGICAL STAPLES AND STAPLE CARTRIDGES;

U.S. patent application Ser. No. 14/138,474, entitled Articulatable Surgical Instruments With Separate and Distinct Closing and Firing Systems;

U.S. patent application Ser. No. 14/138,485, entitled Surgical Cutting and Stapling Instruments With Independent Jaw Control Features;

U.S. patent application Ser. No. 14/138,475, entitled SURGICAL STAPLES AND STAPLE CARTRIDGES;

U.S. patent application Ser. No. 14/138,489, entitled SURGICAL STAPLES, STAPLE CARTRIDGES AND SURGICAL END EFFECTORS;

U.S. Design patent application Ser. No. 29/477,488, entitled SURGICAL FASTENER;

U.S. patent application Ser. No. 14/138,505, entitled FASTENER CARTRIDGE COMPRISING AN EXTENDABLE FIRING MEMBER;

U.S. patent application Ser. No. 14/138,518, entitled FASTENER CARTRIDGE COMPRISING A FIRING MEMBER CONFIGURED TO DIRECTLY ENGAGE AND EJECT FASTENERS FROM THE FASTENER CARTRIDGE;

U.S. patent application Ser. No. 14/138,530, entitled FASTENER CARTRIDGE COMPRISING A FIRING MEMBER INCLUDING FASTENER TRANSFER SURFACES;

U.S. patent application Ser. No. 14/138,507, entitled Modular Surgical Instruments;

U.S. patent application Ser. No. 14/138,497, entitled Surgical Cutting and Stapling Instruments With Articulatable End Effectors; and U.S. patent application Ser. No. 14/138,516, entitled Surgical Cutting and Stapling Methods.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 2:
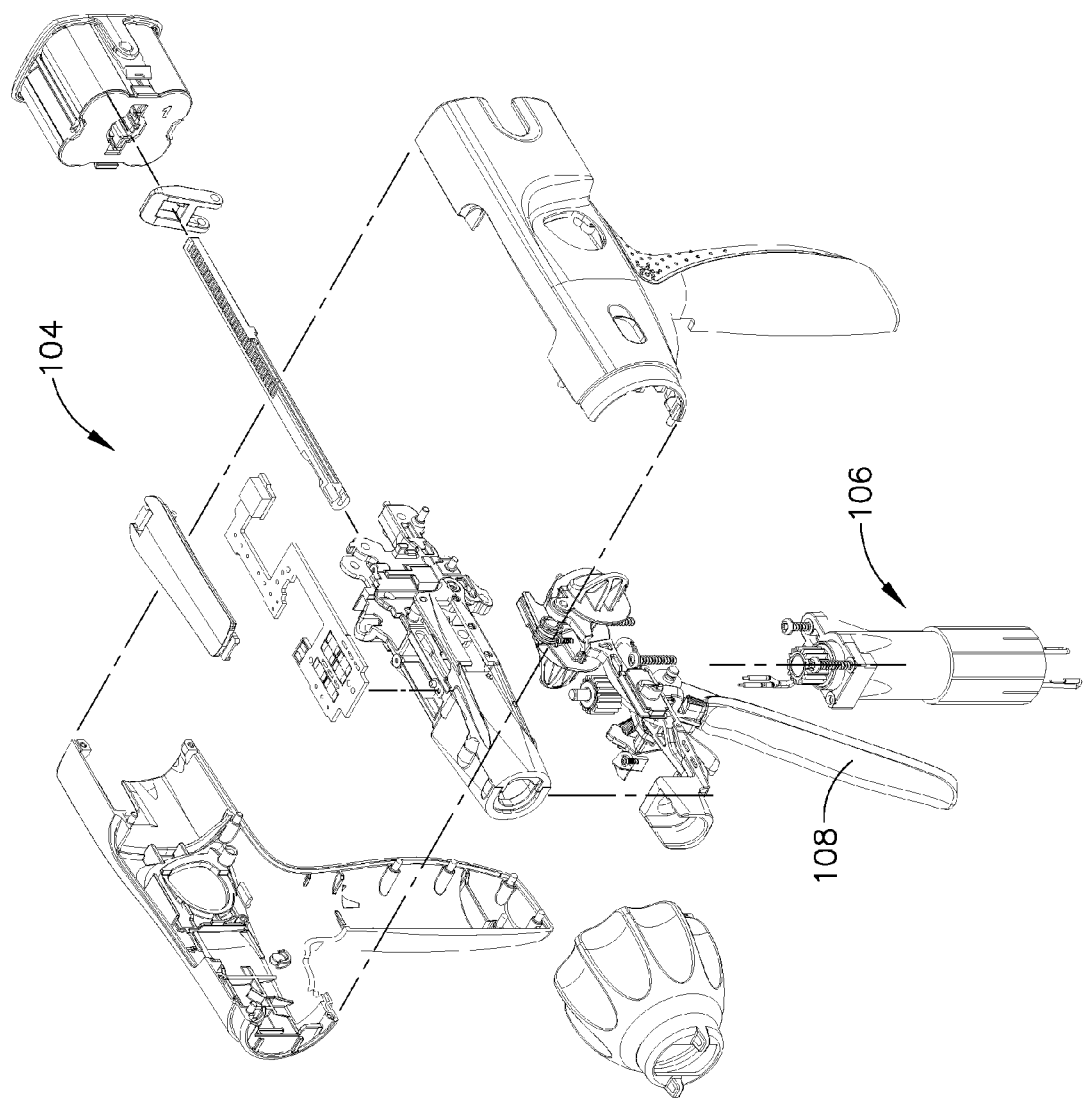
FIG. 2 is an exploded perspective view of a handle assembly of the surgical instrument of FIG. 1 according to various embodiments of the present disclosure.
Figure 3:
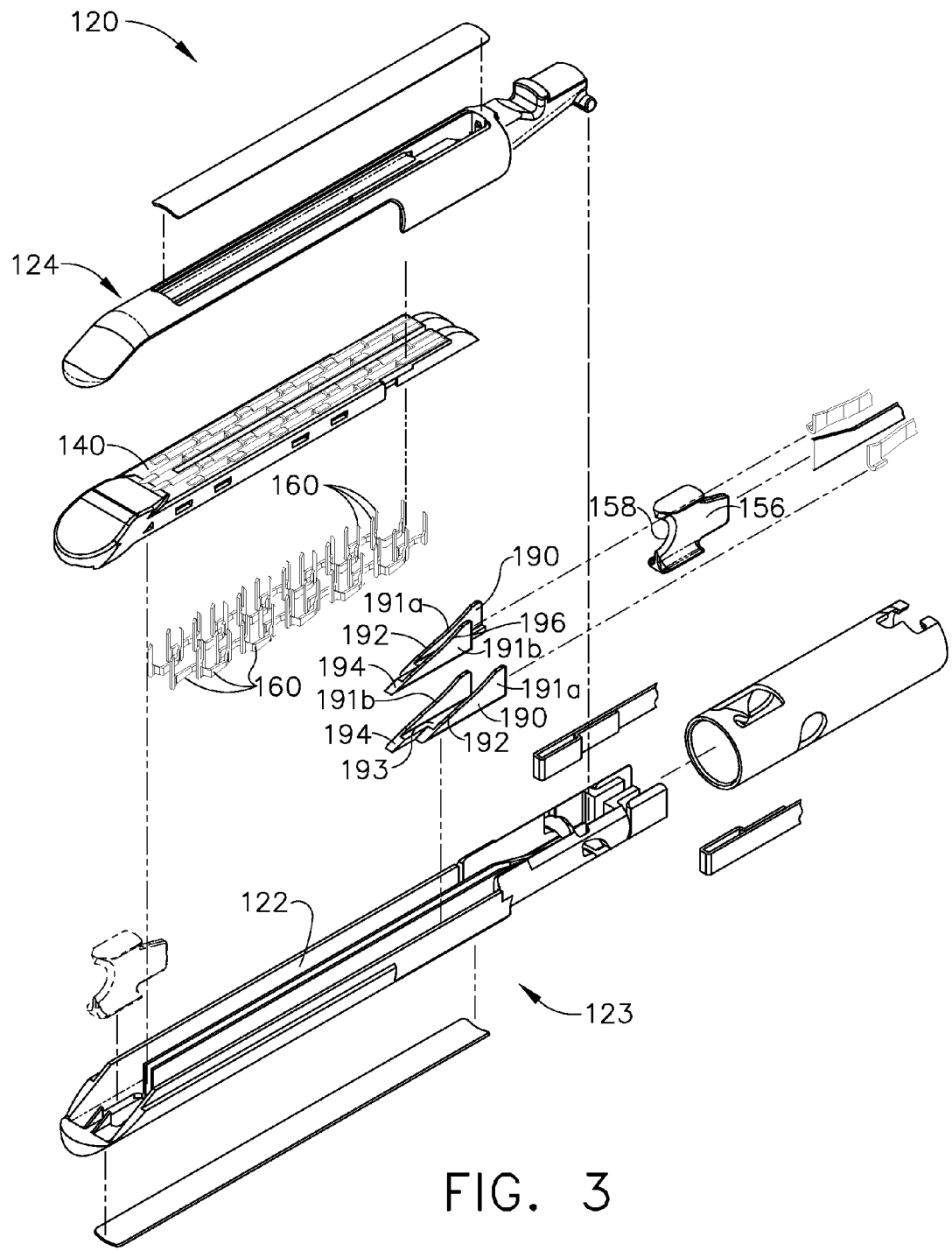
FIG. 3 is an exploded perspective view of an end effector of the surgical instrument of FIG. 1 according to various embodiments of the present disclosure.

Referring to an exemplary embodiment depicted in FIGS. 1-3, a surgical instrument 100 can include a handle assembly 104, a shaft 114 extending from the handle assembly 104, and an end effector 120 extending from the shaft 114. Referring primarily to FIG. 3, a staple cartridge 140 can be loaded into an elongate channel 122 of a first jaw 123 of the end effector 120. In certain embodiments, the staple cartridge 140 can be disposable and/or replaceable, for example. Additionally or alternatively, the staple cartridge 140 can be integrated into the end effector 120, for example, and/or the end effector 120 can be disposable and/or replaceable, for example. In various embodiments, the surgical instrument 100 can be motor-driven. For example, referring primarily to FIG. 2, a motor 106 can be positioned in the handle assembly 104. The handle assembly 104 of the surgical instrument 100 can also include a trigger 108. Actuation of the trigger 108 can affect closure of the jaws 123, 124 of the end effector 120, firing of staples 160 from the staple cartridge 140, and/or translation of a firing bar 156 and cutting element 158 through the end effector 120, for example.

Figure 4:
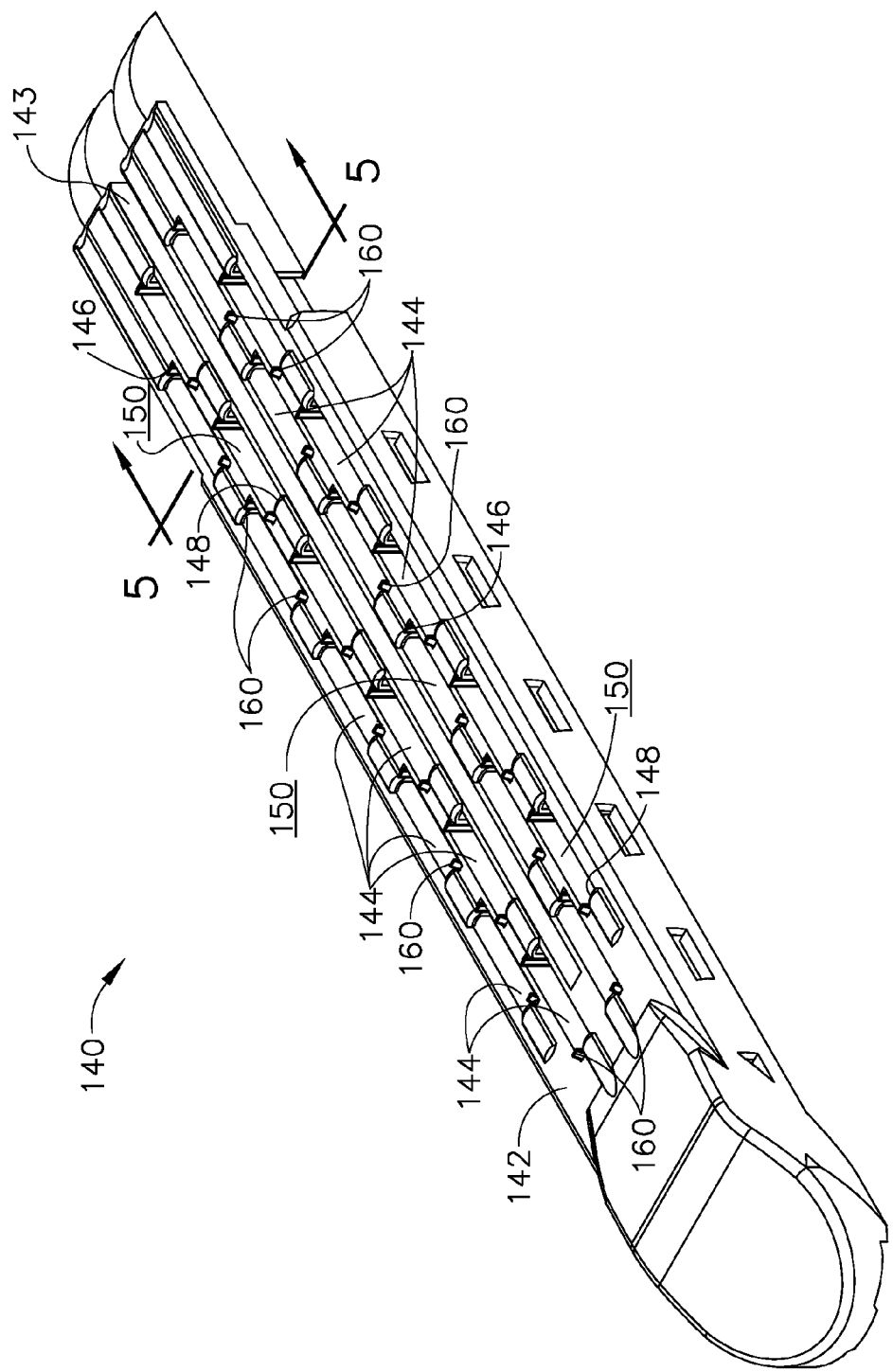
FIG. 4 is a perspective view of a staple cartridge of the end effector of FIG. 3 according to various embodiments of the present disclosure.
Figure 5:
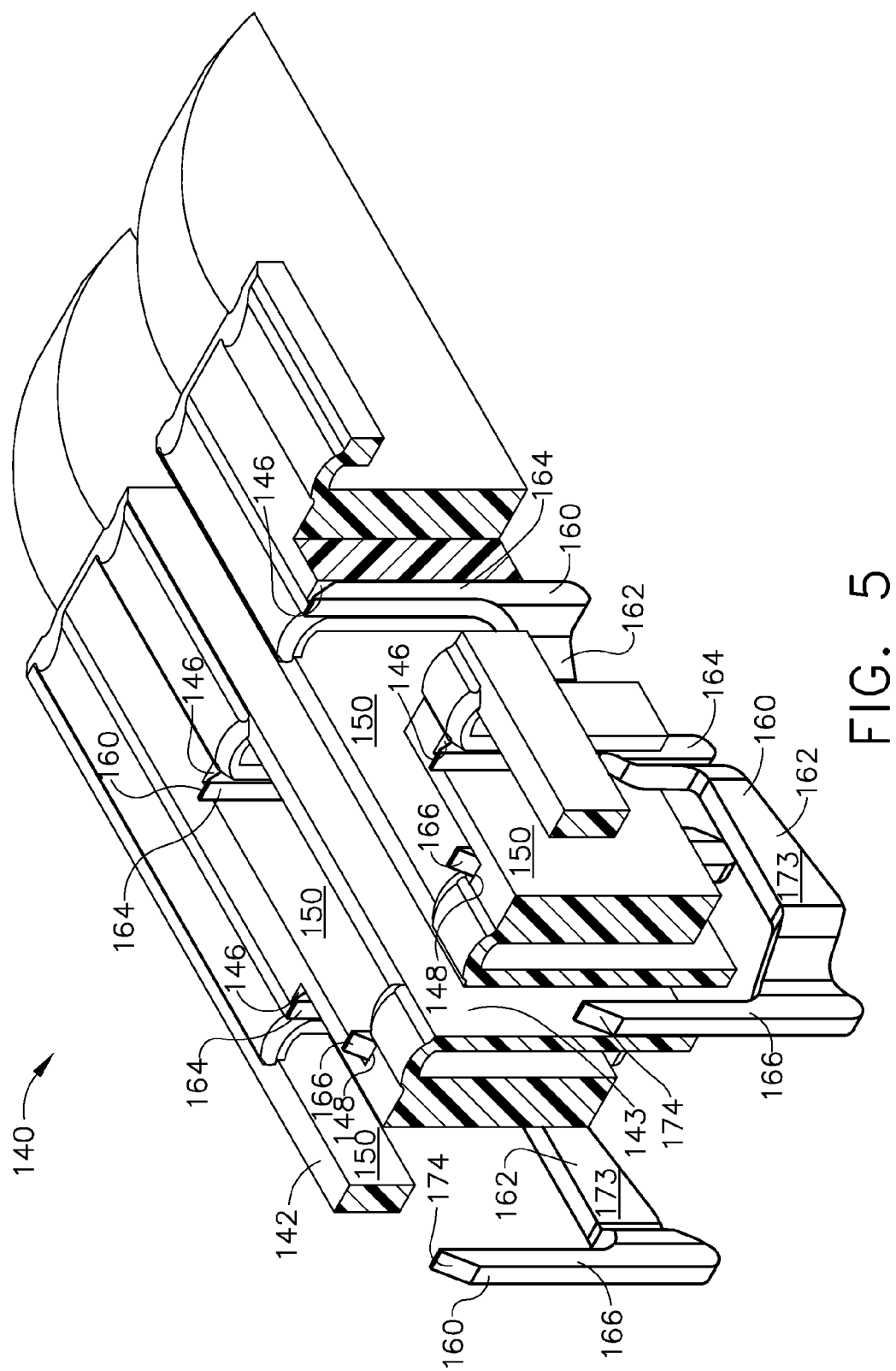
FIG. 5 is a cross-sectional perspective view of the staple cartridge of FIG. 4 taken along the plane indicated in FIG. 4 according to various embodiments of the present disclosure.
Figure 6:
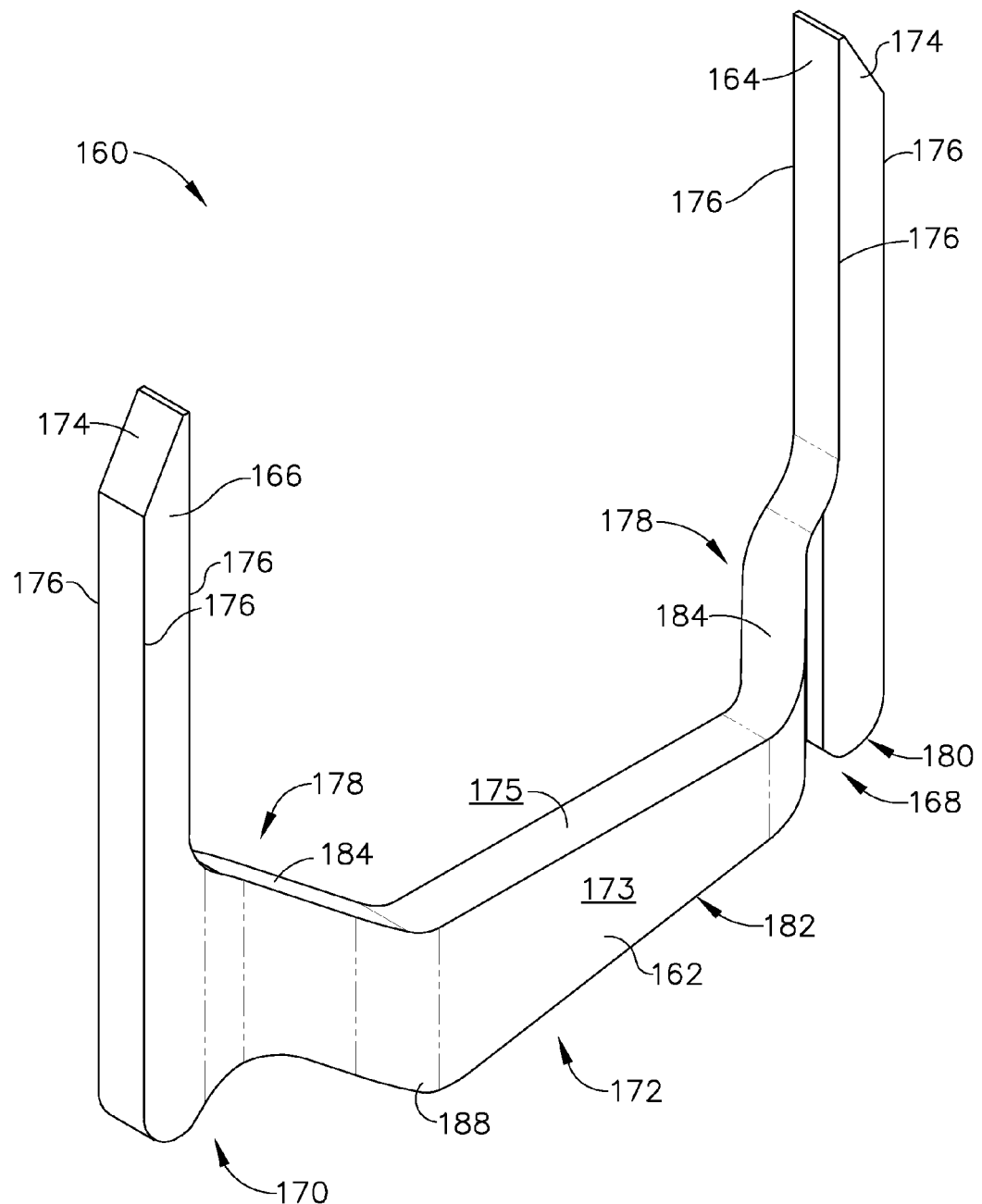
FIG. 6 is a perspective view of the staple depicted in the staple cartridge of FIG. 4 according to various embodiments of the present disclosure.

Referring primarily to FIG. 3, staples 160 can be ejectably positioned in the staple cartridge 140. For example, at least one sled 190 can translate through the staple cartridge 140 to eject the staples 160 from the staple cartridge 140. The firing bar 156 having the cutting element or knife 158 can also translate through the staple cartridge 140 to cut tissue captured between the end effector jaws, 123, 124, for example. As depicted in FIG. 3, the firing bar 156 and cutting element 158 can move from a proximal position in the first jaw 123 to a distal position in the first jaw 123. In various embodiments, tissue positioned intermediate the staple cartridge 140 and the anvil 124 can be stapled by the staples 160, and then cut by the cutting element 158, for example. Referring primarily to FIGS. 4 and 5, the staple cartridge 140 can include a cartridge body 142 and staple cavities 144 defined in the cartridge body 142. Staples, such as staples 160, for example, can be removably positioned in the staple cavities 144. In certain embodiments, each staple cavity 144 can removably store a single staple 160. Each staple cavity 144 can have a proximal end 146 and a distal end 148, for example, and longitudinal sidewalls 150 can extend between the proximal end 146 and the distal end 148 of each staple cavity 144. As described in greater detail herein, the proximal ends 146, the distal ends 148, and/or the longitudinal sidewalls 150 of the staple cavity 144 can guide and/or support the staple 160 during deployment from the staple cavity 144.

Referring now to FIGS. 6-13, the staple 160 can include a base 162, a first staple leg 164 extending from the base 162, and a second staple leg 166 extending from the base 162. The base 162 can have a proximal portion 168 and a distal portion 170, for example, and an intermediate portion 172 of the base 162 can be positioned between the proximal portion 168 and the distal portion 170, for example. As depicted in FIGS. 6-13, the first staple leg 164 can extend from the proximal portion 168 of the base 162, and the second staple leg 166 can extend from the distal portion 170 of the base 162. The staple legs 164, 166 can include a tip 174, for example, which can have a pointed or substantially pointed end. In various embodiments, the tip 174 can facilitate piercing into and/or through tissue, for example. In certain embodiments, the staple legs 164, 166 can include corner edges 176, which can be sharp, or substantially sharp, for example, and can also facilitate piercing into and/or through tissue, for example. In other embodiments, the staple legs 164, 166 can include rounded corner edges.

Referring still to FIGS. 6-13, chamfers 184, 186 can be positioned between the staple legs 164, 166 and the base 162. For example, an upper chamfer 184 can extend between the staple legs 164, 166 and the base 162, and/or a lower chamfer 186 can extend between the staple legs 164, 166 and the base 162. When tissue is captured by the staple 160, the tissue can be compressed between the base 162 and the deformed staple legs 164, 166, and the chamfers 184, 186 may contact the compressed tissue. In various embodiments, the chamfers 184, 186 can compress the captured tissue, for example, and may prevent the base 162 from unintentionally piercing and/or cutting the captured tissue, for example.

In various embodiments, the base 162 of the staple 160 may be asymmetrical relative to the staple legs 174, 176. For example, referring primarily to FIG. 10, a first axis A may be defined between the first and second staple legs 174, 176, and the base 162 can be asymmetrical relative to the first axis A. The base 162 can be non-linear, for example, and can include at least one laterally contoured portion 178 that bends or curves away from the axis A. The base 162, or at least a portion of the base 162, can be defined by a second axis B. The contoured portion 178 can be include straight and/or curved regions, and may be generally non-parallel to the first axis A and the second axis B, for example. For example, the contoured portion 178 can bend or curve away from the first axis A, include a straight or substantially straight portion, and bend or curve toward the second axis B (FIG. 10).

Figure 10:
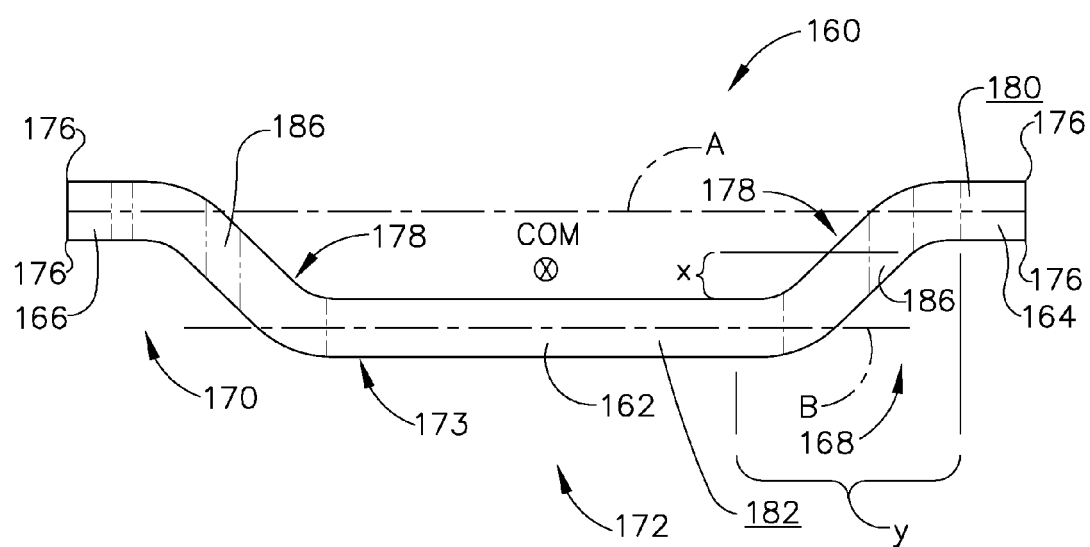
FIG. 10 is a bottom plan view of the staple of FIG. 6.
Figure 11:
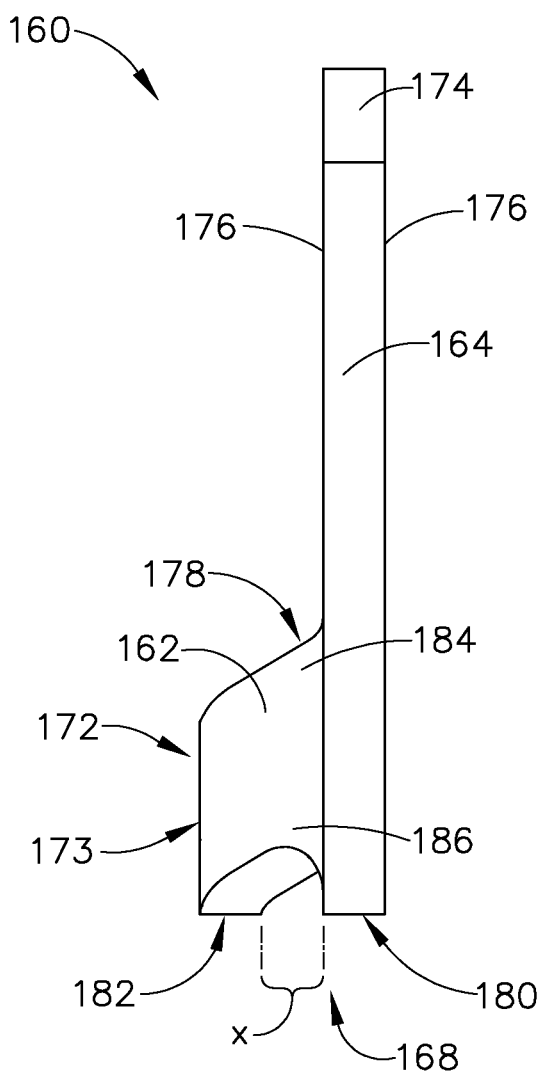
FIG. 11 is a right elevation view of the staple of FIG. 6.
Figure 12:
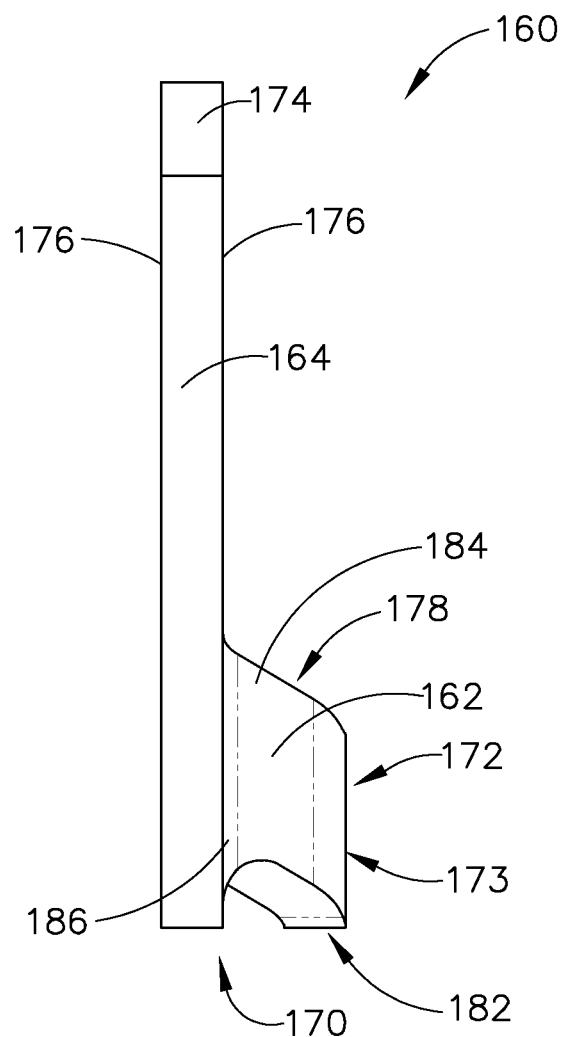
FIG. 12 is a left elevation view of the staple of FIG. 6.
Figure 13:
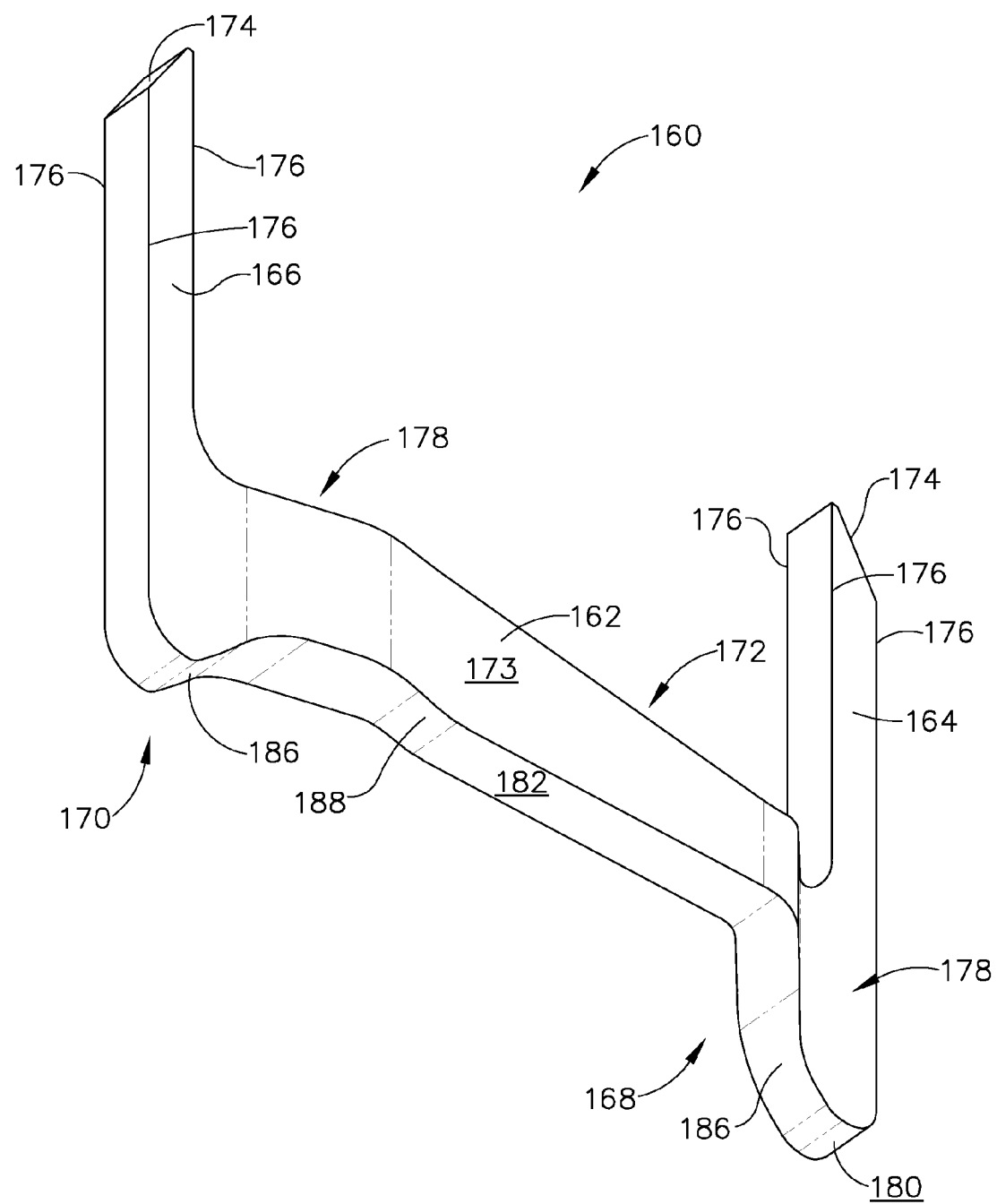
FIG. 13 is a perspective view of the staple of FIG. 6.

Referring still to FIG. 10, the center of mass (COM) of the staple 160 can be offset from the first axis A. In various embodiments, a portion of the base 162 can extend along the second axis B, for example, which can be parallel or substantially parallel to the first axis A. For example, the intermediate portion 172 of the base 162 can be parallel or substantially parallel to the first axis A. A contoured portion 178 can be positioned between the proximal portion 168 and the intermediate portion 172, for example, and another contoured portion 178 can be positioned between the distal portion 170 and the intermediate portion 172, for example. The contoured portions 178 can laterally offset the intermediate portion 172 of the base 162 from the staple legs 164, 166 and from the first axis A, for example. In certain embodiments, the staple legs 164, 166 can be positioned in a first plane defined by the first axis A, for example, and the intermediate portion 172 of the base 162 can be positioned in a second plane defined by the second axis B. The second plane can be parallel, or substantially parallel, to the first plane, for example, and the center of mass (COM) of the staple 160 can be positioned between the first plane and the second plane. In such embodiments, the staple 160 can include a leg formation plane, e.g., the plane defined by the first axis A, which can be offset from the COM of the staple 160. For example, deformation of the staple 160 can form a modified "B-form", for example, and the staple legs 164, 166 may be non-coplanar and/or laterally offset from the intermediate portion 172 of the staple base 162. In various instances, the modified "B-form" staple formation can engage, capture, compress, and/or affect a greater volume of tissue, for example. Additionally, in certain instances, the modified "B-form" staple formation can exert forces on the engaged tissue in different and/or divergent directions, for example. Modified "B-form" can define a tissue entrapment area extending in three different directions. For instance, a portion of the tissue entrapment area can be defined in two directions by the legs 164 and 166 and another portion of the tissue entrapment area can be defined in a third direction between the base 162 and the legs 164, 166.

In various embodiments, the intermediate portion 172 of the staple base 162 can include a longitudinal guide surface 173. For example, as described in greater detail herein, the longitudinal guide surface 173 can slide and/or move against a guide surface 150 in the staple cavity 144 (FIGS. 4 and 5) as the staple 160 is fired and/or ejected from the cartridge body 142 (FIGS. 4 and 5), for example. In such embodiments, the longitudinal guide surface 173 can balance and/or stabilize the staple 160 during deployment. Furthermore, the intermediate portion 172 of the staple base 162 can include a tissue-contacting surface 175 (FIG. 9), which can be flat or substantially flat, for example. In various instances, the tissue-contacting surface 175 of the base 162 can form a flat surface for contacting captured tissue, which can provide a broad and/or smooth surface for applying and/or distributing pressure on the captured and/or compressed tissue. In such embodiments, tissue tearing and/or trauma within the staple 160 may be reduced and/or minimized, for example.

In various embodiments, the base 162 of the staple 160 can include one of more drive surfaces. For example, the base 162 can include an initial drive surface 180 and a secondary drive surface 182. Referring still to FIGS. 6-13, the proximal portion 168 of the base 162 can include the initial drive surface 180, for example, and/or the intermediate portion 172 of the base 172 can include the secondary drive surface 182. For example, the proximal portion 168 can include a nub having the first drive surface 180. The nub of the first drive surface 180 can include a rounded and/or sloped surface, for example. The secondary drive surface 182 can comprise a ramp on the intermediate portion 172 of the base 162. For example, the secondary drive surface 182 can be positioned distal to the initial drive surface 180 and/or between the proximal portion 168 and the distal portion 170 of the base 162, for example. The secondary drive surface 182 can include an inclined surface or plane, for example, and can slope downward in the direction of the distal portion 170 (see FIGS. 7 and 8).

Figure 7:
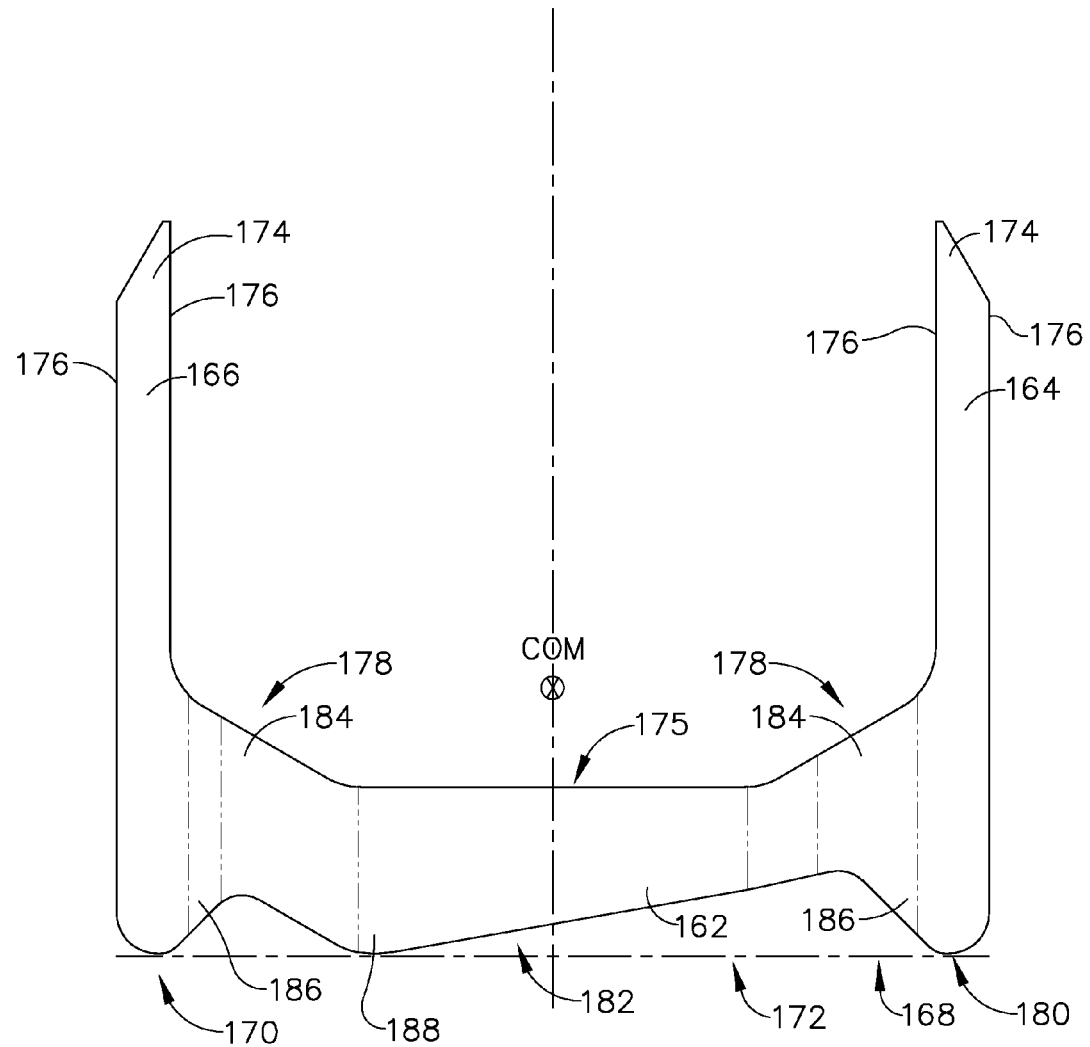
FIG. 7 is a front elevation view of the staple of FIG. 6.
Figure 8:
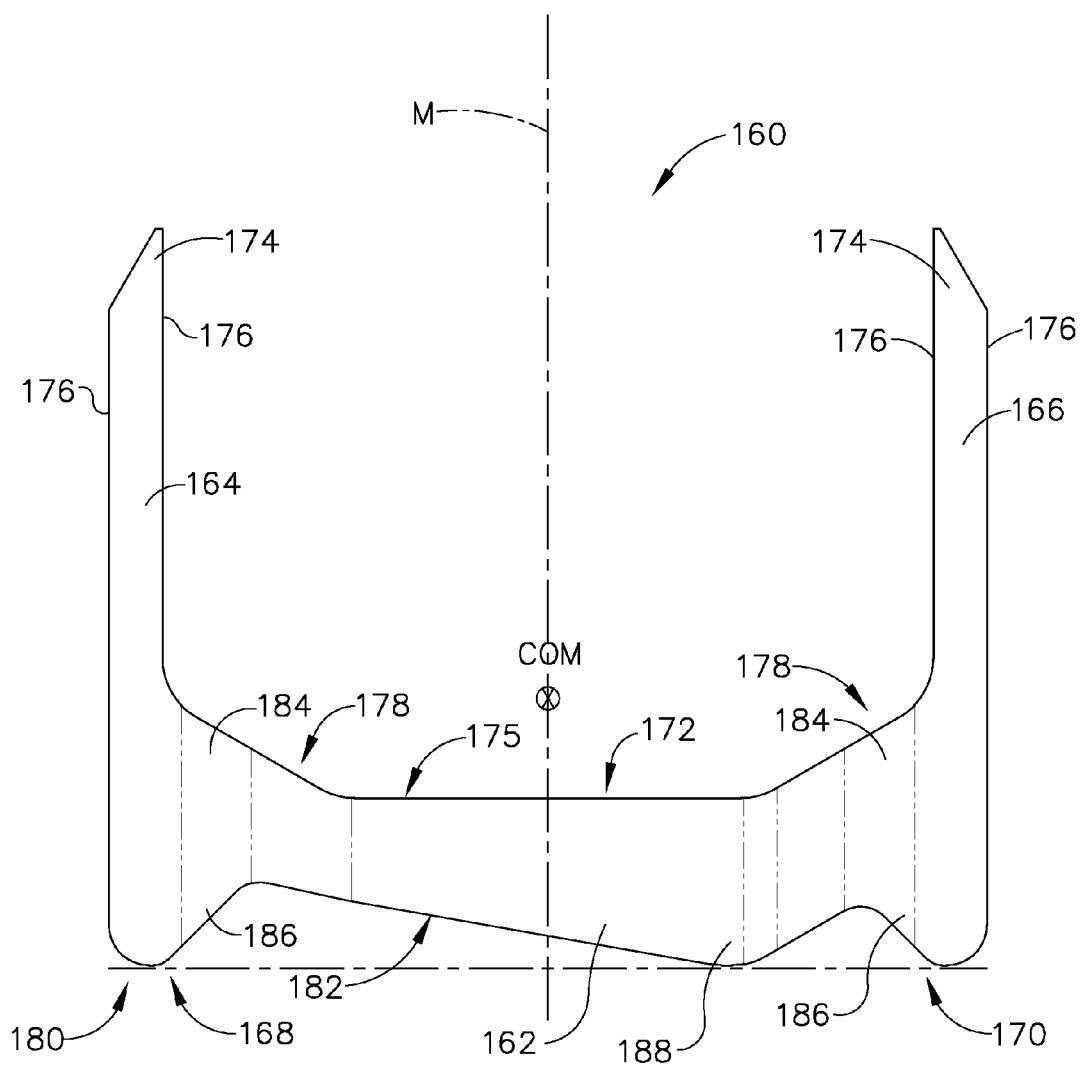
FIG. 8 is a rear elevation view of the staple of FIG. 6.
Figure 9:
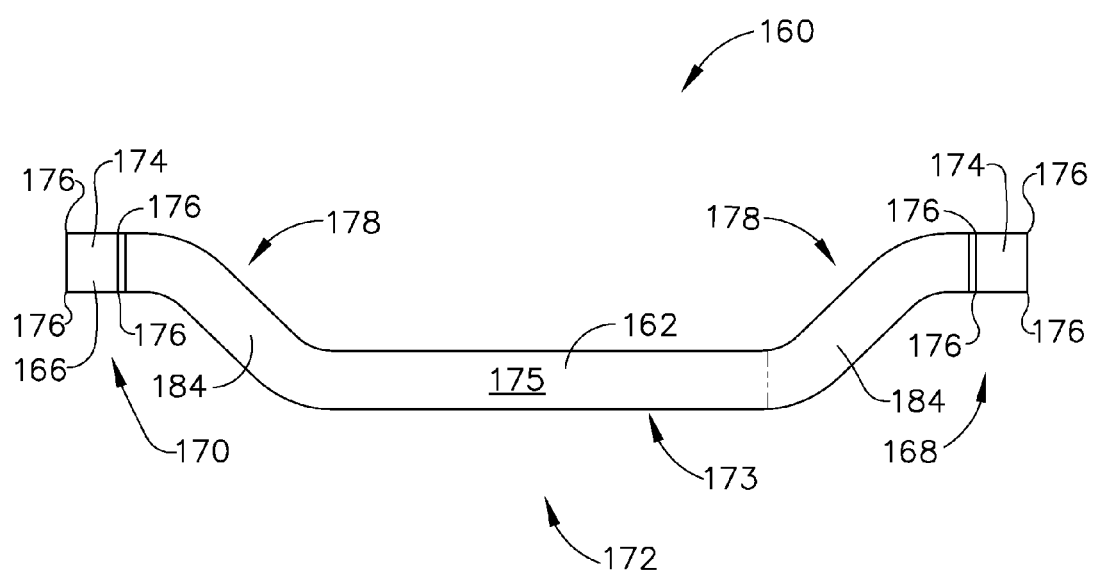
FIG. 9 is a top plan view of the staple of FIG. 6.

Referring primarily to FIGS. 7 and 8, a staple midline M can be defined intermediate the first staple leg 164 and the second staple leg 166. The staple midline M can bisect the staple 160, and can pass through the center of mass (COM) of the staple 160, for example. In various embodiments, the secondary drive surface 182 can extend across the midline M. For example, the secondary drive surface 182 can extend along the intermediate portion 172 of the base 162, and can cross from a proximal side of the midline M to a distal side of the midline M. In such embodiments, during deployment of the staple 160 via the sled 190, as described in greater detail herein, a ramp 192 of the sled 190 can drive the staple 160 at and/or near the midline M of the staple 160 during a portion of the staple's deployment. In various embodiments, the distal end of the secondary drive surface 182 can also include a staple overdrive 188, which is described in greater detail herein. Referring primarily to FIG. 7, the staple overdrive 188 can include the lowest point of the intermediate portion 172 of the base 162 and, in some embodiments, can be vertically aligned with the lowest point of the proximal portion 168 and/or the distal portion 170 of the base 162, for example. In other embodiments, the staple overdrive 188 may be positioned vertically below or above the lowest portion of the proximal portion 168 and/or the distal portion 170 of the base 162.

In various embodiments, the drive surfaces 180, 182 of the staple 160 can be separate and distinct. For example, the drive surfaces 180, 182 can be laterally and/or longitudinally offset, such that the drive surfaces 180, 182 are unconnected and/or nonadjacent. Each drive surface can be discrete, for example. The initial drive surface 180 can overlap a first plane (see axis A in FIG. 10), for example, and the secondary drive surface 182 can overlap a second plane (see axis B in FIG. 10), for example. In certain embodiments, the drive surfaces 180, 182 can be parallel. For example, the initial drive surface 180 can extend along the first axis A (FIG. 10), and the secondary drive surface 180 can extend along the second axis B (FIG. 10). In various embodiments, a lateral gap having a width x (FIGS. 10 and 11) can be defined between the initial drive surface 180 and the secondary drive surface 182, for example. In some embodiments, a longitudinal gap having a width y (FIG. 10) can be defined between the initial drive surface 180 and the secondary drive surface 182, for example. The initial drive surface 180 can be proximal to the secondary drive surface 182, for example. Furthermore, a non-driven portion of the base, such as the lower chamfer 186 of the contoured portion 178 between the proximal portion 168 and the intermediate portion 172, for example, can separate the initial drive surface 180 and the secondary drive surface 182, for example. In various embodiments, the contoured portions 178 can traverse between the first plane defined by axis A and the second plane defined by axis B, for example.

Referring still to FIGS. 6-13, at least one of the drive surfaces 180, 182 of the staple 160 can be integrally formed with the staple 160. For example, the drive surfaces 180, 182 can be defined in the base 162 of the staple 160. The staple 160 can comprise a single, unitary piece, for example, which may integrally include the drive surfaces 180, 182. The drive surfaces 180, 182 can comprise a boundary or perimeter surface of the single, unitary piece, for example. In various circumstances, the staple 160 can be seamless, for example, and many not include any adhered and/or overmolded features, for example. Furthermore, the base 162 and the staple legs 164, 166 can be a contiguous part, and the base 162 can integrally define the drive surfaces 180, 182, for example. In certain instances, as described in greater detail herein, the staple 160 can be stamped or otherwise formed from a single piece of material, for example, and can remain a single piece of material, for example. In various instances, the drive surfaces 180, 182 can comprise a surface or flat of the formed piece.

Referring now to FIGS. 14-17, the sled 190 can drive the staples 160 from the cavities 144 in the cartridge body 142 (FIG. 3). In various instances, the sled 190 can directly contact the staples 160 and/or can directly drive the staples 160. For example, the sled 190 can include a ramp or inclined surface 192, which can contact at least one drive surface 180, 182 of the staple 160. As the sled 190 translates relative to the staple 160, the ramp 192 can push the drive surfaces 180, 182 to lift the staples 160. In various embodiments, the degree of incline of the ramp 192 can vary along the length thereof. For example, the ramp 192 can be designed to lift the staple 160 faster and/or slower during at least part of the staple's deployment. Moreover, the degree of incline of the ramp 192 can be designed and/or selected based on the degree of incline of a staple drive surface 180, 182. For example, the ramp 192 can define an incline that is greater than, less than, and/or equal to the incline of the initial drive surface 180 and/or the secondary drive surface 182. The relationship between the ramp 192 incline and the drive surface 180, 182 incline can affect the speed of staple deployment, for example.

Figure 14:
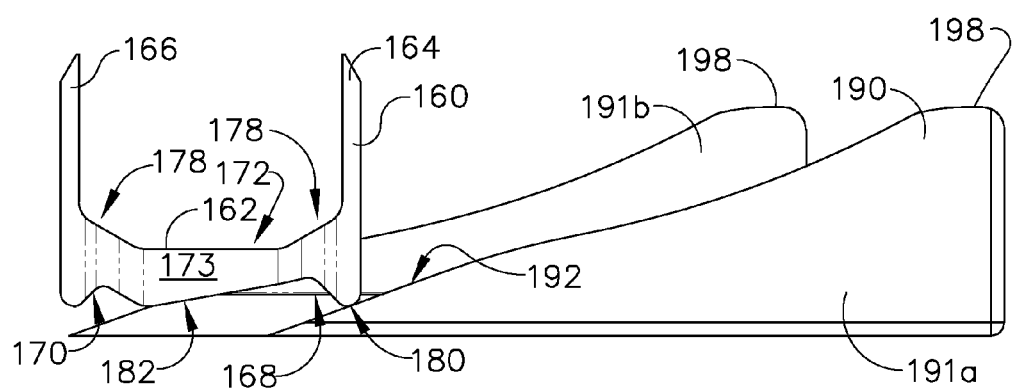
FIG. 14 is an elevation view of the staple of FIG. 6 and a sled of the end effector of FIG. 3, depicting a leading surface of the sled contacting an initial drive surface of the staple, according to various embodiments of the present disclosure.
Figure 15:
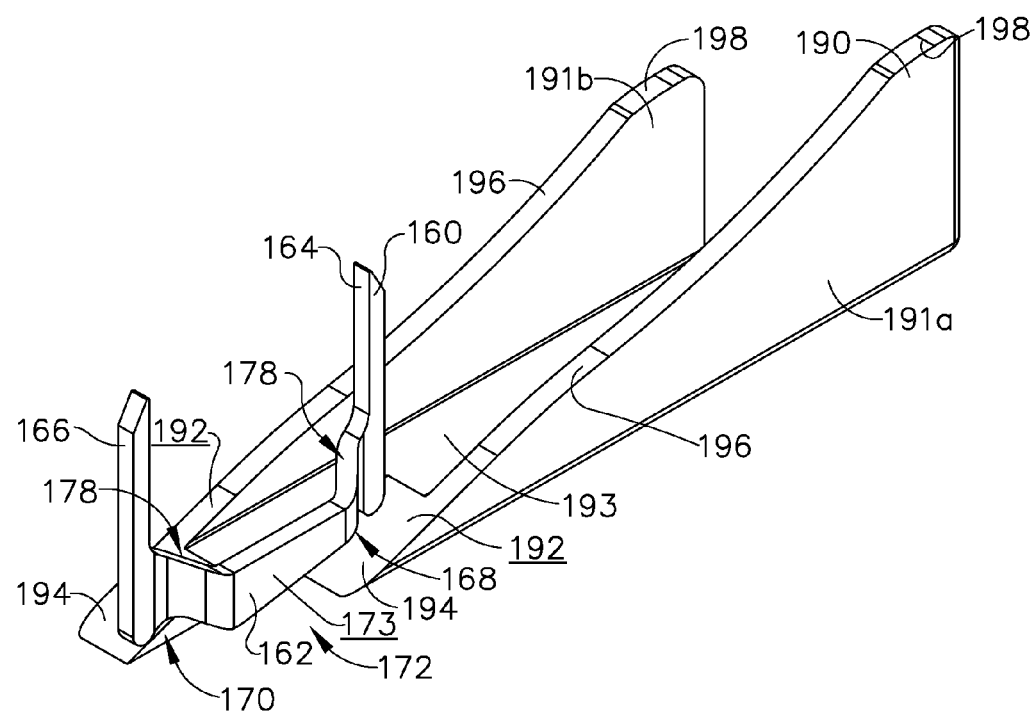
FIG. 15 is a perspective view of the staple and the sled of FIG. 14, depicting the leading surface of the sled contacting the initial drive surface of the staple.
Figure 16:
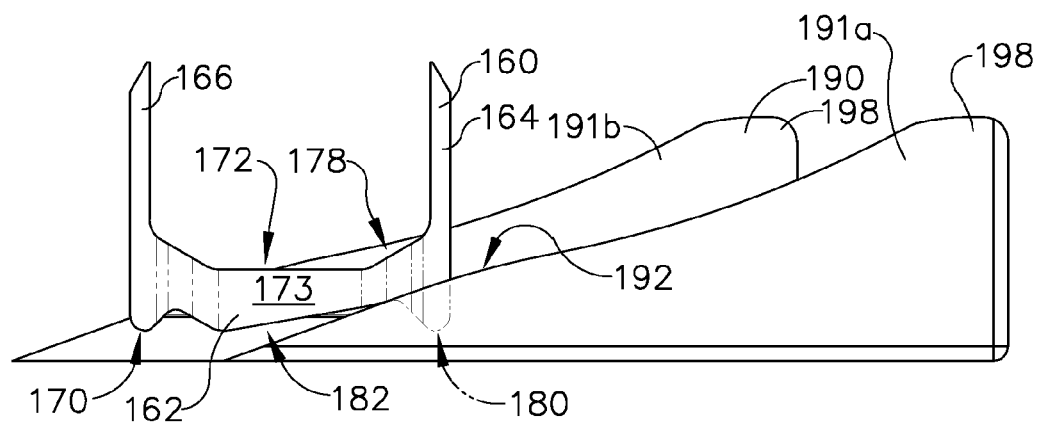
FIG. 16 is an elevation view of the staple and the sled of FIG. 14, depicting a trailing surface of the sled contacting a secondary drive surface of the staple, according to various embodiments of the present disclosure.
Figure 17:
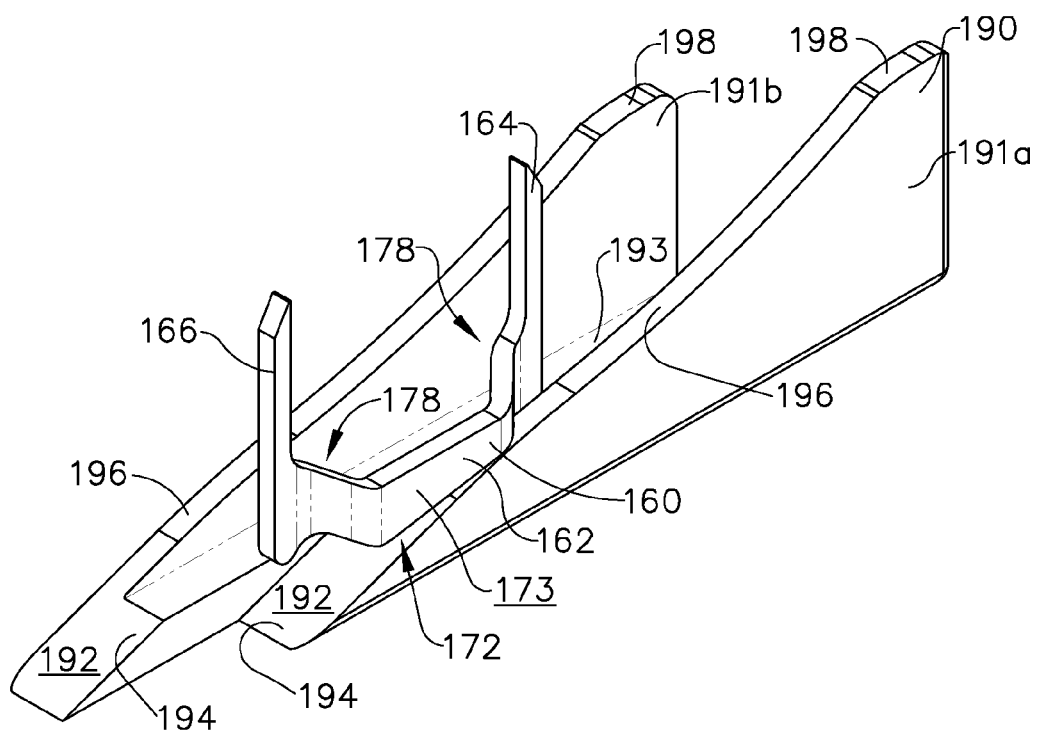
FIG. 17 is a perspective view of the staple and the sled of FIG. 14, depicting the trailing surface of the sled contacting the secondary drive surface of the staple.

Referring still to FIGS. 14-17, the sled 190 can include at least one lateral portion 191a, 191b. For example, the sled 190 can include a single lateral portion, a pair of lateral portions, and/or more than two lateral portions. In various instances, each lateral portion 191a, 191b can correspond to a row of staples 160 removably positioned in the cartridge body 142. As further depicted in FIGS. 14-17, the lateral portions 191a, 191b can be longitudinally staggered. For example, in certain embodiments, the first lateral portion 191a can lag behind or follow the second lateral portion 191b by a length of distance L (FIGS. 14 and 16). In other embodiments, the lateral portions 191a, 191b can be longitudinally aligned and/or the second lateral portion 191b can lag or follow the first lateral portion 191a, for example. In embodiments where the sled 190 comprises multiple lateral portions 191a, 191b, an intermediate portion 193 can connect and/or bridge the lateral portions 191a, 191b, for example.

Referring primarily to FIGS. 14-17, the sled 190 can transfer between the drive surfaces 180, 182 of the staple 160. Stated differently, the sled 190 can exert a driving force on the initial driving surface 180 of the staple 160, for example, and can then transition to exert a driving force on the second, or secondary, driving surface 182 of the staple 160. In certain embodiments, the sled ramp 192 can include a leading surface 194 and a trailing surface 196. The leading surface 194 can be adjacent to and/or connected to the trailing surface 196, for example, and the staple 160 can smoothly transition between the leading surface 194 and the trailing surface 196. For example, the leading surface 194 can contact the staple 160 and begin to lift the staple 160, and the trailing surface 196 can move into contact with the staple 160 and continue to lift the staple 160. In certain instances, the trailing surface 196 can smoothly lift the staple 160 out of and/or away from engagement with the leading surface 194, for example.

Referring still to FIGS. 14-17, the leading surface 194 can be aligned with the initial drive surface 180 and the trailing surface 196 can be aligned with the secondary drive surface 182, for example. In operation, the leading surface 194 of the ramp 192 can initially contact the staple 160. For example, referring to FIGS. 14 and 15, as the sled 190 translates, the leading surface 194 can contact the initial drive surface 180 of the staple 160. The inclined leading surface 194 can exert a driving force on the initial drive surface 180, which can begin to the lift the base 162 of the staple 160. For example, the staple 160 can be lifted a first distance or height by the leading surface 194. As the sled 190 continues to translate, referring now to FIGS. 16 and 17, the trailing surface 196 can move into contacting engagement with the secondary drive surface 182 of the staple 160, for example. The inclined trailing surface 196 can exert a driving force on the secondary drive surface 182, for example, which can continue to the lift the base 162 of the staple 160. For example, the staple 160 can be lifted a second distance or height by the trailing surface 194.

In various instances, the trailing surface 196 can lift the initial drive surface 180 away from and/or out of contact with the leading surface 194 of the ramp 192, for example. For example, the trailing surface 196 can contact the secondary drive surface 182 and immediately lift the staple 160 such that the primary drive surface 180 is moved out of driving contact with the leading surface 194. In other embodiments, the leading surface 194 can drive the initial drive surface 180 and the trailing surface 196 can drive the secondary drive surface simultaneously for at least a portion of the staple's deployment. As the sled 190 continues to translate, the trailing surface 196 can lift the base 162 out of the staple cavity 144 (FIGS. 4 and 5) and/or can eject the staple 160 from the cartridge 140 (FIGS. 4 and 5). For example, the proximal portion of the trailing surface 196 can include a sled overdrive 198. In various embodiments, the sled overdrive 198 can extend out of the staple cavity 144 and can lift the staple overdrive 188, i.e., the lowest portion of the intermediate portion 172 of the base 162 (see FIG. 7), out of the staple cavity 144.

Deployment of multiple staples 160 according to an exemplary application of the present disclosure is depicted in FIGS. 18-21. In certain embodiments, multiple rows of staple cavities 144 can be defined in the cartridge body 142. For example, multiple rows of staple cavities 144 can be defined on a first side of the cartridge slot 143 (FIG. 3), and multiple rows of staple cavities 144 can be defined on a second side of the cartridge slot 143. FIGS. 18-21 depict two rows of staples 160 positioned in two rows of staples cavities 144 in the cartridge body 142. Referring still to FIGS. 18-21, the staples 160a, 160c, and 160e can be positioned in a more inner row of staple cavities 144, for example, and the staples 160b, 160d, and 160f can be positioned in a more outer row of staple cavities 144, for example. In various embodiments, the first inner staple 160a can be positioned nearer to the cartridge slot 143 than the first outer staple 160b. For example, the first inner staple 160a can be adjacent to the cartridge slot 143, and the first outer staple 160b can be intermediate the first inner staple 160a and the side of the cartridge body 142, for example. In various embodiments, additional rows of staples 160 can be defined in the cartridge body 142. For example, at least one row of staples can be positioned intermediate the first staple 160a and the cartridge slot 143, and/or at least one row of staples 160 can be positioned intermediate the first outer staple 160b and the side of the cartridge body 142, for example.

Figure 18:
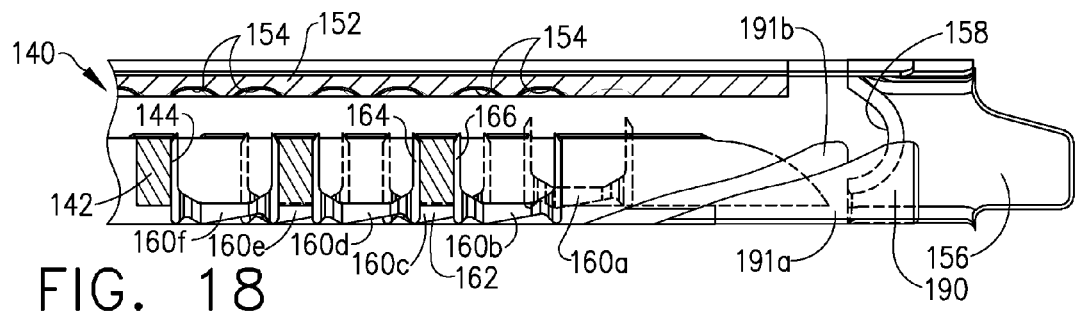
FIGS. 18-21 are cross-sectional elevation views of the end effector of FIG. 3, depicting a firing progression of staples from the staple cartridge, according to various embodiments of the present disclosure.
Figure 19:
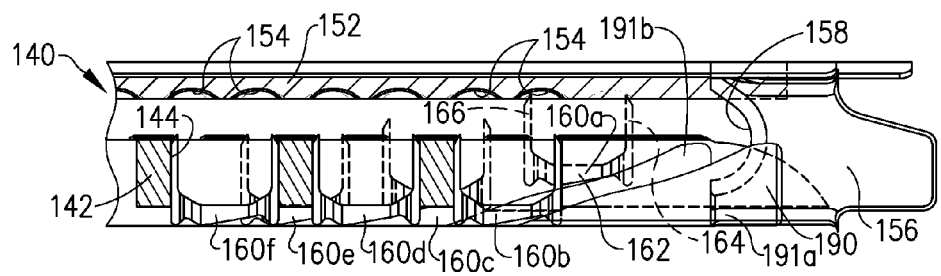

Referring primarily to FIG. 18, as the sled 190 moves distally, the second lateral portion 191b can contact the first inner staple 160a. The leading surface 194 (FIGS. 14-17) of the second lateral portion 191b can begin to lift the first inner staple 160a, for example. Referring now to FIG. 19, as the sled 190 continues to move distally, the trailing surface 196 (FIGS. 14-17) of the second lateral portion 191b can continue to lift the first inner staple 160a, and can move the first inner staple 160a into forming contact with the anvil 152 of the end effector 120, for example. Additionally, the leading surface 194 of the second lateral portion 191b can move into contact with the second inner staple 160c, for example. In various instances, the first lateral portion 191a can move into contact with the first outer staple 160b at the same time that the second lateral portion 191b moves into contact with the second inner staple 160c, for example. In certain embodiments, the longitudinal lag or offset between the first lateral portion 191a and the second lateral portion 191b can correspond to the longitudinal distance between the first outer staple 160b and the second inner staple 160c. For example, the first lateral portion 191a can lag behind the second lateral portion 191b a length L (FIGS. 14 and 16), and the first outer staple 160b can be longitudinally offset from the second inner staple 160c by the length L. In such embodiments, deployment of the first outer staple 160b and the second inner staple 160c can be simultaneous and/or synchronized, for example.

Figure 20:
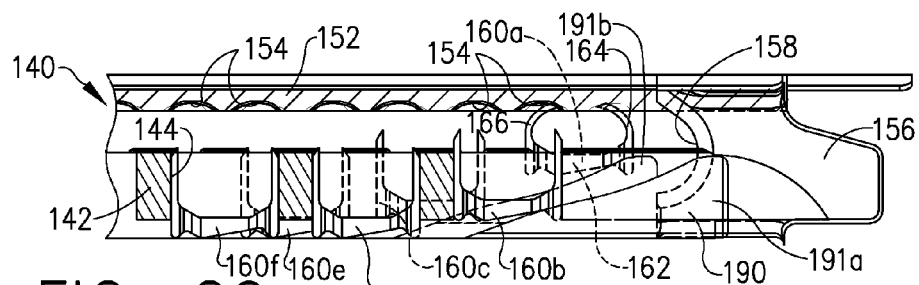
Figure 21:
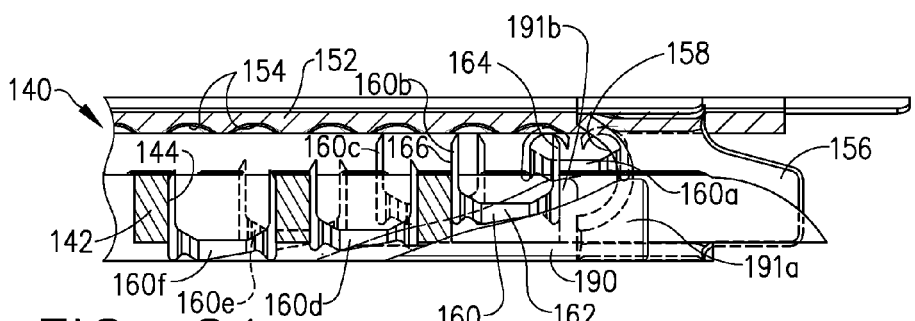

Referring now to FIG. 20, as the sled 190 continues to progress, the trailing surface 196 of the second lateral portion 191b can continue to lift the first inner staple 160a toward the anvil 152. The staple forming pockets 154 defined in the anvil 152 can catch the staple legs 164, 166, and can deform the first inner staple 160a. Furthermore, the second lateral portion 191b can continue to lift the second inner staple 160c, and the first lateral portion 191a can continue to lift the first outer staple 160b, for example. Referring now to FIG. 21, as the sled 190 continues to move distally, the second lateral portion 191b can eject the first inner staple 160a from the staple cavity 144. In various instances, the sled overdrive 198 (FIGS. 14-17), can lift the staple overdrive 188 to clear the staple base 162 over the cartridge body 142, for example. As the staple forming pockets 154 of the anvil 124 continue to form the first inner staple 160a, the second lateral portion 191b can continue to lift the second inner staple 160c, for example, and the first lateral portion 191a can continue to lift the first outer staple 160b. Additionally, the second lateral portion 191b can move into contact with the third inner staple 160e, for example, and the first lateral portion 191a can move into contact with the second outer staple 160d, for example. In various instances, similar to the above, the second outer staple 160d can be longitudinally offset from the third inner staple 160e by the length L (FIGS. 14 and 16).

As described herein, the staples 160 can be sequentially fired from the cartridge 140. For example, as the sled 190 moves distally, the sled 190 can sequentially fire staples 160 from a proximal portion of the cartridge body 142 toward a distal portion of the cartridge body 142. As described herein, the sled 190 can fire a first, more proximal, inner staple 160a before firing a second, more distal, inner staple 160c. In other embodiments, the sled 190 may translate proximally to fire staples 160 from a staple cartridge. In such embodiments, the sled 190 can sequentially fire staples 160 from a distal portion of the staple cartridge 140 toward a proximal portion of the staple cartridge 140. Moreover, firing of the staples 160 from the staple cartridge 140 can be paced or synchronized. For example, the first outer staple 160b and the second inner staple 160c can be fired simultaneously, and/or the second outer staple 160d and the third inner staple 160e can be fired simultaneously, for example. For example, the longitudinal offset between the first lateral portion 191a of the sled 190 and the second lateral portion 191b of the sled 190 can correspond to the longitudinal distance between a staple 160 in a first row of staple cavities and a staple 160 in a second, different row of staple cavities. In such embodiments, deployment of the staples 160 can be timed such that a staple 160 in the first row of staple cavities is fired at the same time as a staple 160 in the second row of staple cavities. The timing or pacing of staple deployment can improve tissue positioning and/or placement during firing. For example, sections of the tissue can be held in position by the end effector jaws 123, 124 (FIG. 3), and the sections can be stapled simultaneously. In other instances though, the offset between 191a and 191b may not be the same as the offset between the staples in the staple rows.

Figure 22:
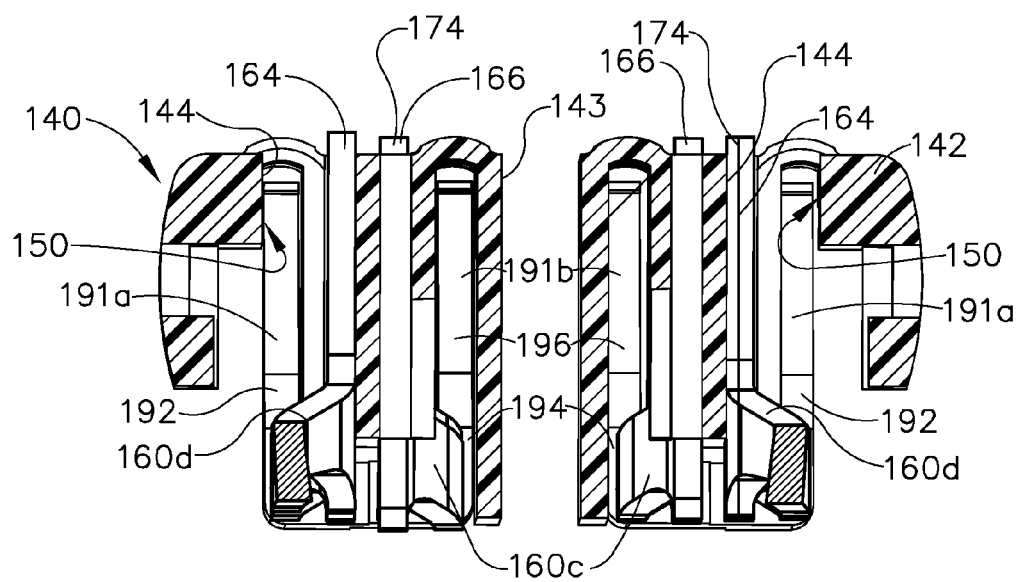
FIG. 22 is a cross-sectional elevation view of the staple cartridge and the sleds of FIG. 3, depicting the staples in unfired positions, according to various embodiments of the present disclosure.
Figure 23:
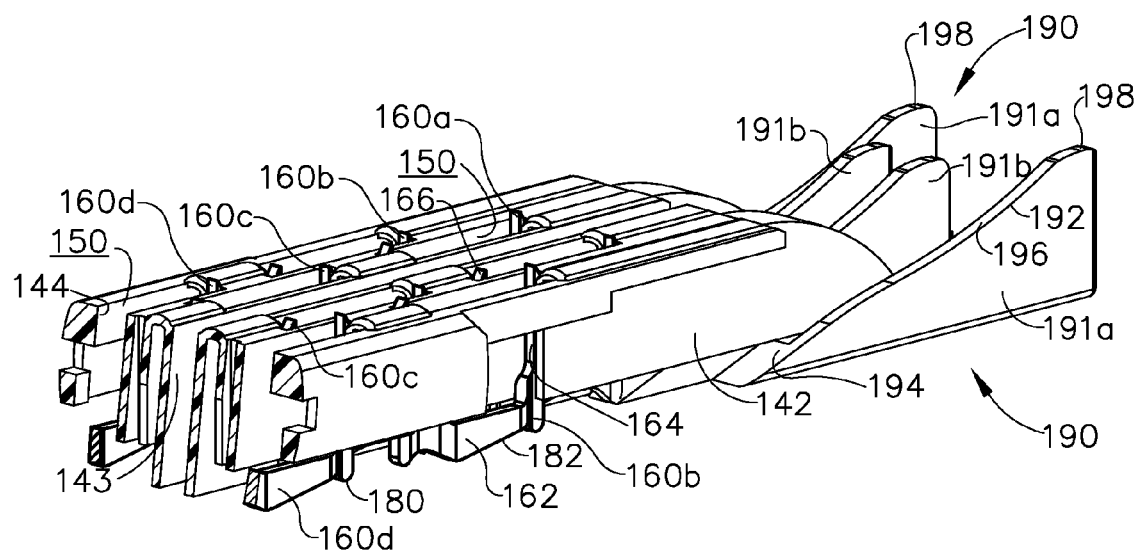
FIG. 23 is a cross-sectional perspective view of the cartridge and the sleds of FIG. 22, depicting the staples in the unfired positions depicted in FIG. 22.

An exemplary embodiment of staple deployment is further illustrated in FIGS. 22-31. For example, the staples 160a, 160b, 160c, and 160d can be positioned on both sides of the cartridge slot 140, and can be ejectably positioned in staple cavities 144 defined in the cartridge body 142. Referring primarily to FIGS. 22 and 23, the staples 160a, 160b, 160c, and 160d can be unfired, and the sleds 190 can be positioned proximal to the cartridge body 142. The sleds 190 can be aligned with the rows of staple cavities 144 in the cartridge body 142. For example, a first sled 190 can be aligned with the staples 160a, 160c in the first inner row of staple cavities 144 and with the staples 160b, 160d in the first outer row of staple cavities 144, and a second sled 190 can be aligned with the staples 160a, 160c in the second inner row of staple cavities 144 and with the staples 160b, 160d in the second outer row of staple cavities 144. The first lateral portions 191a of each sled 190 can be aligned with the outer staples 160b, 160d, and the second lateral portions 191b of each sled 190 can be aligned with the inner staples 160a, 160c, for example.

Figure 24:
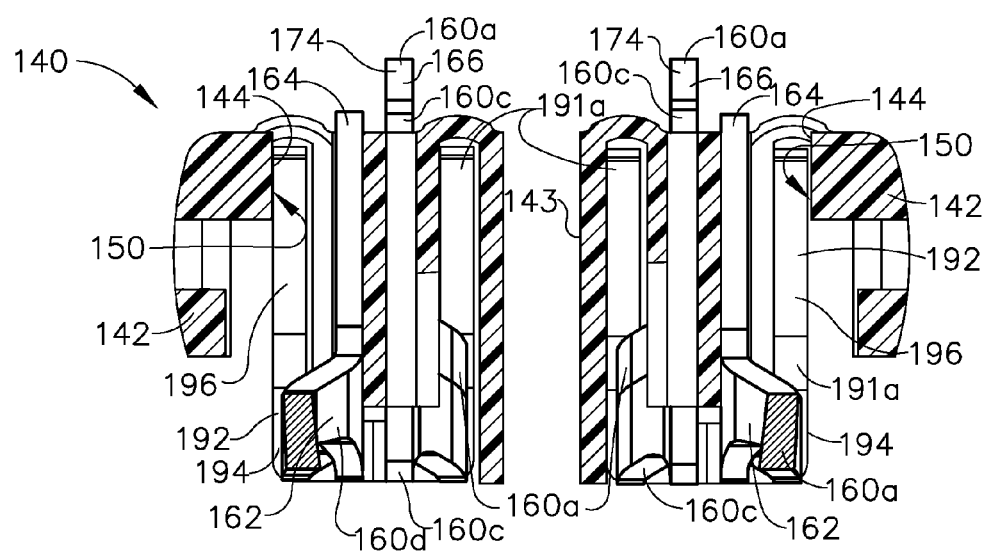
FIG. 24 is a cross-sectional elevation view of the cartridge and the sleds of FIG. 22, depicting a proximal pair of staples in partially fired positions and the remaining staples in unfired positions, according to various embodiments of the present disclosure.
Figure 25:
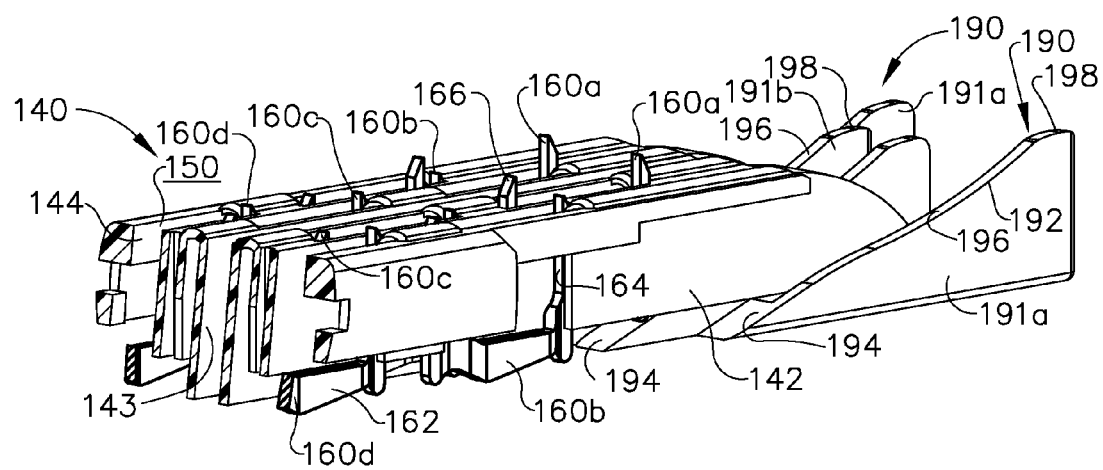
FIG. 25 is a cross-sectional perspective view of the cartridge and the sleds of FIG. 22, depicting the proximal pair of staples in the partially fired positions depicted in FIG. 24 and the remaining staples in the unfired positions depicted in FIG. 24.

Referring primarily to FIGS. 24 and 25, the first inner staples 160a can be moved or lifted to partially fired positions relative to the cartridge body 142. For example, the second lateral portions 191b of each sled 190 can move into engagement with the first inner staples 160a. The leading surfaces 194 of the second lateral portions 191b can lift the first inner staples 160a a first distance. Subsequently, the trailing surfaces 196 can move into engagement with the first inner staples 160a to further lift the first inner staples 160a. In various embodiments, distal translation of the sleds 190 can be coordinated, and the first inner staples 160a on each side of the slot 143 can be fired simultaneously, for example. As the first inner staples 160a are lifted, a portion of each staple 160a can slide or move against a longitudinal guide surface 150 of the staple cavity 144, and the longitudinal guide surface 150 can support and/or balance the torque generated by the sled 190, as described in greater detail herein.

Figure 26:
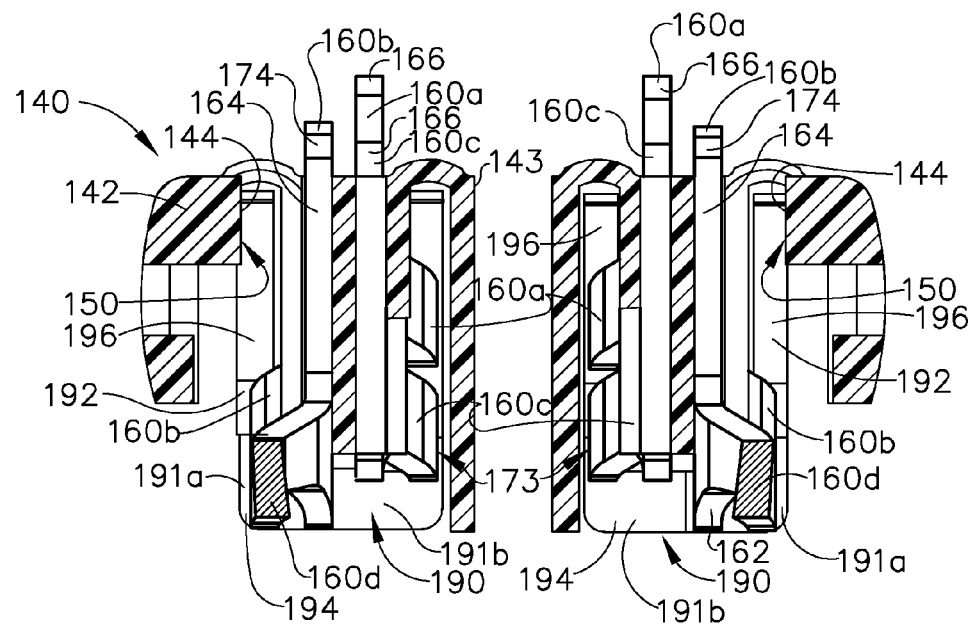
FIG. 26 is a cross-sectional elevation view of the cartridge and the sleds of FIG. 22, depicting multiple pairs of staples in partially fired positions and the proximal pair of staples in partially deformed configurations, according to various embodiments of the present disclosure.
Figure 27:
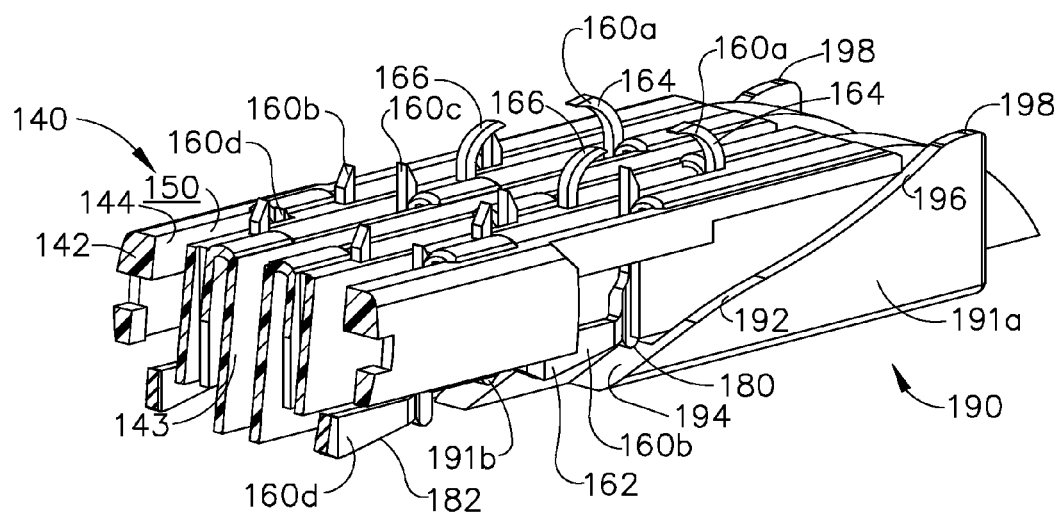
FIG. 27 is a cross-sectional perspective view of the cartridge and the sleds of FIG. 22, depicting the multiple pairs of staples in the partially fired positions of FIG. 26 and the proximal pair of staples in the partially deformed configurations depicted in FIG. 26.

Referring now to FIGS. 26 and 27, as the sleds 190 continue to translate relative to the cartridge 140, the sleds 190 can move into engagement with the first outer staples 160b and the second inner staples 160c. In various instances, the sleds 190 can contact the first outer staples 160b and the second inner staples 160c simultaneously. For example, the first lateral portions 191a of sleds 190 can contact the first outer staples 160b as the second lateral portions 191b of the sleds 190 contact the second inner staples 160c, for example. Referring primarily to FIG. 27, the leading surfaces 194 of the first lateral portions 191a and the second lateral portions 191b of the sleds 190 can engage the initial drive surfaces 180 of the staples 160b, 160c, and can lift the staples 160b, 160c relative to the cartridge body 142. Additionally, the trailing surfaces 196 of the second lateral portions 191b of the sleds 190 can continue to lift the first inner staples 160a, for example. As the first inner staples 160a continue to move out of the staple cavities 144, an anvil 152 (FIGS. 18-21) can begin to deform the first inner staples 160a. For example, staple forming pockets 154 (FIGS. 18-21) can catch, turn and/or bend the legs 164, 166 of the first inner staples 160a. As described herein, the anvil 152 can deform the staples 160a into modified "B-forms", for example.

Figure 28:
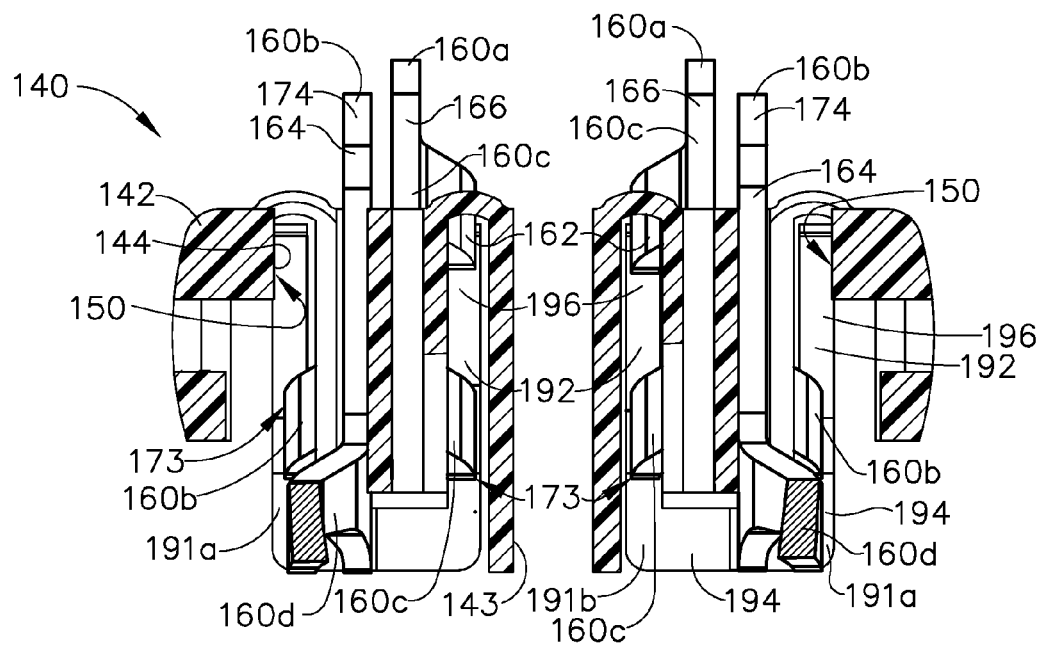
FIG. 28 is a cross-sectional elevation view of the cartridge and the sleds of FIG. 22, depicting multiple pairs of staples in further fired positions and the proximal pair of staples in further deformed configurations, according to various embodiments of the present disclosure.
Figure 29:
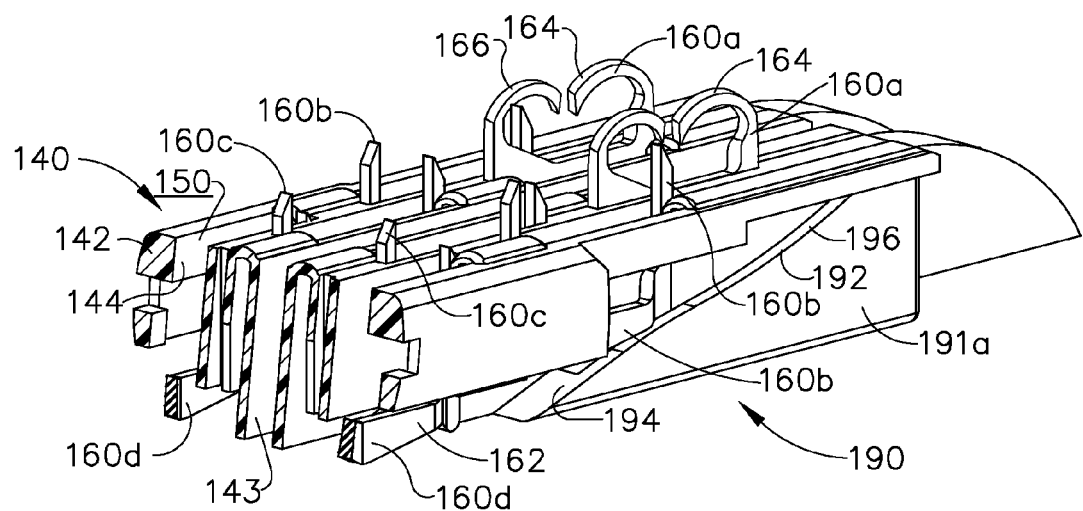
FIG. 29 is a cross-sectional perspective view of the cartridge and the sleds of FIG. 22, depicting the multiple pairs of staples in the partially fired positions depicted in FIG. 28 and the proximal pair of staples in the partially deformed configurations depicted in FIG. 28.

Referring now to FIGS. 28 and 29, as the sleds 190 continue to translate relative to the staple cartridge 140, the second lateral portions 191b of the sleds 190 can continue to lift the first inner staples 160a, for example, and the anvil 152 (FIGS. 18-21) can continue to deform the first inner staples 160a, for example. In various instances, the sleds 190 can also continue to lift the first outer staples 160b and the second inner staples 160c. For example, the trailing surfaces 196 of the sleds 190 can move into engagement with the secondary drive surfaces 182 of the first outer staples 160b and the second inner staples 160c, and can lift the staple bases 162 upward, for example, such that the staples legs 164, 166 continue to move out of the cartridge body 142.

Figure 30:
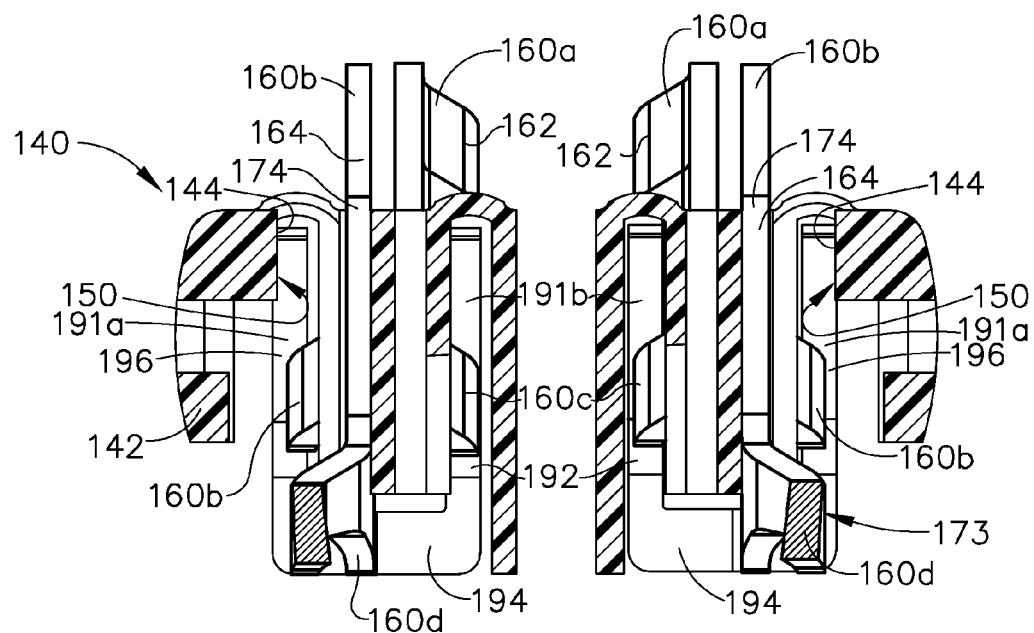
FIG. 30 is a cross-sectional elevation view of the cartridge and the sleds of FIG. 22, depicting multiple pairs of staples in partially fired positions and in partially deformed configurations and the proximal pair of staples in ejected positions and in fully deformed configurations, according to various embodiments of the present disclosure.
Figure 31:
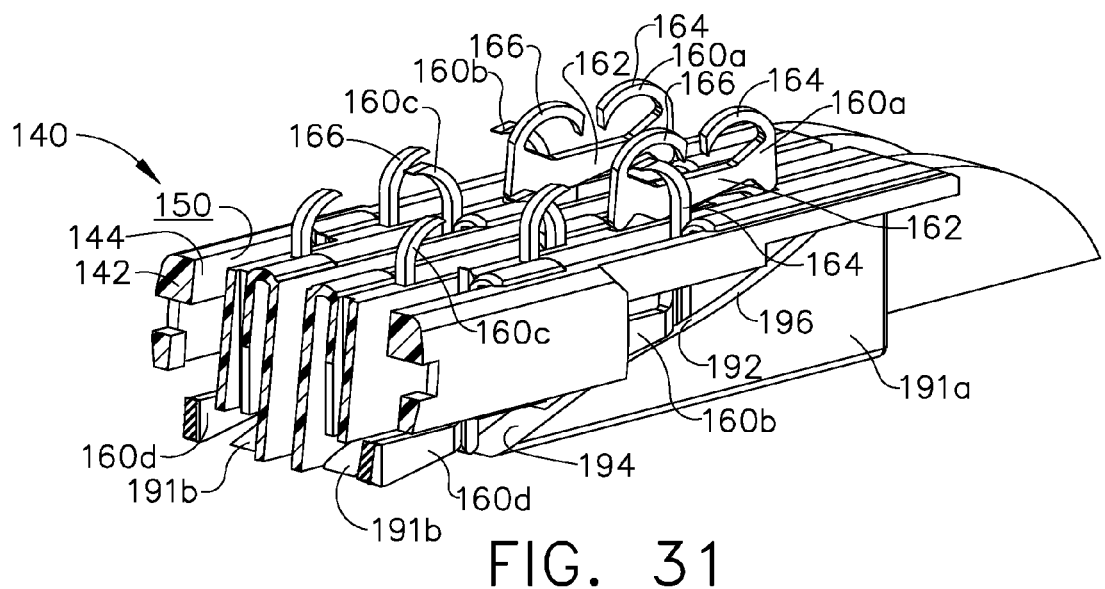
FIG. 31 is a cross-sectional perspective view of the cartridge and the sleds of FIG. 22, depicting the multiple pairs of staples in the partially fired positions and in the partially deformed configurations depicted in FIG. 30 and the proximal pair of staples in the ejected positions and in the fully deformed configurations depicted in FIG. 30.
Figure 34:
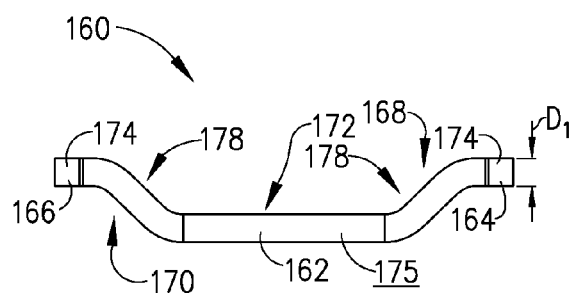
FIG. 34 is a plan view of the staple of FIG. 33.
Figure 33:
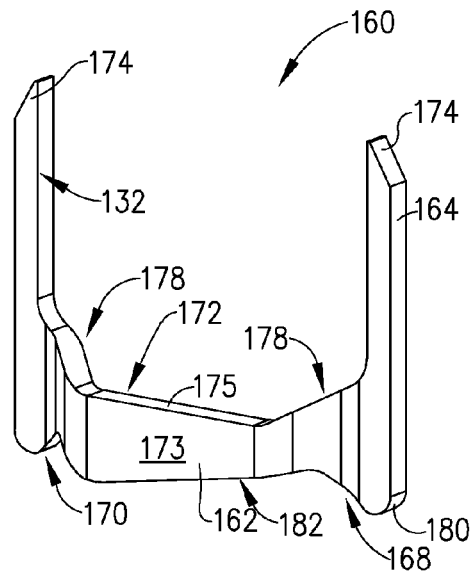
FIG. 33 is a perspective view of the staple formed from the method depicted in FIGS. 32A-32C, according to various embodiments of the present disclosure.
Figure 35:
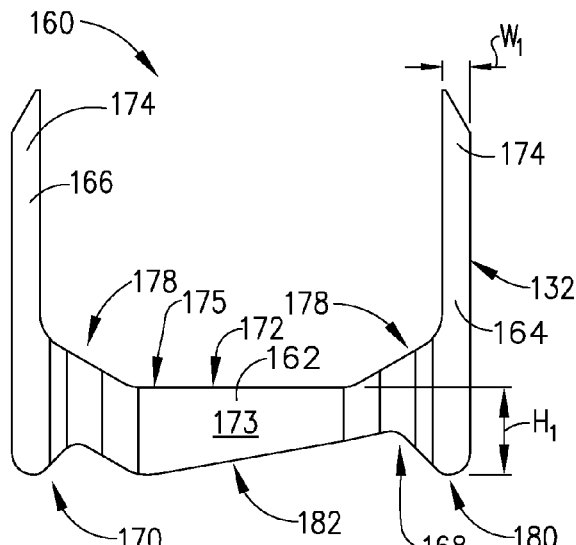
FIG. 35 is a front elevation view of the staple of FIG. 33.
Figure 36:
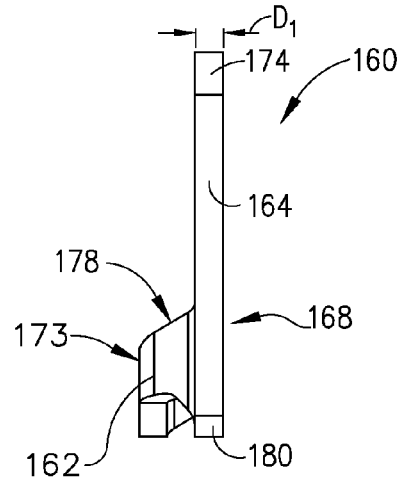
FIG. 36 is a side elevation view of the staple of FIG. 33.
Figure 38:
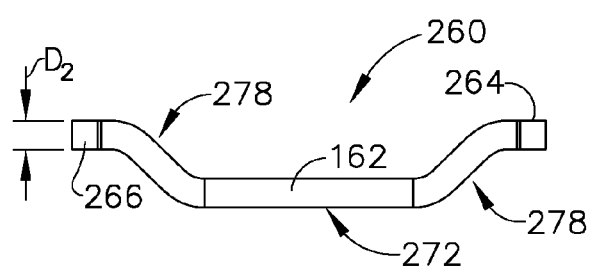
FIG. 38 is a plan view of the staple of FIG. 37.
Figure 37:
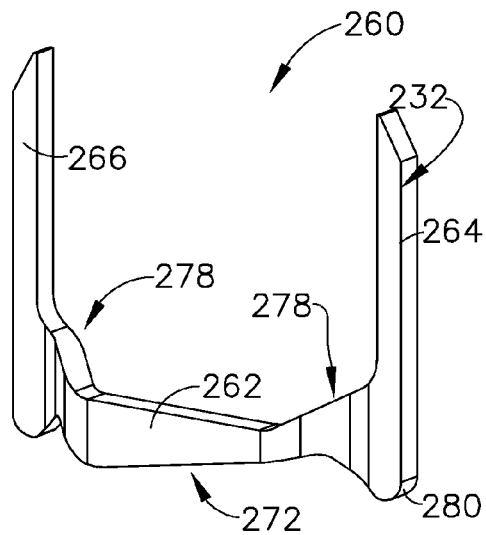
FIG. 37 is a perspective view of a staple according to various embodiments of the present disclosure.
Figure 39:
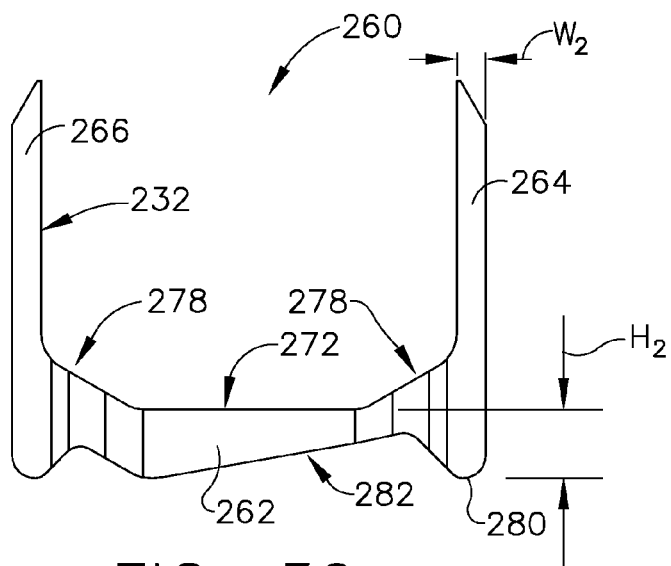
FIG. 39 is a front elevation view of the staple of FIG. 37.
Figure 40:
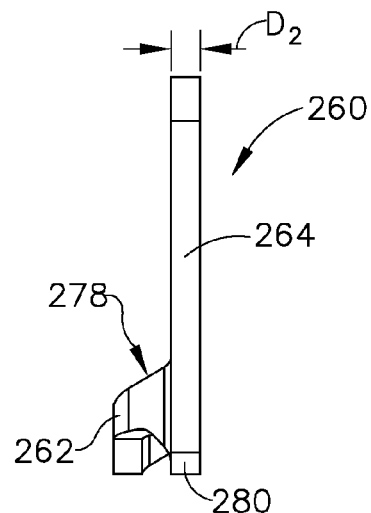
FIG. 40 is a side elevation view of the staple of FIG. 37.

Referring now to FIGS. 30 and 31, as the sleds 190 continue to translate relative to the cartridge 140, the second lateral portions 191b of the sleds 190 can continue to simultaneously lift the first inner staples 160a. For example, the sled overdrives 198 (FIGS. 16 and 17), can lift the first inner staples 160a entirely out of the cartridge body 142, such that the first inner staples 160a are entirely ejected from the staple cartridge 140. In various instances, the anvil 152 (FIGS. 18-21) can continue to deform the first inner staples 160a, for example, and the first inner staples 160a can be fully deformed when lifted entirely out of the cartridge body 142. Additionally, the trailing surfaces 196 of the sleds 190 can also continue to simultaneously lift the first outer staples 160b and the second inner staples 160c. For example, the trailing surfaces 196 of the first lateral portions 191a can lift or drive the first outer staples 160b, and the trailing surfaces 196 of the second lateral portions 191b can lift or drive the second inner staples 160c, for example. Moreover, as the first outer staples 160b and the second inner staples 160c continue to move out of the staple cavities 144, the anvil 152 (FIGS. 18-21) can begin to deform the first outer staples 160b and the second inner staples 160c. For example, staple forming pockets 154 (FIGS. 18-21) can catch, turn and/or bend the legs 164, 166 of the first outer staples 160b and the second inner staples 160c. In various instances, the sleds 190 can continue to translate relative to the cartridge body 142, and the first and second lateral portions 191a, 191b of the sleds 190 can continue to pace and/or time the deployment of the staples 160 from adjacent and/or neighboring staple rows. The sleds 190 can sequentially fire staples 160 from the proximal portion of the staple cartridge 140 to the distal portion of the staple cartridge 140. In other embodiments, the sleds 190 can move proximally, and can fire staples 160 from the distal portion of the staple cartridge 140 toward a proximal portion of the staple cartridge 140, for example. Moreover, in certain instances, the spacing between the staples and the lateral sled portions can affect non-synchronized deployment of the staples, for example.

Figure 56:
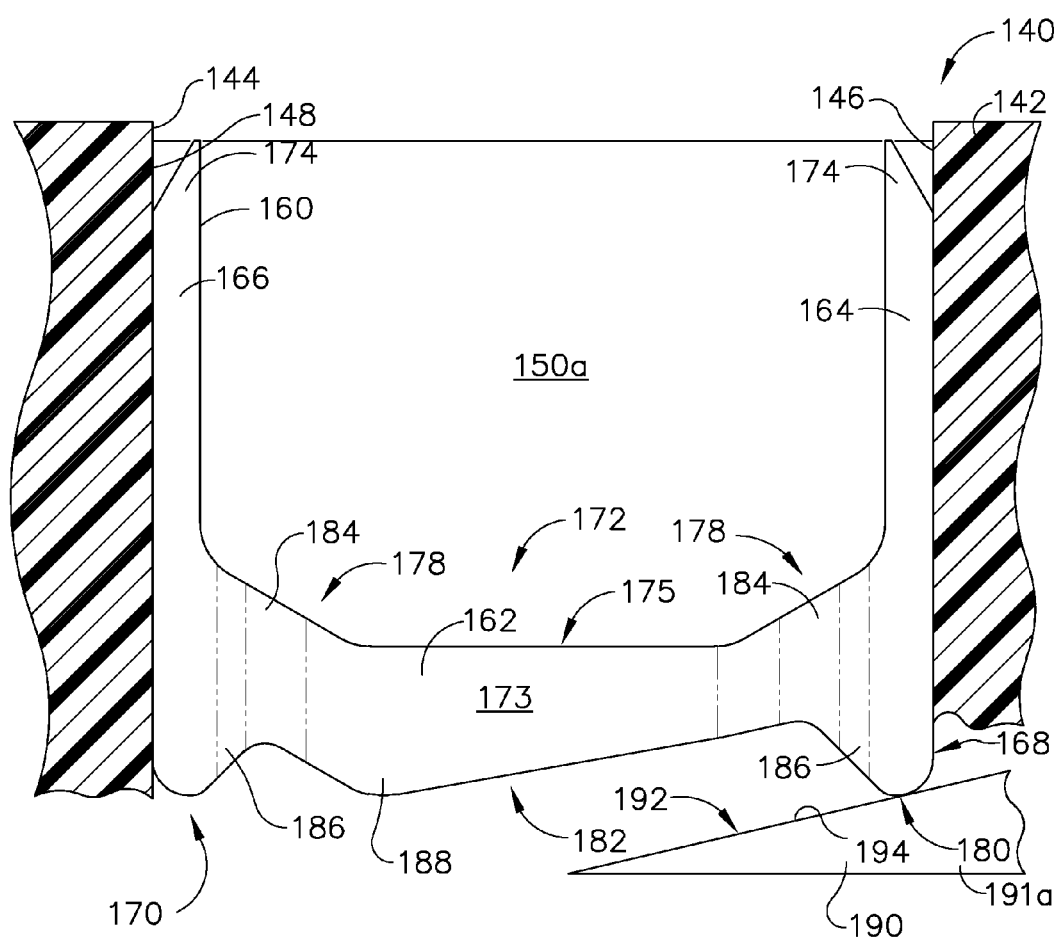
FIG. 56 is a partial, cross-sectional elevation view of the staple cartridge of FIG. 4, depicting a staple in a partially-fired position in a staple cavity, according to various embodiments of the present disclosure.
Figure 57:
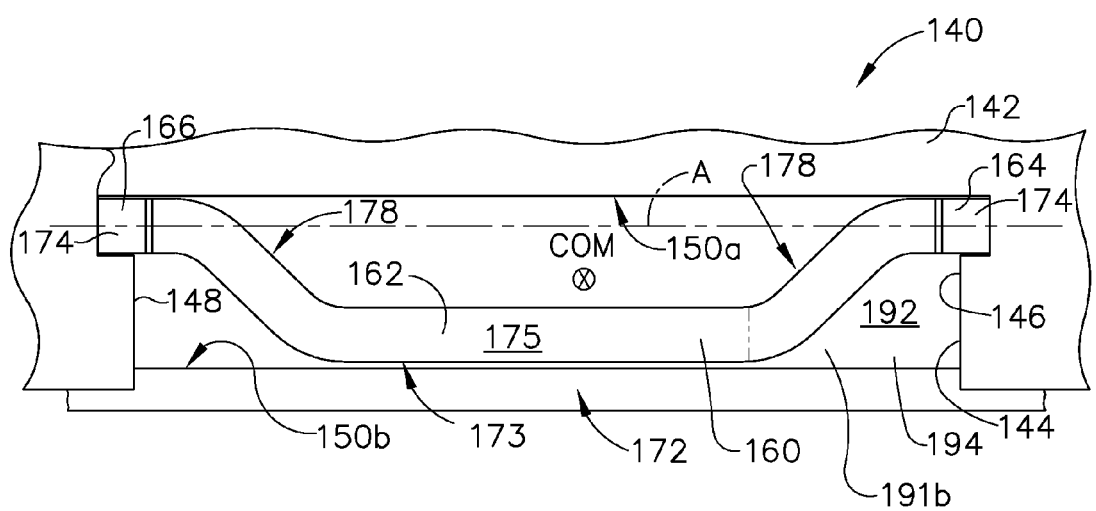
FIG. 57 is a partial plan view of the staple cartridge of FIG. 56, depicting the staple in the partially-fired position depicted in FIG. 56.
Figure 58:
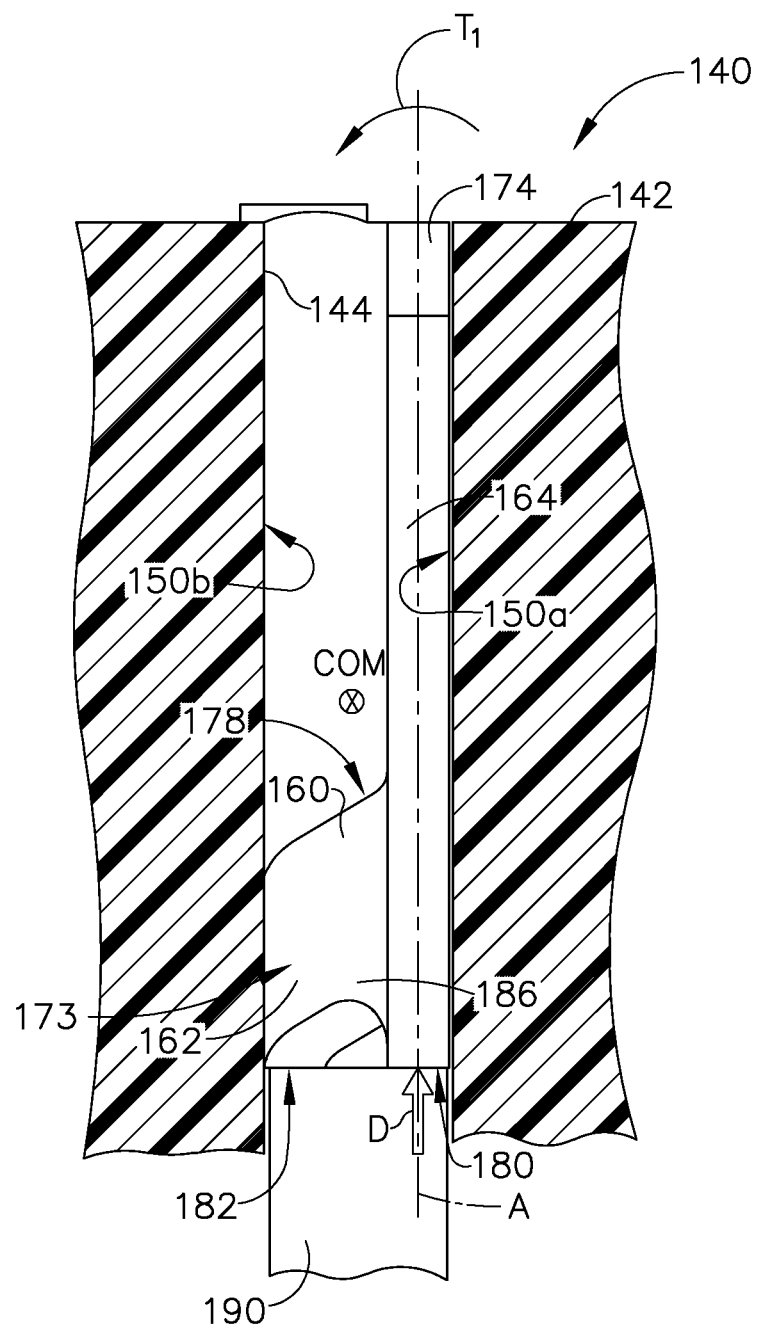
FIG. 58 is a partial, cross-sectional elevation view of the staple cartridge of FIG. 56, depicting the staple in the partially-fired position depicted in FIG. 56.

Referring now to FIGS. 56-64, in various instances, the staple cavity 144 can guide the staple 160 as the sled 190 moves the staple 160 through a firing progression. For example, in various instances, the leading surface 194 of the sled 190 can contact the initial drive surface 180 of the staple 160, and can exert a driving force $D_1$ (FIG. 58) on the staple 160 via the initial drive surface 180 (FIGS. 56-58). The leading surface 194 can lift the staple 160 upward along a plane defined by axis E (FIG. 57) and axis F (FIG. 58). As indicated in FIGS. 57 and 58, the staple's center of mass (COM) can be offset from the axes E and F and, in such embodiments, the driving force $D_1$ (FIG. 58) exerted on the initial drive surface 180 in the plane defined by axes E and F can generate a torque $T_1$ (FIG. 58). As described in greater detail herein, the staple cavity 144 can include a longitudinal sidewall 150 between the proximal end 146 and the distal end 148 of the staple cavity 144. In certain embodiments, the staple cavity 144 can include a first sidewall 150a and a second sidewall 150b. Moreover, as described herein, the sidewalls 150a, 150b can resist torsion of the staple 160 during firing. For example, when the leading surface 194 of the sled 190 drives the initial drive surface 180 of the staple 160 along the plane defined by axes E and F, the second sidewall 150b can resist the counterclockwise torque $T_1$ (FIG. 58) corresponding to the driving force $D_1$ generated by the sled 190. As the staple 160 is lifted a first distance by the leading surface 194 of the sled 190, the second sidewall 150b can guide and support the intermediate portion 172 of the staple base 162. For example, the flat surface 173 of the intermediate portion 172 of the staple base 162 can slide along and/or move against the second sidewall 150b.

Figure 59:
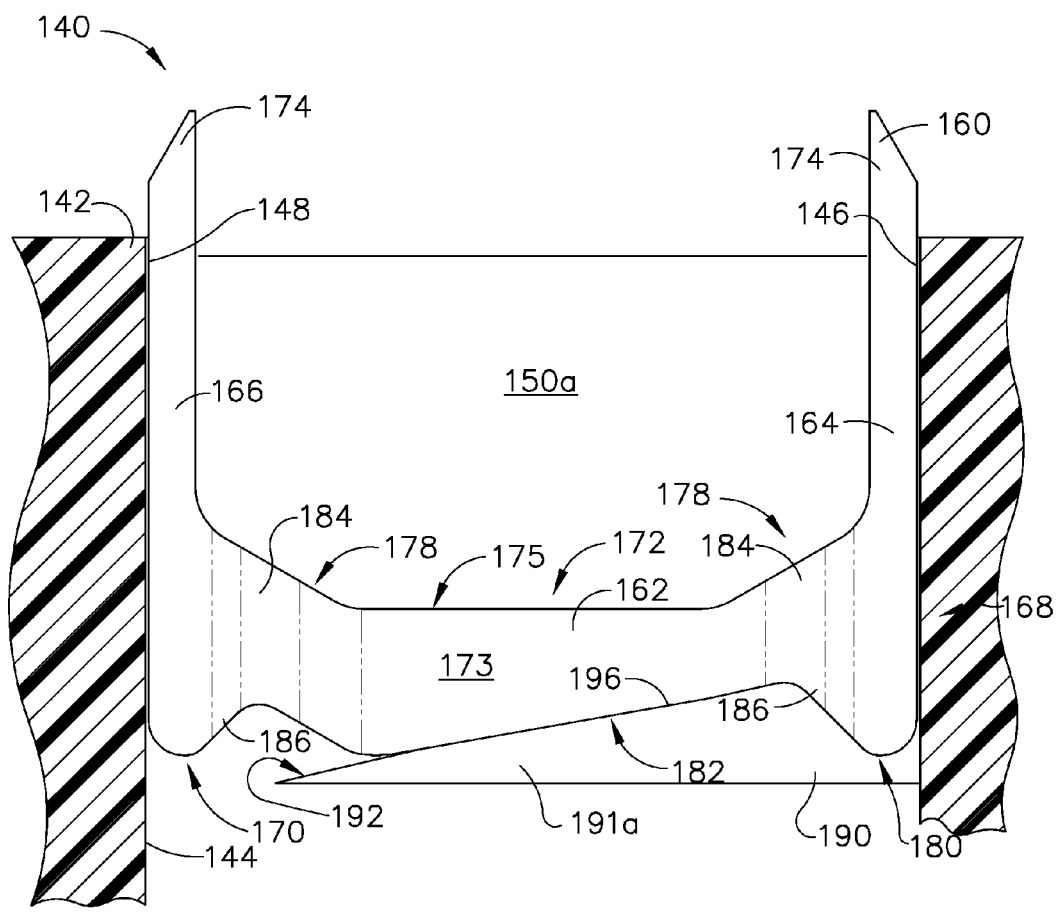
FIG. 59 is a partial, cross-sectional elevation view of the staple cartridge of FIG. 56, depicting the staple in another partially-fired position, according to various embodiments of the present disclosure.
Figure 60:
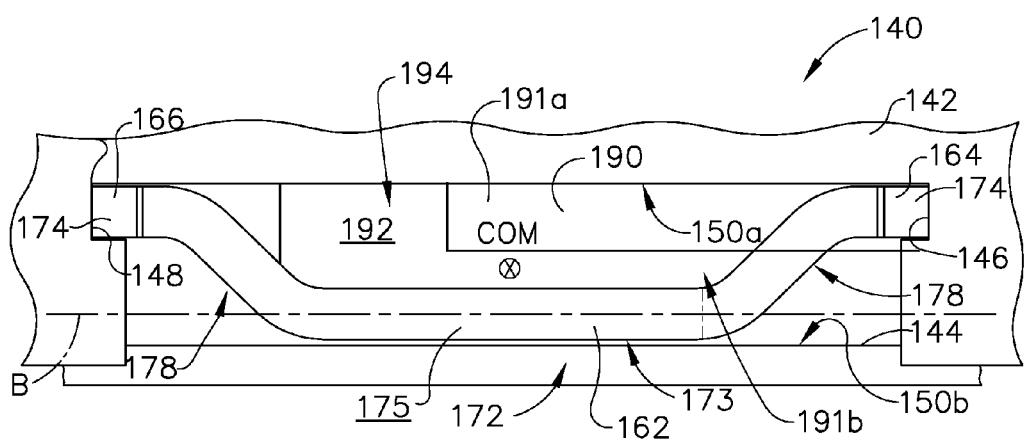
FIG. 60 is a partial, plan view of the staple cartridge of FIG. 56, depicting the staple in the partially-fired position depicted in FIG. 59.
Figure 61:
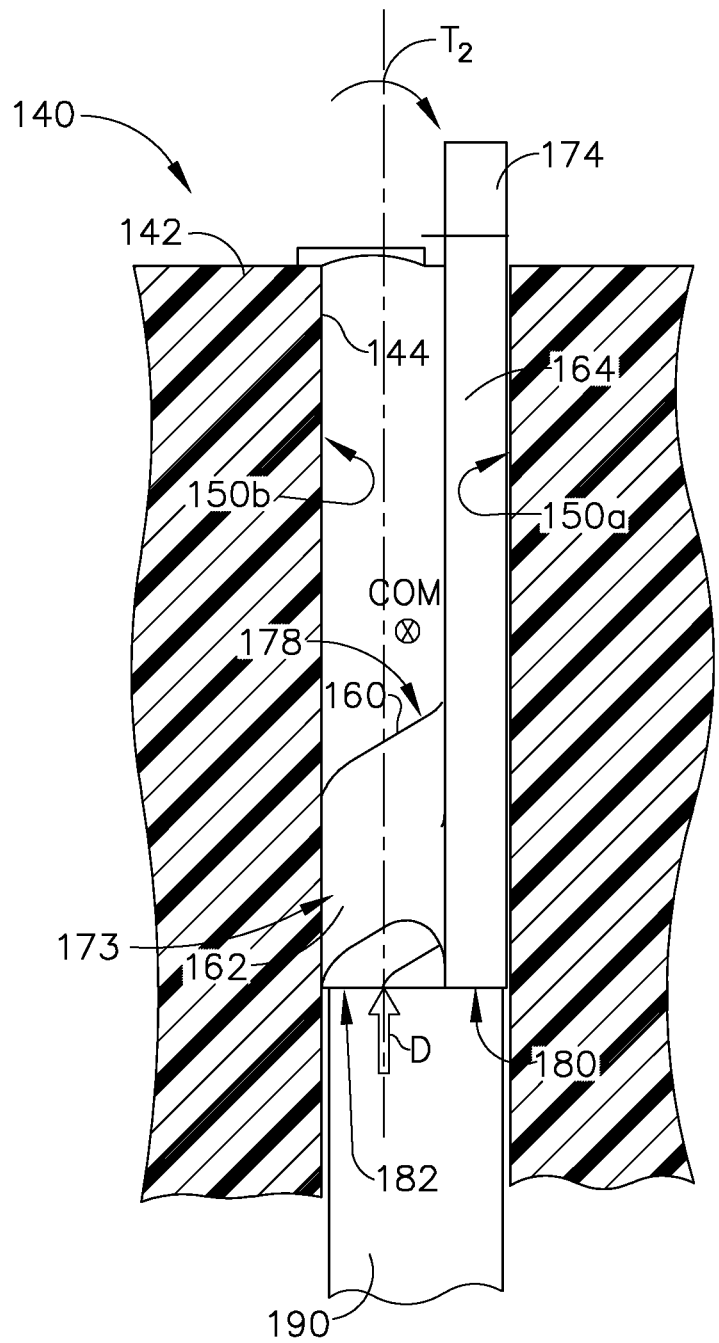
FIG. 61 is a partial, cross-sectional elevation view of the staple cartridge of FIG. 56, depicting the staple in the partially-fired position depicted in FIG. 59.

Referring now to FIGS. 59-61, when the sled 190 transitions between the initial drive surface 180 and the secondary drive surface 182, as described herein, the trailing surface 196 of the sled 190 can exert a driving force $D_2$ (FIG. 61) on the staple 160 via the secondary drive surface 182. In various instances, the trailing surface 196 of the sled 190 can lift the base 162 of the staple 160 upward along a plane defined by axis I (FIG. 60) and axis J (FIG. 61). As indicated in FIGS. 60 and 61, the staple's center of mass (COM) can be offset from the plane defined by axes I and J and, in such embodiments, the driving force $D_2$ (FIG. 61) exerted on the secondary drive surface 182 by the trailing surface 196 of the sled 190 can generate a torque $T_2$ (FIG. 61). Upon comparing FIGS. 58 and 61, it can be seen that the driving force $D_1$ is applied to the staple 160 on a first side of the COM and the driving force $D_2$ is applied on the opposite side of the COM. In various instances, the torque $T_1$ can be in a first direction, and the torque $T_2$ can be in second direction, and the second direction can be opposite to the first direction, for example. When the trailing surface 196 drives the secondary drive surface 182 of the staple 160 along the plane defined by axes I and J, the first sidewall 150a can resist the clockwise torque $T_2$ (FIG. 61). As the staple 160 is lifted the second distance by the trailing surface 194, the first sidewall 150a can guide and support the proximal and distal ends 168, 170 of the staple base 162. For example, the proximal and distal ends 168, 170 of the base 162 can slide along and/or move against the first sidewall 150a.

The reader will appreciate that, in certain embodiments, various staples and/or features thereof, which are described herein with respect to the staple's COM, can be similarly applicable to the staple's center of geometry. In various instances, a staple, such as staple 160, for example, can comprise a single material and/or can have a uniform composition. In such embodiments, the COM of the staple can correspond to the center of geometry of the staple. In other embodiments, a staple can comprise multiple materials and/or a non-uniform composition. For example, the staple can be formed from multiple pieces and/or materials that have been welded and/or otherwise joined together. In certain embodiments, multiple sheets of at least two different materials can be welded together, for example, and the staple can be cut from a portion of the welded sheet comprising more than one material. In other embodiments, multiple sheets of at least two different materials can be layered, rolled and/or sealed together, for example, and the staple can be cut from a portion of the sheet comprising more than one material. In such embodiments, the COM of the staple can be offset from the center of geometry of the staple. For example, the COM of the staple can be laterally and/or longitudinally offset from the staple's center of geometry.

Figure 62:
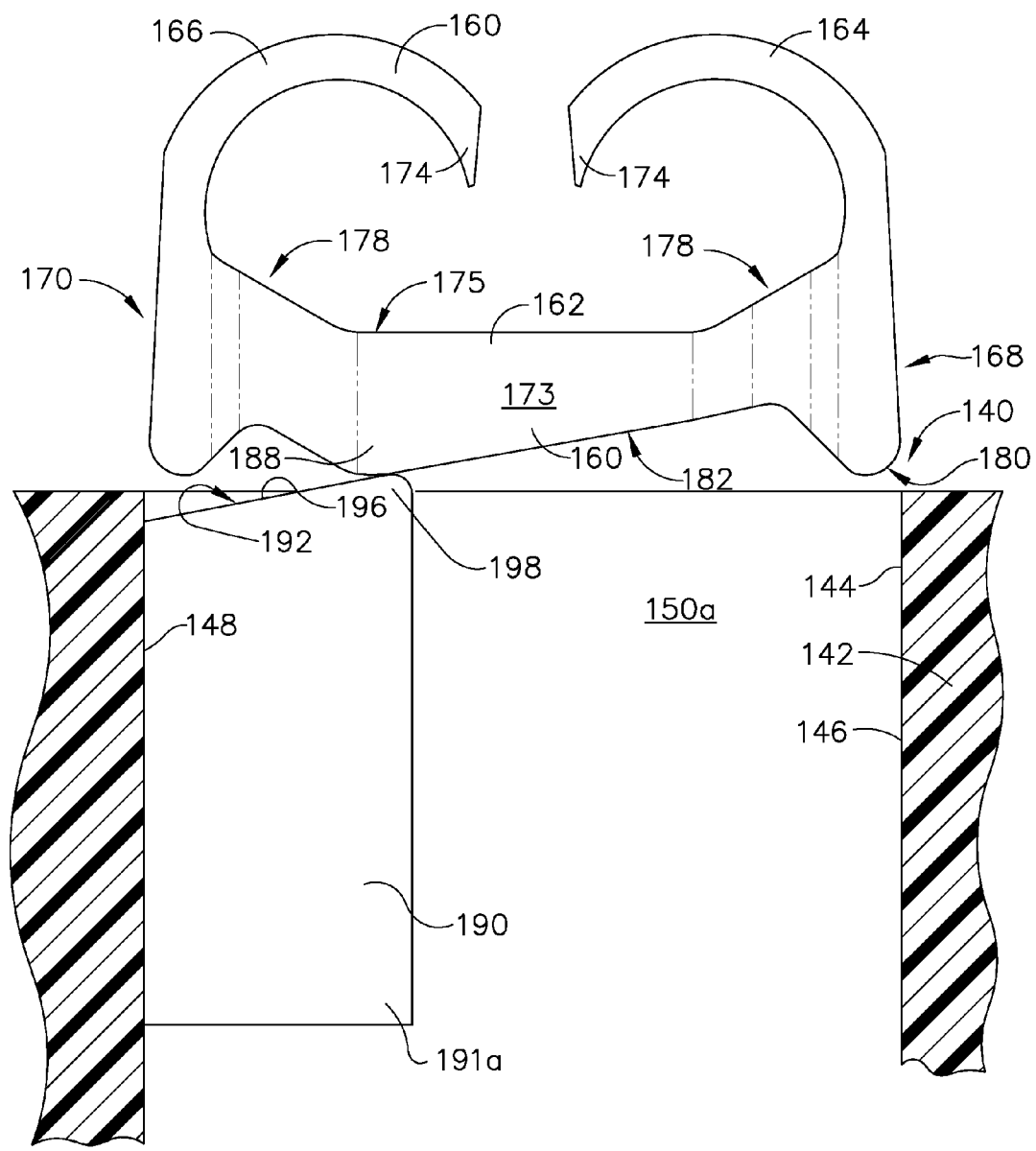
FIG. 62 is a partial, cross-sectional elevation view of the staple cartridge of FIG. 56, depicting the staple in an ejected position and in a deformed configuration, according to various embodiments of the present disclosure.
Figure 63:
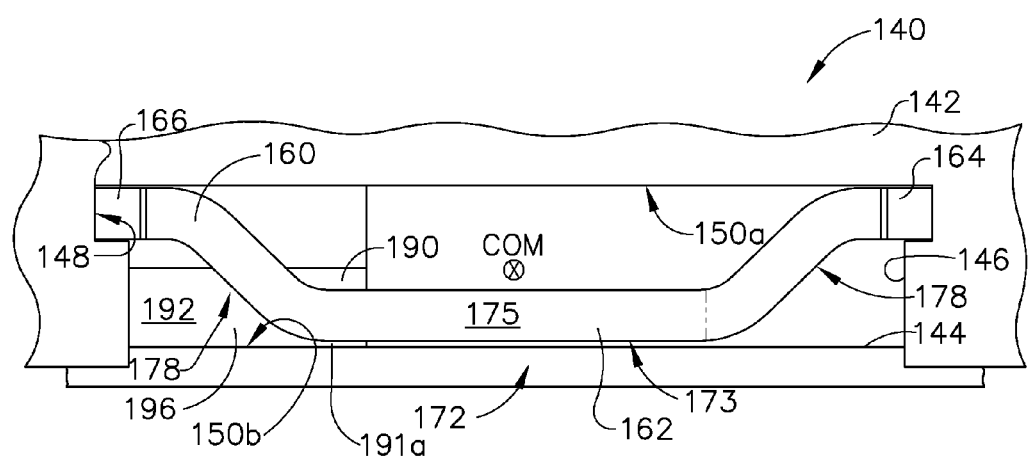
FIG. 63 is a partial plan view of the staple cartridge of FIG. 56, depicting the staple in the ejected position and in the deformed configuration depicted in FIG. 62.
Figure 64:
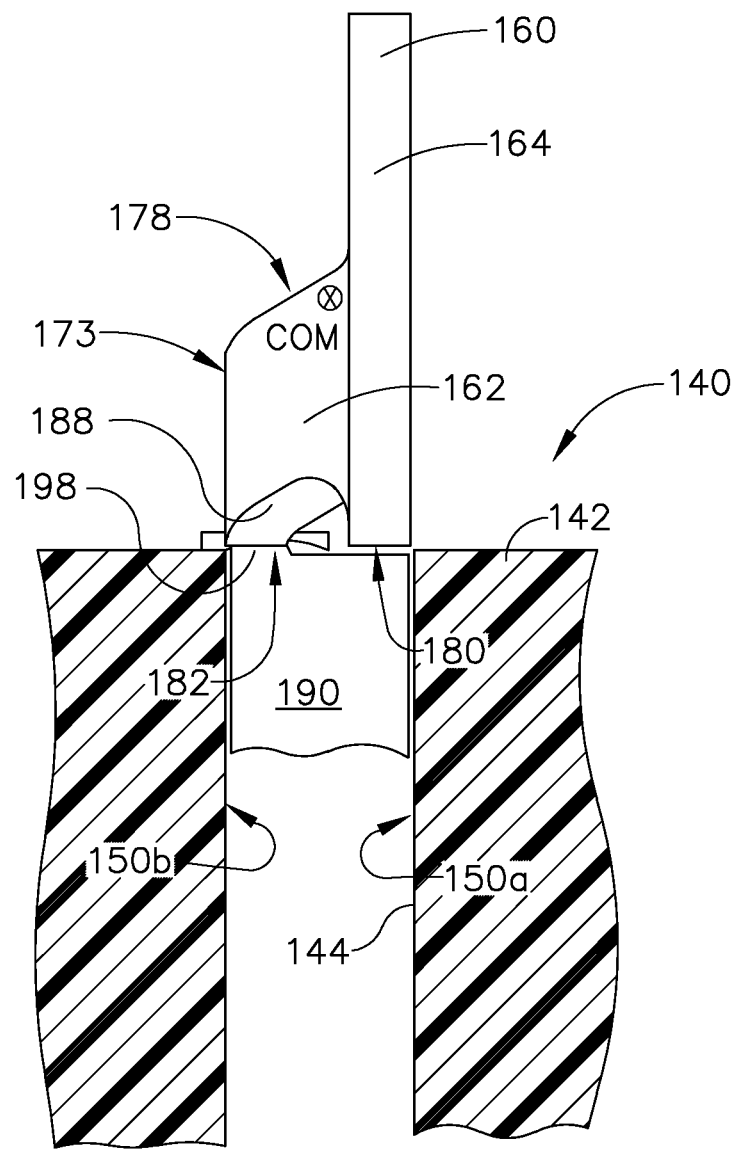
FIG. 64 is a partial, cross-sectional elevation view of the staple cartridge of FIG. 56, depicting the staple in the ejected position and the deformed configuration depicted in FIG. 62.

As depicted in FIGS. 58 and 61, the sled 190 can exert a vertical driving force $D_1$, $D_2$ on the staple 160 during deployment. The reader will appreciate that a driving force generated by the sled 190 can also comprise a horizontal component. In various embodiments, the proximal and/or distal ends 146, 148 of the staple cavity 144 can guide and support the staple legs 164, 166, as the staple 160 is lifted by the sled 190. In various embodiments, the proximal and/or distal ends 146, 148 of the staple cavity 144 can balance the torque generated by the horizontal component of the driving force. For example, as the sled 190 moves distally, the distal end 148 of the staple cavity 144 can resist rotation and/or torquing of the staple 160 during deployment. Referring now to FIGS. 62-64, the trailing surface 196 can continue to lift the staple 160 out of the staple cavity 144. For example, the sled overdrive 198 can contact the staple overdrive 188 to lift the base 162 of the staple 160 out of the cartridge body 140.

Figures 45, 46:
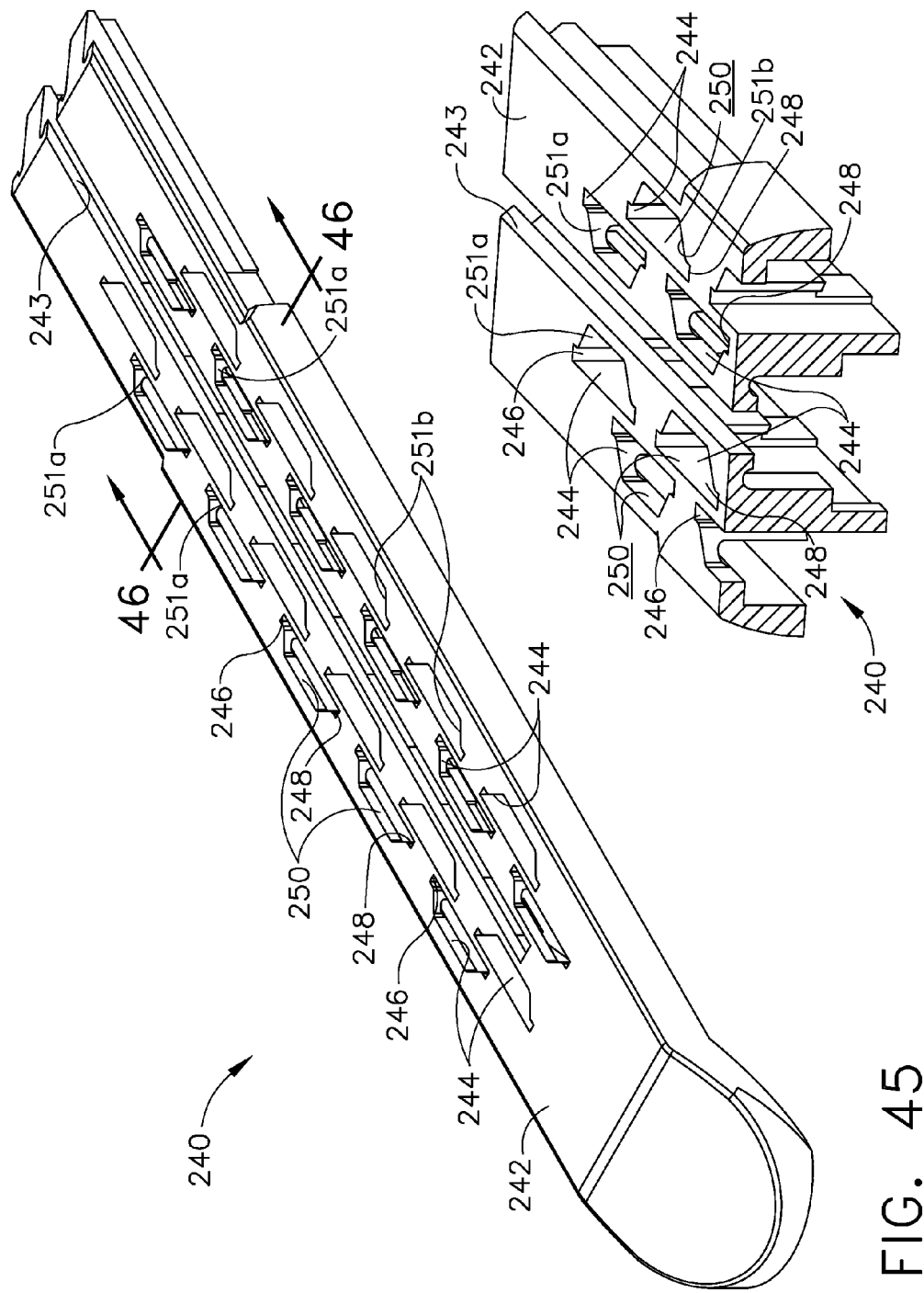
FIG. 45 is a perspective view of a staple cartridge according to various embodiments of the present disclosure.
FIG. 46 is a cross-sectional perspective view of the staple cartridge of FIG. 45 taken along the plane indicated in FIG. 45.
Figure 47:
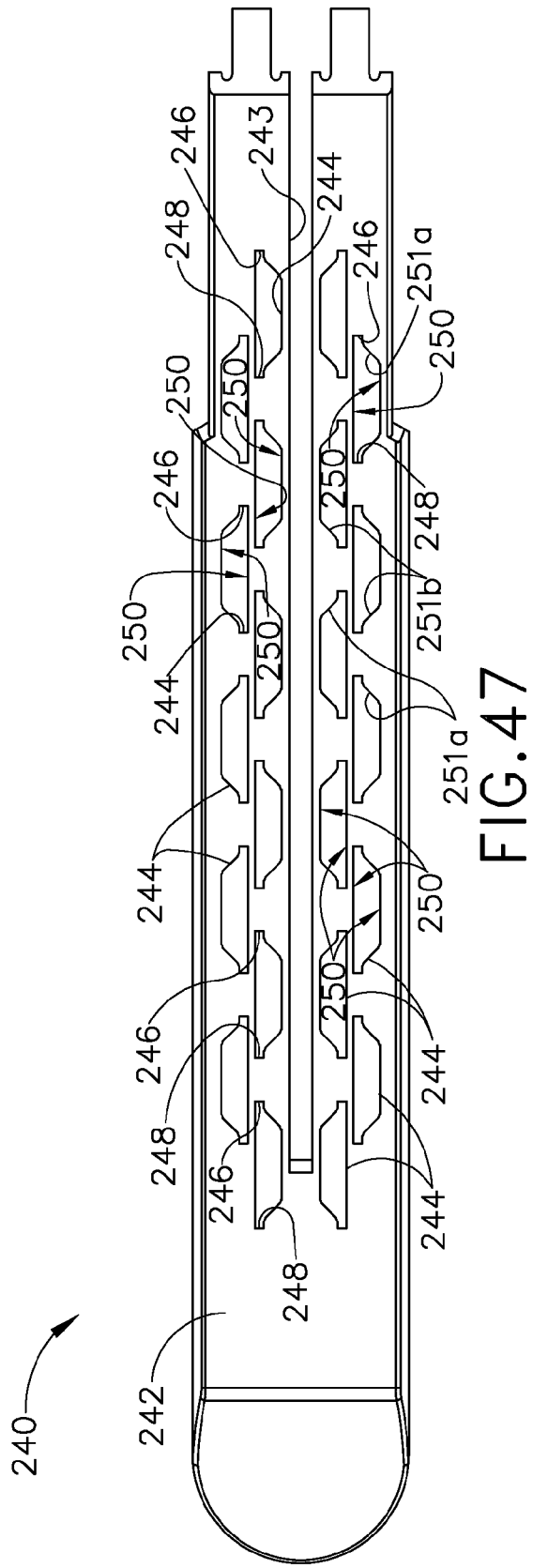
FIG. 47 is a plan view of the staple cartridge of FIG. 45.
Figure 53:
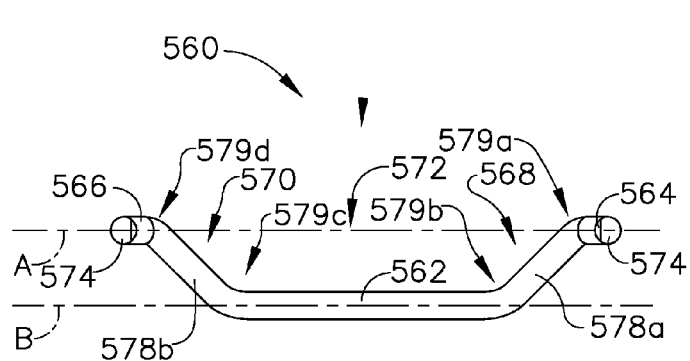
FIG. 53 is a plan view of the staple of FIG. 52.
Figure 52:
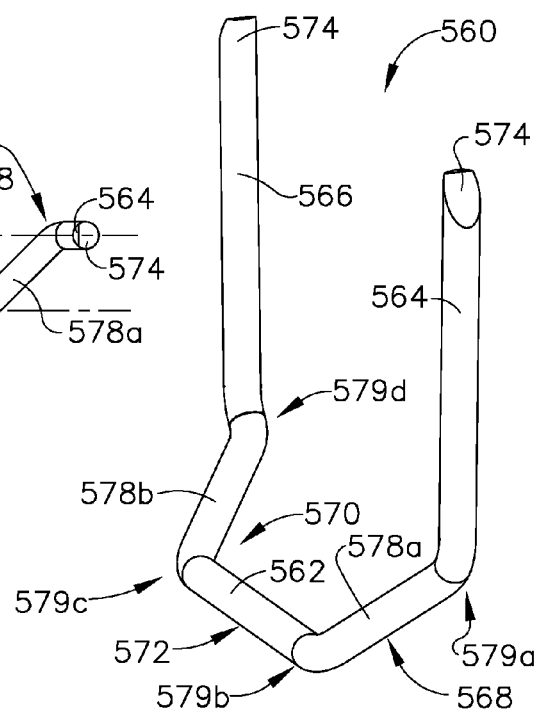
FIG. 52 is a perspective view of a staple according to various embodiments of the present disclosure.
Figure 54:
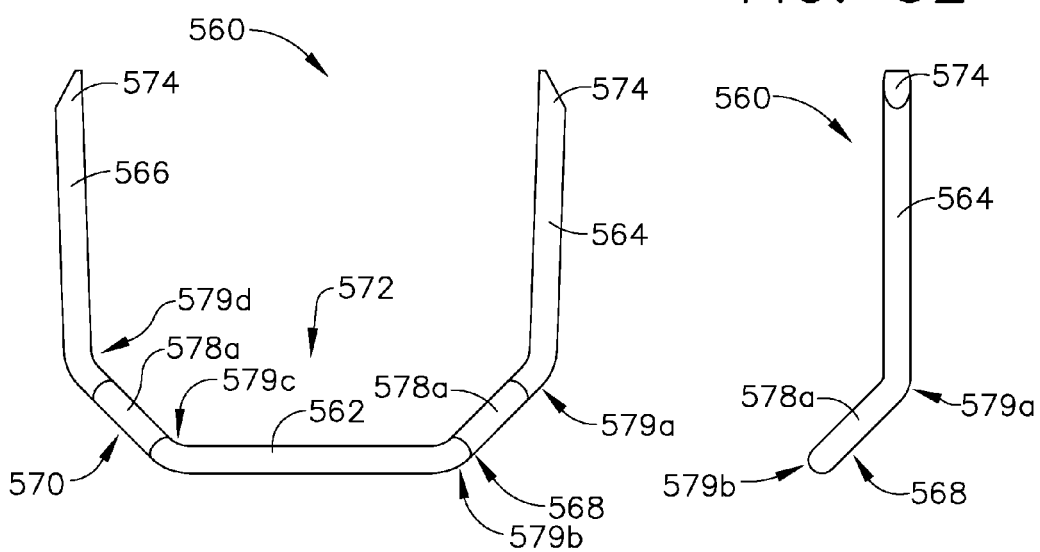
FIG. 54 is a front elevation view of the staple of FIG. 52.
Figure 55:
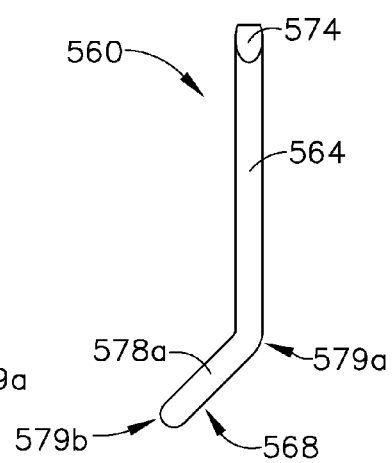
FIG. 55 is a side elevation view of the staple of FIG. 52.

Referring now to FIGS. 45-47, a staple cartridge, such as a staple cartridge 240, for example, can be loaded into the elongate channel 122 of the end effector 120 (FIG. 3). Staples, such as staples 160, for example, can be ejectably positioned in the staple cartridge 240. For example, sleds 190 (FIGS. 14-17) can translate through the staple cartridge 240 to eject the staples 160 therefrom. In various instances, the staple cartridge 240 can include a cartridge body 242 and cavities 244 defined in the cartridge body 242. Staples 160 can be removably positioned in the staple cavities 244, for example. For example, each staple cavity 244 can removably store a single staple 160. Moreover, each staple cavity 244 can have a proximal end 246 and a distal end 248, for example, and longitudinal sidewalls 250 can extend between the proximal end 246 and the distal end 248 of each staple cavity 244. Similar to the cavities 144 described herein, the proximal ends 246, distal ends 248, and/or longitudinal sidewalls 250 can guide and/or support the staples 160 during firing. For example, the longitudinal sidewalls 250 can counterbalance the torque exerted on the staple 160 by the translating sled 190. In various instances, the cavities 244 can also include diagonal guide surfaces 251 between the sidewalls 250. For example, a proximal diagonal guide surface 251a can extend between the proximal end 246 of the cavity 244 and a sidewall 250 of the cavity 244. Additionally or alternatively, a distal diagonal guide surface 251b can extend between the distal end 248 of the cavity 244 and a sidewall 250 of the cavity 244. The diagonal guide surfaces 251a, 251b can guide and/or support the contoured portions 178 (FIGS. 6-13) of the staple 160, for example, as the staple 160 is lifted within the staple cavity 244. For example, a portion of the contoured portion 178 can slide along and/or move against the diagonal guide surfaces 251a, 251b. In such an arrangement, the diagonal guide surfaces 251a, 251b can balance the torque exerted on the staple 160, for example.

Referring now to FIGS. 32A-32C, staples, such as the staples 160, for example, can be cut, formed and/or stamped from a sheet of material, such as a sheet of material 130, for example. The sheet of material 130 can be metallic, for example, and can comprise stainless steel and/or titanium, for example. In various instances, the sheet of material 130 can be substantially flat and/or smooth. Moreover, in certain instances, the sheet of material 130 can be bent, folded, contoured and/or crimped at various regions, such as a first region 134 and a second region 136, for example. The sheet of material 130 can be bent using a punch and/or stamp, for example. Flat or substantially flat portions 135a, 135b, and 135c of the sheet of material 130 can be positioned intermediate the regions 134, 136, for example. The first region 134 can be intermediate the flat portions 135a and 135b, for example, and the second region 136 can be intermediate the flat portions 135b and 135c, for example. In various instances, the flat portions 135a and 135c can be coplanar, for example, and/or the flat portion 135b can be parallel and/or substantially parallel to the flat portions 135a and/or 135c, for example. Referring primarily to FIG. 32A, multiple flat sheets 130a, 130b, 130c, 130d, 130e, 130f can be stacked, and then bent at the regions 134 and 136 simultaneously. In other embodiments, the sheets 130a, 130b, 130c, 130d, 130e, 130f can be individually bent, for example, and then stacked.

In various instances, the staples 160 can be cut, formed and/or stamped from the bent sheets 130. For example, referring primarily to FIG. 32B, a staple outline 132 can be traced, etched, and/or cut into the bent sheets 130. The staple outline 132 can be machined and/or laser cut into the bent sheets 130, for example. In various instances, an electron discharge machining (EDM) wire 138 can be used to cut the staple outline 132. Furthermore, in certain instances, multiple stacked sheets 130 can be cut simultaneously. In certain embodiments, referring primarily to FIG. 32C, the staple outline 132 can form the boundary or perimeter of the staple 160. For example, the staple outline 132 can form the staple 160 (FIGS. 6-13 and 33-36), and/or can form a staple having various similar features to the staple 160, for example. In various instances, multiple staple outlines 132 can be cut into the sheet of material 130, and multiple staples 160 can be formed from a single sheet of material 130. As illustrated in FIGS. 32B and 32C, the EDM wire 138 can pass through more than one sheet of material 130 at a time to cut more than one staple 160 at a time. While six sheets 130 are being simultaneously cut by the EDM wire 138, any suitable number of sheets 130 can be cut at the same time. For instance, a wire 138 can cut less than six sheets 130 at the same time or more than six sheets 130 at the same time.

For example, referring to FIGS. 32C and 33-36, the staple outline 132 can form the base 162 and/or the staple legs 164, 166, for example. Furthermore, the staple outline 132 can include at least one integrally-formed staple drive surface. For example, the staple outline 132 can include the initial drive surface 180 and/or the secondary drive surface 182. In other words, the initial drive surface 180 and/or the secondary drive surface 182 can be machined and/or formed at the time the staple 160 is cut from the sheet of material 130. In certain instances, the bent or contoured regions 134, 136 of the sheet 130 (FIGS. 32A and 32B) can form the contoured portions 178 of the staple 160. Moreover, the lateral flat portions 135a and 135c of the sheet 130 (FIGS. 32A and 32B) can correspond to the staple legs 164 and 166, and the intermediate flat portion 135b of the sheet 130 (FIGS. 32A and 32B) can correspond to the intermediate portion 172 of the base 162, for example.

In various instances, the depth $D_1$ (FIGS. 34 and 36) of the staple 160 can determined by the depth of the sheet of material 130. For example, the sheet of material 130 can be selected based on the depth thereof, and the staple 160 formed from that sheet of material 130 can have the same depth as the sheet of material 130. Furthermore, the height $H_1$ (FIG. 35), and width $W_1$ (FIG. 35) of the base 162 and the staple legs 164, 166 can be determined by the staple outline 132. In various instances, the staple outline 132 can provide variations in the height and/or width of the staple components along the length of each component. For example, the height $H_1$ of the base 162 and/or the width $W_1$ of the staple legs 164, 166 can vary along the length thereof. Furthermore, tapers, steps, and/or other variations can be defined by the staple outline 132, and thus, the geometry of the staple 160 can be selected and/or manipulated based on the purpose, application, and/or design of the staple 160 and/or the end effector 120 with which the staple 160 may be used.

Referring primarily to FIGS. 33-36, in various instances, the staple 160 can be cut such that the height $H_1$ of the base 162 is independent of and/or different than the depth $D_1$ of the staple legs 164, 166. For example, the depth $D_1$ of the staple legs 164, 166 can correspond to the depth of the sheet of material 130, and the base 162 can be cut to an appropriate height $H_1$, which can be independent of the depth of the sheet of material 130 and/or the corresponding leg depth $D_1$, for example. The appropriate height $H_1$ can be based on the purpose, application, and/or design of the staples 160 and/or the end effector 120 (FIG. 3) with which the staple 160 may be used, for example. Furthermore, the height $H_1$ of the base 162 can also vary along the length thereof. For example, the height $H_1$ can vary at and/or near a drive surface of the staple 160, and/or at a gusset between one of the staple legs 164, 166 and the base 162, for example. The staple outline 132 can provide at least one taper and/or step along the length of the base 162, for example. The staple outline 132 can comprise a taper or ramp, for example, which can form the secondary drive surface 182 of the base 162. The degree of incline of the secondary drive surface 182 can be selected, designed and implemented via the staple outline 132. In certain embodiments, the height $H_1$ of the base 162 can be greater than the depth $D_1$ of the staple legs 164, 166. In other embodiments, the height $H_1$ of the base 162 can be equal to or less than the depth $D_1$ of the staple legs 164, 166. Comparatively, the geometry of a staple that is formed from a bent wire may be constrained and/or limited based on the dimensions of the initial wire. For example, in a wire-formed staple, the height of the staple base typically corresponds to the width of the staple legs, which typically corresponds to the diameter of the wire. Though drawing and/or rolling, for example, can modify the diameter of the wire, the volume of material limits and/or restrains the permissible modifications.

In various instances, the width $W_1$ of the staple legs 164, 166 can also be independent of the depth $D_1$ of the staple legs 164, 166 and the height $H_1$ of the base 162, for example. The staple legs 164, 166 can be cut to an appropriate width $W_1$ based on the application, purpose and/or design of the staple 160 and/or the end effector 120 (FIG. 3) with which the staple 160 may be used, for example. In certain embodiments, the staple legs 164, 166 can comprise different widths, for example, and/or the width of the staple legs 164, 166 can taper, step, or otherwise vary along the length thereof. For example, the staple legs 164, 166 can taper at the tips 174 to form a piercing edge or point.

Referring now to FIGS. 37-40, a staple outline 232 can be traced, cut, etched, and/or machined into the sheet of material 130 (FIGS. 32A and 32B), and a staple 260, similar to the staple 160 (FIGS. 33-36), for example, can be formed from the sheet of material 130. For example, the staple 260 can include a base 262 and staple legs 264, 266 extending from the base 262. In various embodiments, the staple 260 can include contoured portions 278, which can correspond to the bent and/or contoured regions 134, 136 of the sheet of material 130 (FIGS. 32A and 32B) from which the staple 260 was formed. In certain embodiments, the staple 260 can include an intermediate portion 272 between the contoured portions 278, for example. Moreover, at least one drive surface 280, 282 can be formed along the perimeter of the staple 260 via the staple outline 232.

Similar to the staple 160, the depth $D_1$ of the staples legs 264, 266 can correspond to the depth of the sheet of material 130. Furthermore, in various instances, the height $H_2$ of the staple base 262 can be independent of the depth $D_1$ of the staple legs 264, 266 and/or independent of the depth of the sheet of material 130. For example, as depicted in FIGS. 37-40, the height $H_2$ of the staple base 262 is less than the height $H_1$ of the staple base 162 (FIGS. 33-36), and the depth $D_2$ of the staples legs 264, 266 is equal to the depth $D_1$ of the staple legs 164, 166, for example. In various embodiments, the width $W_2$ of the staple legs 264, 266 can also be independent of the depth $D_2$ of the staple legs 264, 266. The height $H_1$ of the staple base 262 and the width $W_2$ of the staple legs 264, 266 can be selected based on the purpose, application, and/or design of the staple 260 and/or the end effector 120 (FIG. 3), for example.

Referring now to FIGS. 41-44, a staple outline 332 can be traced, cut, etched, and/or machined into the sheet of material 130 (FIGS. 32A and 32B), and a staple 360, similar to the staples 160 and 260 (FIGS. 33-40), for example, can be formed from the sheet of material 130. For example, the staple 360 can include a base 362 and staple legs 364, 366 extending from the base 362. In various embodiments, the staple 360 can include contoured portions 378, which can correspond to the bent and/or contoured regions 134, 136 of the sheet of material 130 (FIGS. 32A and 32B) from which the staple 360 was formed. In certain embodiments, the staple 360 can include an intermediate portion 372 between the contoured portions 378, for example. Moreover, at least one drive surface 380 and 382 can be formed along the perimeter of the staple 360 via the staple outline 332.

Similar to the staples 160 and 260, the depth $D_3$ of the staples legs 364, 366 can correspond to the depth of the sheet of material 130. Furthermore, in various instances, the height $H_3$ of the staple base 362 can be independent of the depth $D_3$ of the staple legs 364, 366 and/or independent of the depth of the sheet of material 130. For example, as depicted in FIGS. 41-44, the height $H_3$ of the staple base 362 is greater than the height $H_1$ of the staple base 162 (FIGS. 33-36) and greater than the height $H_2$ of the staple base 262 (FIGS. 37-40), and the depth $D_3$ of the staples legs 364, 366 is equal to the depth $D_1$ of the staple legs 164, 166 and equal to the depth $D_2$ of the staple legs 264, 266, for example. In various embodiments, the width $W_3$ of the staple legs 364, 366 can also be independent of the depth $D_3$ of the staple legs 364, 366. The height $H_3$ of the staple base 362 and the width $W_3$ of the staple legs 364, 366 can be selected based on the purpose, application, and/or design of the staple 360 and/or the end effector 120 (FIG. 3), for example.

Referring now to FIGS. 48-51, a staple, such as a staple 460, for example, can be used in a staple cartridge, such as the staple cartridge 140 (FIGS. 3-5) and/or the staple cartridge 240 (FIGS. 45-47), for example. The staple 460 can include a base 462 having a proximal portion 468 and a distal portion 470. An intermediate base portion 472 can be positioned between the proximal portion 468 and the distal portion 470, for example. As depicted in FIGS. 48-51, a first staple leg 464 can extend from the proximal portion 468 of the base 462, and a second staple leg 466 can extend from the distal portion 470 of the base. In various instances, the staple legs 464, 466 can be cylindrical or substantially cylindrical, for example, and can include a staple tip 474, which can be tapered and/or include a sharp edge or point for piercing tissue, for example. In other embodiments, the staple legs 464, 466 can include a rounded and/or polygonal perimeter, for example. The intermediate portion 472 of the staple base 462 can include a tissue-contacting surface 473, which can be flat or substantially flat, for example. In various instances, the staple 460 can be formed from a wire, for example, which can be bent, twisted, and/or otherwise manipulated to form the staple legs 464, 466 and/or the staple base 462, for example. In various embodiments, the diameter of the wire can define the width and depth of the staple legs 464, 466, for example. In some embodiments, the wire can be drawn and/or rolled to modify the dimensions of the staple 460. In certain instances, the intermediate portion 462 of the wire base 462 can be formed and/or flattened to form the tissue-contacting surface 473. In various instances, the base 462 can be flattened between two parallel or substantially parallel plates, for example, such that the tissue-contacting surface 473 and a bottom surface 475 of the base 462 are flat or substantially flat and/or parallel or substantially parallel. Modifications to the base 162 may be limited and/or constrained by the volume of material of the wire, for example.

Referring still to FIGS. 48-51, the staple 460 can include chamfers and/or gussets. For example, a chamfer 484 can extend between the first staple leg 464 and the base 462, and/or a chamfer 484 can extend between the second staple leg 466 and the base 462. In certain embodiments, the chamfers 484 can be asymmetrical relative to a longitudinal axis G (FIG. 49) extending between the first staple leg 464 and the second staple leg 466, and/or relative to a vertical axis H (FIG. 51) extending along the length of the staple legs 464, 466, for example. The chamfers 484 can extend away from the axis G and/or the axis H, for example, and thus, in certain embodiments, the intermediate portion 472 of the base 462 can be offset from the axis G and/or the axis H. For example, the center of mass of the base 462 can be offset from the plane defined by the axis G and the axis H. In various instances, the offset intermediate portion 472 of the base 462 can form a wide and/or flat surface for contacting captured tissue, which can provide a broad and/or smooth surface for applying and/or distributing pressure on the captured tissue. In such embodiments, tissue tearing and/or trauma within the staple 460 may be reduced and/or minimized. Moreover, similar to the staples 160, 260, and/or 360 described herein, the staple 460 can include a leg formation plane, e.g., the plane defined by the axis G and the axis H, which can be offset from the center of mass of the base 462 of the staple 460, for example.

Referring now to FIGS. 52-55, a staple, such as a staple 560, for example, can be used in a staple cartridge, such as the staple cartridge 140 (FIGS. 3-5) and/or the staple cartridge 240 (FIGS. 45-47), for example. The staple 560 can include a base 562 having a proximal portion 568 and a distal portion 570. An intermediate base portion 572 can be positioned between the proximal portion 568 and the distal portion 570, for example. As depicted in FIGS. 52-55, a first staple leg 564 can extend from the proximal portion 568 of the base 562, and a second staple leg 566 can extend from the distal portion 570 of the base 562. In certain embodiments, the intermediate portion 572 of the base 560 can extend along an axis D (FIG. 53), which can be parallel and/or substantially parallel to an axis C (FIG. 53) defined between the first staple leg 564 and the second staple leg 566, for example.

In various instances, the staple legs 564, 566 can be cylindrical or substantially cylindrical, for example, and can include a staple tip 574, which can be tapered and/or include a sharp edge or point for piercing tissue, for example. In various instances, the staple 560 can be formed from a wire. For example, a wire can be bent, twisted and/or otherwise manipulated to form the staple 560. Referring still to FIGS. 52-55, the wire can be manipulated at curves 579a, 579b, 579c, and/or 579d. For example, the staple base 562 can include angled portions 578, which can be angularly oriented relative to the intermediate portion 572 of the staple base 562 and/or relative to the axis C defined between the first and second staple legs 564, 566, for example. In various embodiments, the wire forming the staple 560 can curve at 579a between the first staple leg 564 and the angled portion 578a, curve at 579b between the angled portion 578a and the intermediate portion 572, curve at 579c between the intermediate portion 572 and the angled portion 578b, and/or curve at 579d between the angled portion 578b and second staple leg 566, for example. For example, the intermediate portion 572 of the base 562 can be laterally offset from the axis C (FIG. 53) extending between the first staple leg 564 and the second staple leg 566.

In various embodiments, the diameter of the wire can define the width and depth of the staple legs 564, 566 and/or the staple base 562, for example. In some embodiments, the wire and/or portions thereof can be drawn and/or rolled to modify the dimensions of the staple 560 and/or elements of the staple 560. Furthermore, the wire can have a rounded and/or polygonal perimeter. In certain embodiments, the wire can be cut at an angle to form the staple tips 574, for example. Similar to the staples 160, 260, 360 and/or 460 described herein, the staple 560 can include a leg formation plane, e.g., the plane defined by the axis C, which can be offset from the center of mass of the base 562 of the staple 560, for example.

Figure 65:
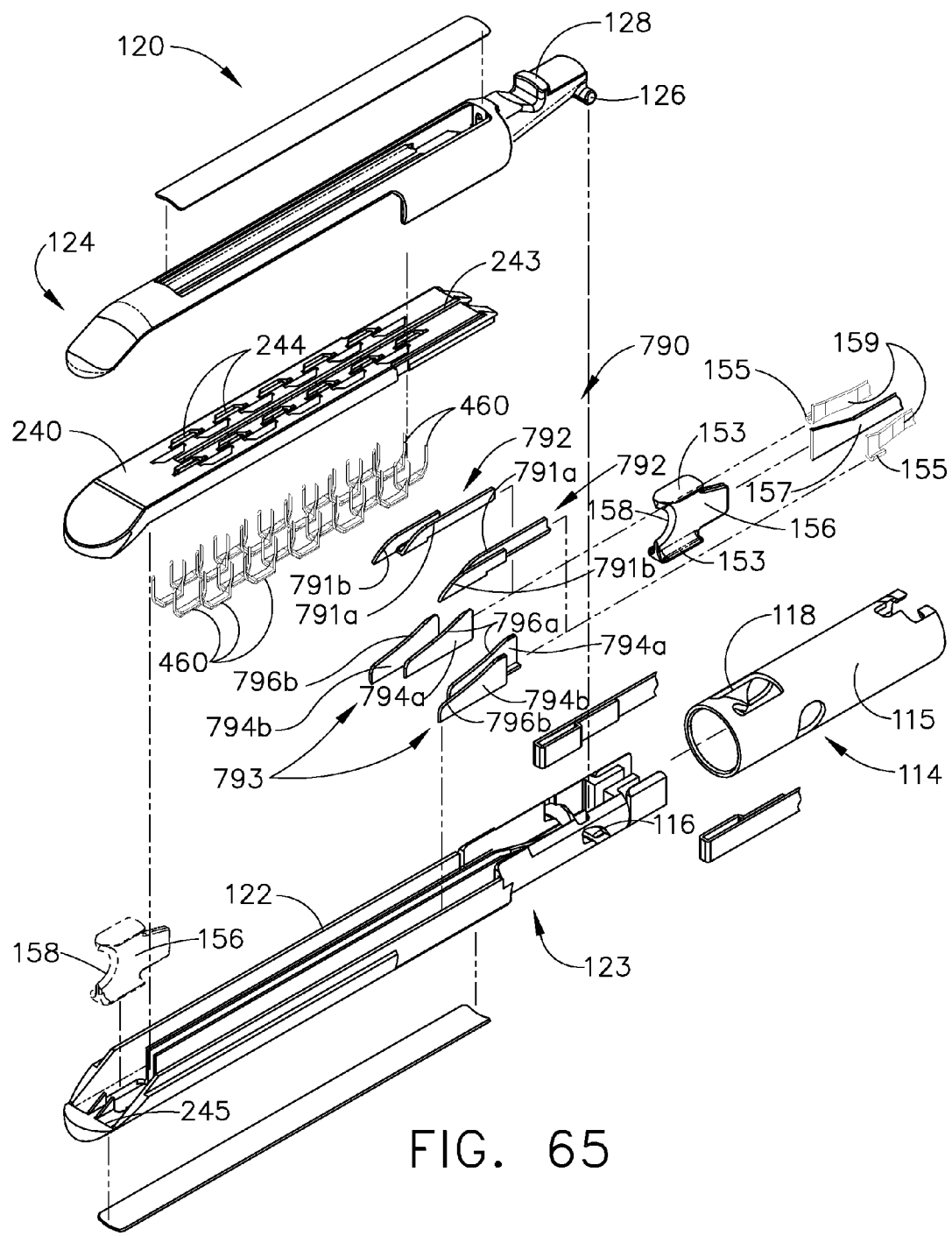
FIG. 65 is an exploded perspective view of an end effector comprising a plurality of fasteners and a firing actuator configured to eject the fasteners from the end effector according to various embodiments of the present disclosure.

Further to the above, turning now to FIG. 65, an end effector, such as end effector 120, for example, can include a staple cartridge 240 positioned within an elongate channel 122 and, in addition, an anvil 124 positionable opposite the staple cartridge 240. In various instances, the cartridge 240 can include a plurality of staple cavities 244, a fastener, such as staple 460, for example, positioned in each of the staple cavities 244, and a longitudinal slot 243 configured to slidably receive a knife 158 therein. While staples 460 are depicted in connection with the embodiment depicted in FIG. 65, any suitable staple or fastener could be used with this embodiment, such as staples 160, for example. Referring generally to FIGS. 73 and 74, the end effector 120 can extend from a shaft 114 which can include a closure tube 115. When the closure tube 115 is advanced distally, the closure tube 115 can contact the anvil 124 and rotate the anvil 124 between an open position (FIG. 73) and a closed position (FIG. 74). Once the anvil 124 has been closed, the knife 158 can be advanced distally to transect tissue captured between the anvil 124 and the cartridge 240. In certain end effectors disclosed herein, the cartridge positioned within the end effector 120 can further include a fastener firing actuator, such as sled 190, for example, which is pushed distally by the knife 158 to deploy staples from the cartridge at the same time that the knife 158 transects the tissue. With regard to the embodiment depicted in FIG. 65, a staple cartridge can include a fastener firing actuator, such as sled assembly 790, for example, which can be advanced distally with, or alongside, the knife 158 to eject the staples 460 from the cartridge 240. For instance, the shaft 114 of the stapler can include a firing bar 157 configured to advance the knife 158 and, in addition, pusher bars 159 configured to advance the sled assembly 790. While the firing bar 157 and the pusher bars 159 may be advanced concurrently, in various circumstances, their operation can be timed in such a way that their initial distal movement can be staggered relative to one another, as described in greater detail further below. In addition to the initial relative movement between the firing bar 157 and the pusher bars 159, the sled assembly 790 can include two or more portions which can move relative to one another, as will also be described in greater detail further below.

Figure 66:
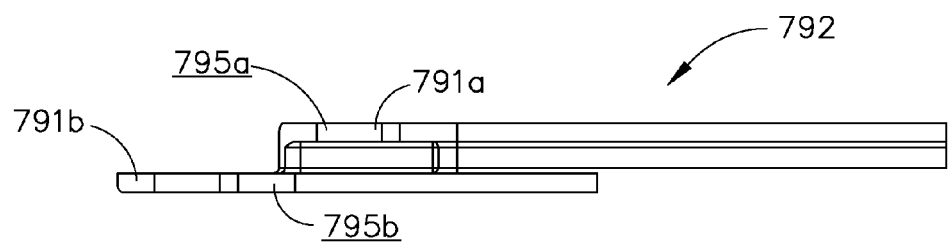
FIG. 66 is a plan view of a first portion of the fastener firing actuator of FIG. 65.
Figure 67:
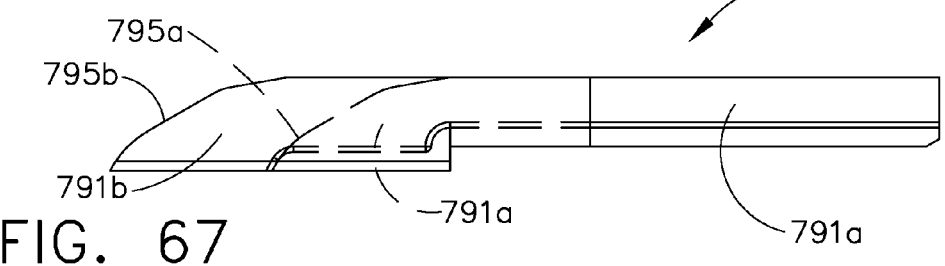
FIG. 67 is an elevational view of the first portion of FIG. 66.
Figure 68:
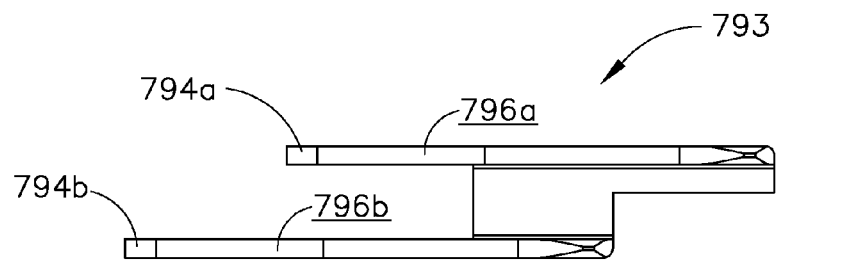
FIG. 68 is a plan view of a second portion of the fastener firing actuator of FIG. 65.
Figure 69:
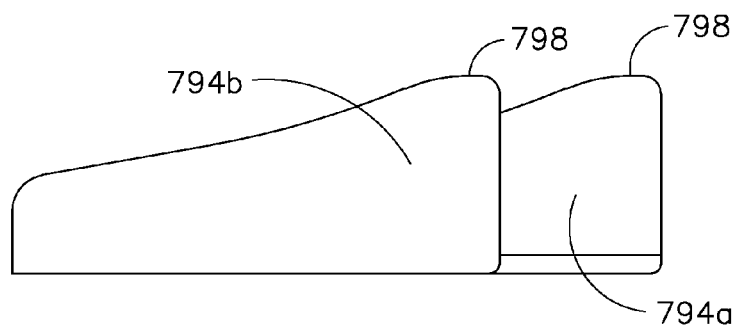
FIG. 69 is an elevational view of the second portion of FIG. 68.
Figure 75:
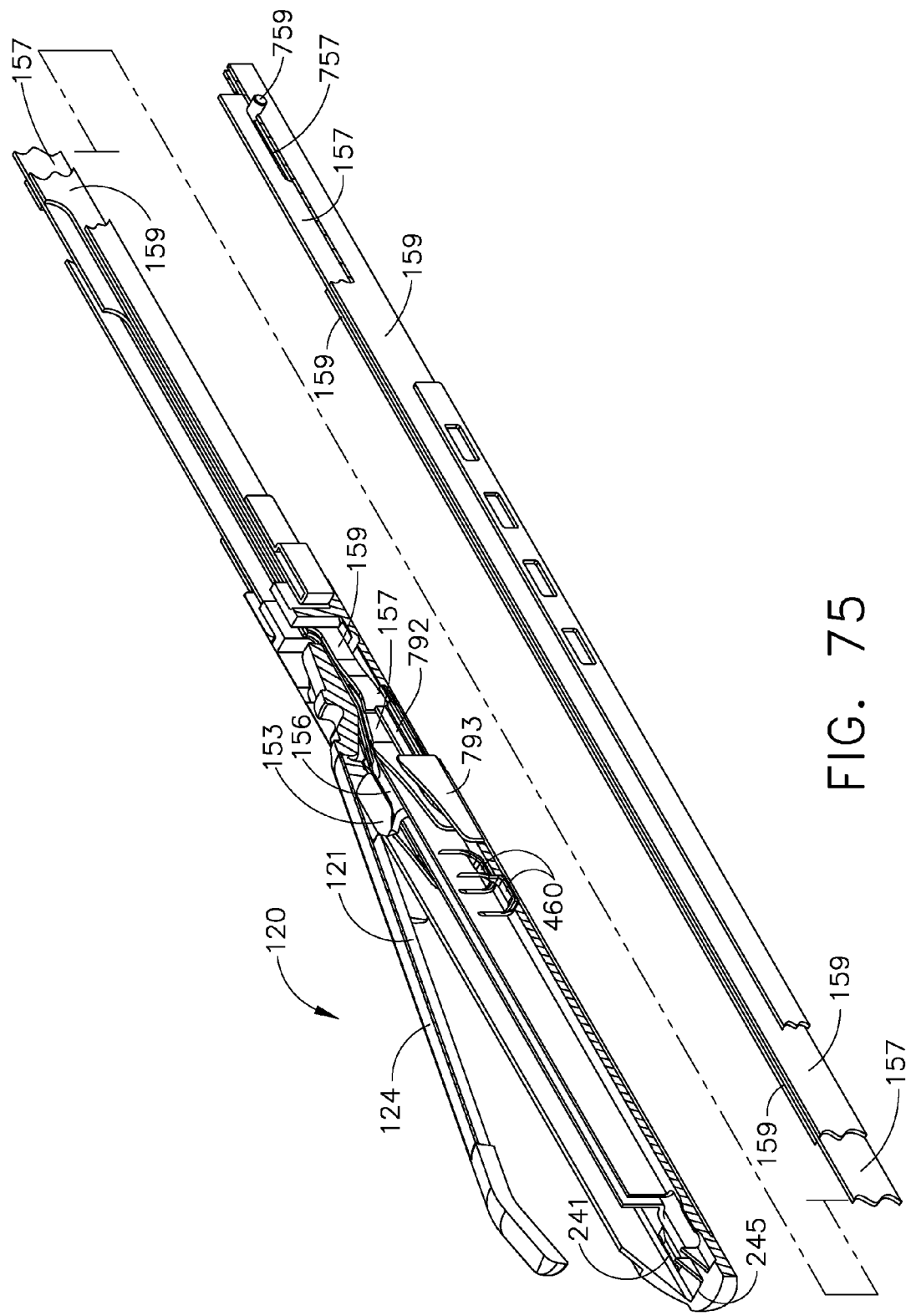
FIG. 75 is a cross-sectional perspective view of the end effector of FIG. 65 illustrated in the configuration depicted in FIG. 73.
Figure 76:
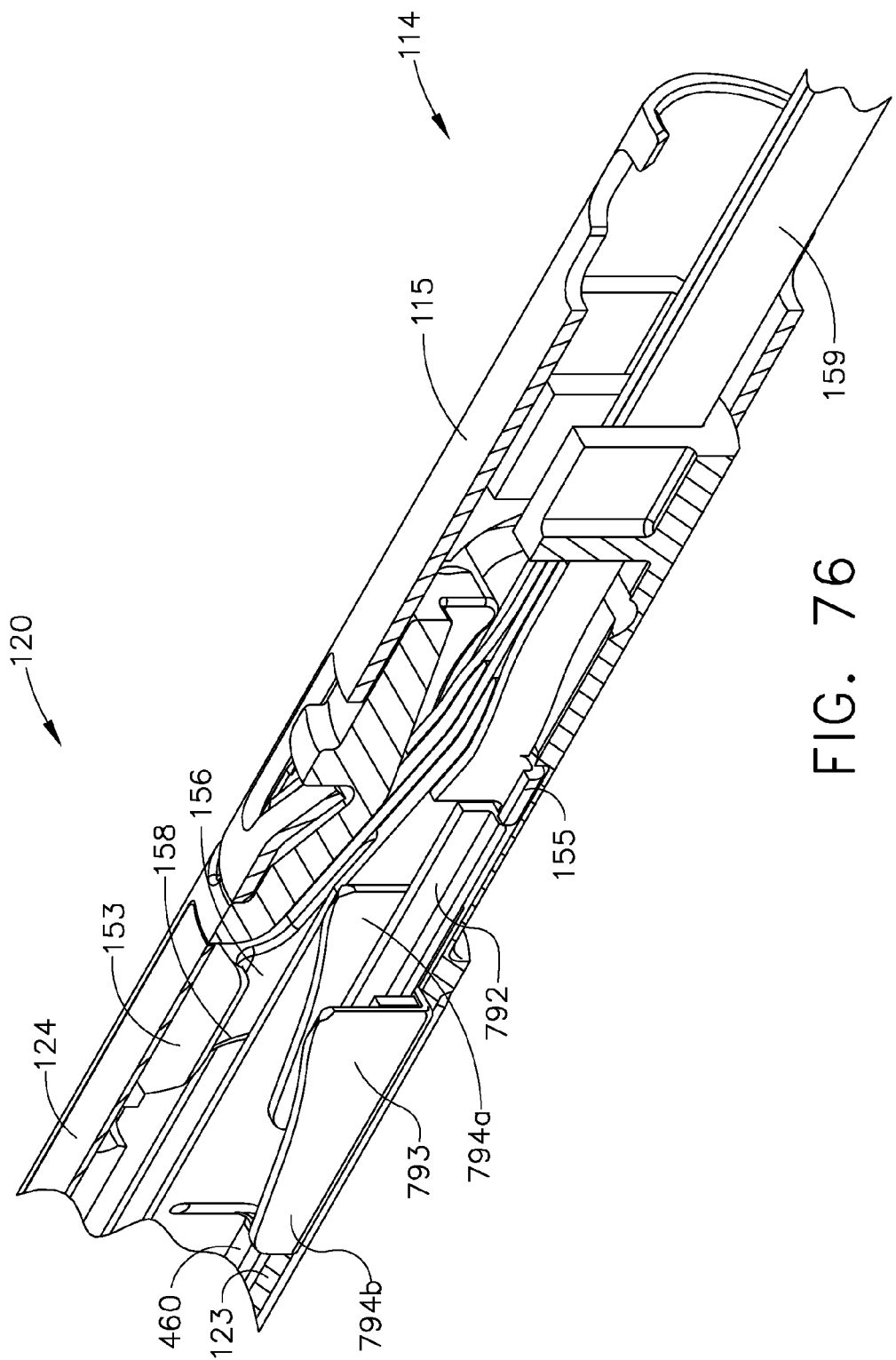
FIG. 76 is a cross-sectional view of the end effector of FIG. 65 illustrated in the configuration depicted in FIG. 74.

Referring primarily to FIGS. 66-69, the sled assembly 790 can include a first sled portion 792 and a second sled portion 793. The first sled portion 792 can include an inner ramp portion 791a and an outer ramp portion 791b. As illustrated in FIGS. 66 and 67, the outer ramp portion 791b is positioned laterally with respect to the inner ramp portion 791a. The outer ramp portion 791b also extends distally with respect to the inner ramp portion 791a. Similarly, the second sled portion 793 can include an inner ramp portion 794a and an outer ramp portion 794b. As illustrated in FIGS. 68 and 69, the outer ramp portion 794b is positioned laterally with respect to the inner ramp portion 794a. The outer ramp portion 794b also extends distally with respect to the inner ramp portion 794a. In various instances, the inner ramp portion 791a can be configured to lift, or at least partially lift, an inner row of staples while the outer ramp portion 791b can be configured to lift, or at least partially lift, an outer row of staples. As primarily depicted in FIG. 67, the inner ramp portion 791a and the outer ramp portion 791b can each include a ramp surface, such as ramp surfaces 795a and 795b, respectively, which can slide underneath the staples in the inner row of staples and the outer row of staples, respectively. The ramp surfaces 795a and 795b of the inner ramp portion 791a and the outer ramp portion 791b can be configured to lift staples from an unfired position to an at least partially-fired position. In various instances, the ramp surfaces 795a and 795b of the inner ramp portion 791a and the outer ramp portion 791b can each comprise at least one inclined surface, curved surface, actuate surface, and/or convex surface, for example.

Further to the above, the inner ramp portion 794a of the second sled portion 793 can include an inner ramp surface 796a and, similarly, the outer ramp portion 794b of the second sled portion 793 can include an outer ramp surface 796b. In various instances, the inner ramp surface 795a of the first sled portion 792 can be configured to co-operate with the inner ramp surface 796a of the second sled portion 793 to lift the staples in the inner row of staples from their unfired positions and their fully-fired positions. More particularly, the inner ramp portion 791a can lift the staples in the inner row of staples from an unfired position to a partially-fired position wherein the inner ramp portion 794a can then lift the staples from their partially-fired positions to a fully-fired position, for instance. In such circumstances, the lifting motion of the staples in the inner row of staples can be initiated by the inner ramp portion 791a of the first sled portion 792, transferred to the inner ramp surface 796a of the second ramp portion 793, and then completed by the second ramp portion 793. Similarly, the outer ramp surface 795b of the first sled portion 792 can be configured to co-operate with the outer ramp surface 796b of the second sled portion 793 to lift the staples in the outer row of staples from their unfired positions and their fully-fired positions. More particularly, the outer ramp portion 791b can lift the staples in the outer row of staples from an unfired position to a partially-fired position wherein the outer ramp portion 794b can then lift the staples from their partially-fired positions to a fully-fired position, for instance. In such circumstances, the lifting motion of the staples in the outer row of staples can be initiated by the outer ramp portion 791b of the first sled portion 792, transferred to the outer ramp surface 796b of the second ramp portion 793, and then completed by the second ramp portion 793. The firing, or lifting, motion of the staples in the inner row of staples can be completed once the apex 798 of the inner ramp portion 794a has passed underneath the staples. Similarly, the firing, or lifting, motion of the staples in the outer row of staples can be completed once the apex 798 of the outer ramp portion 794b has passed underneath the staples.

Referring again to FIG. 65, the sled assembly 790 can include more than one first sled portion 792 and/or more than one second sled portion 793. In various instances, the sled assembly 790 can comprise a first set of sled portions comprising a first sled portion 792 and a second sled portion 793 and a second set of sled portions comprising a first sled portion 792 and a second sled portion 793. In certain instances, the second set of sled portions can constitute a mirror image of the first set. For the purposes of simplifying the description of the sled assembly 790 herein, reference may be made to only one set of sled portions; however, the reader should appreciate that the description regarding the operation of one set of sled portions could also apply to the concurrent operation of any suitable number sets of sled portions.

Further to the above, the outer staple rows of the cartridge 240, i.e., the rows furthest away from the channel 243, can lead the inner staple rows, i.e., the rows closest to the channel 243. Stated another way, the deformation of the staples in the outer row can begin before, or at least slightly before, the deformation of the laterally adjacent staples in the inner row. In other instances, the outer staple rows of the cartridge 240, i.e., the rows furthest away from the channel 243, can lag the inner staple rows, i.e., the rows closest to the channel 243. Stated another way, the deformation of the staples in the inner row can begin before, or at least slightly before, the deformation of the laterally adjacent staples in the outer row. Moreover, while two staples rows are disclosed on each side of the channel 243 defined in the cartridge 240, other embodiments are envisioned in which more than two staple rows, such as three staple rows, for example, are present on each side of the channel 243. In such embodiments, the sled assemblies can be configured to deploy an additional row of staples at the same time as the inner row of staples, at the same time as the outer row of staples, and/or at a time which is staged sequentially with respect to the inner row of staples and the outer row of staples.

As mentioned above, the first sled portion 792 is movable relative to the second sled portion 793 of the sled assembly 790. Turning now to FIGS. 70-72, the sled assembly 790 is movable between an initial, unfired configuration (FIG. 70) and a second, extended configuration (FIGS. 71 and 72). In the initial, unfired configuration of sled assembly 790, referring primarily to FIG. 70, the first sled portion 792 is collapsed within, or retracted relative to, the second portion 793. In at least one such instance, the distal end of the first sled portion 792 may not extend beyond the distal end of the second sled portion 793. In other instances, although not illustrated, the distal end of the first sled portion 792 may extend beyond the distal end of the second sled portion 793 when the first sled portion 792 is collapsed within the second portion 793. With further reference to FIG. 70, the reader will further appreciate that the staples 460 are in an unfired position as they have not yet been lifted toward the anvil 124. Upon comparing FIGS. 70 and 71, the reader will notice that the first sled portion 792 has been extended relative to the second sled portion 793. In such circumstances, the distal end of the first sled portion 792 is positioned distally with respect to the distal end of the second sled portion 793. The movement of the first sled portion 792 from its initial, unfired position to its extended position can position the inner ramp portion 791a and/or the outer ramp portion 791b of the first sled portion 792 underneath one or more staples 460. In other configurations, the movement of the first sled portion 792 from its initial, unfired position to its extended position may not position the inner ramp portion 791a and/or the outer ramp portion 791b underneath one or more staples 460. In any event, as illustrated in FIG. 71, the extension of the first sled portion 792 can at least partially lift at least one staple 460 toward the anvil 124 and/or at least partially deform at least one staple 460 against the anvil 124. In certain instances, the extension of the first sled portion 792 can completely lift, or completely deform, at least one staple 460 against the anvil 124. In various circumstances, the second sled portion 793 may not be advanced distally when the first sled portion 792 is moved into its extended position; however, in certain circumstances, at least some distal movement of the second sled portion 793 may occur when the first sled portion 792 is moved into its extended position.

Upon comparing FIGS. 71 and 72, it can be noted that the first sled portion 792 and the second sled portion 793 have been advanced distally to lift staples 460 toward the anvil 124. The first sled portion 792 and the second sled portion 793 can then be advanced to the distal end of the end effector 120 to complete the firing stroke of the end effector 120, which will be discussed in greater detail further below. In any event, the initial progression of the sled assembly 790 during the firing stroke of the end effector 120 is depicted in FIGS. 70-72. FIG. 70 depicts the sled assembly 790 in a retracted, unfired position; FIG. 71 depicts the sled assembly 790 in an extended, partially-fired position; and FIG. 72 depicts the sled assembly 790 in an extended, fired position. As outlined above, the pusher bar, or bars, 159 can be moved distally in order to advance the sled assembly 790 through the progression depicted in FIGS. 70-72. With reference to FIG. 70, a pusher bar 159 is illustrated in an initial, unfired position in which it is in contact with the proximal end of the first sled portion 792. In various embodiments, the pusher bar 159 can include a contact flange 155 extending from the distal end thereof which can engage the first sled portion 792. With further reference to FIG. 70, the pusher bar 159 may not be in contact with the second sled portion 793 when the pusher bar 159 is in its initial, unfired position. As the pusher bar 159 is advanced distally, the pusher bar 159 can move the first sled portion 792 distally until the contact flange 155 comes into contact with the proximal end of the second sled portion 793, as illustrated in FIG. 71. It is this relative motion between the first sled portion 792 and the second sled portion 793 which extends the sled assembly 790 as discussed above. Thereafter, the pusher bar 159 can be advanced distally in order to advance the first sled portion 792 and the second sled portion 793 distally at the same time, as illustrated in FIG. 72.

Figure 77:
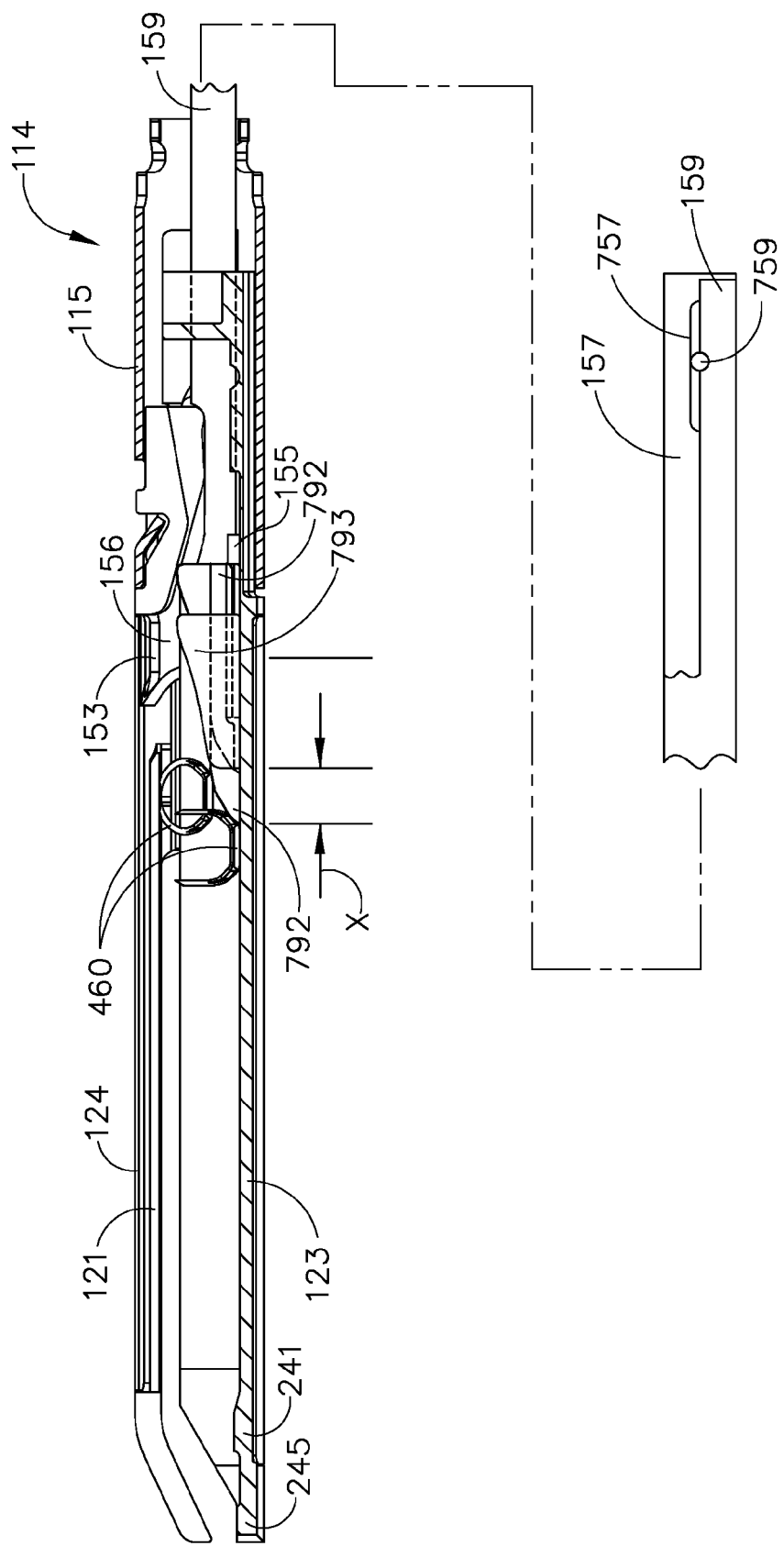
FIG. 77 is a cross-sectional view of the end effector of FIG. 65 illustrating the firing actuator in an extended condition and, in addition, a knife member in an unadvanced position.
Figure 78:
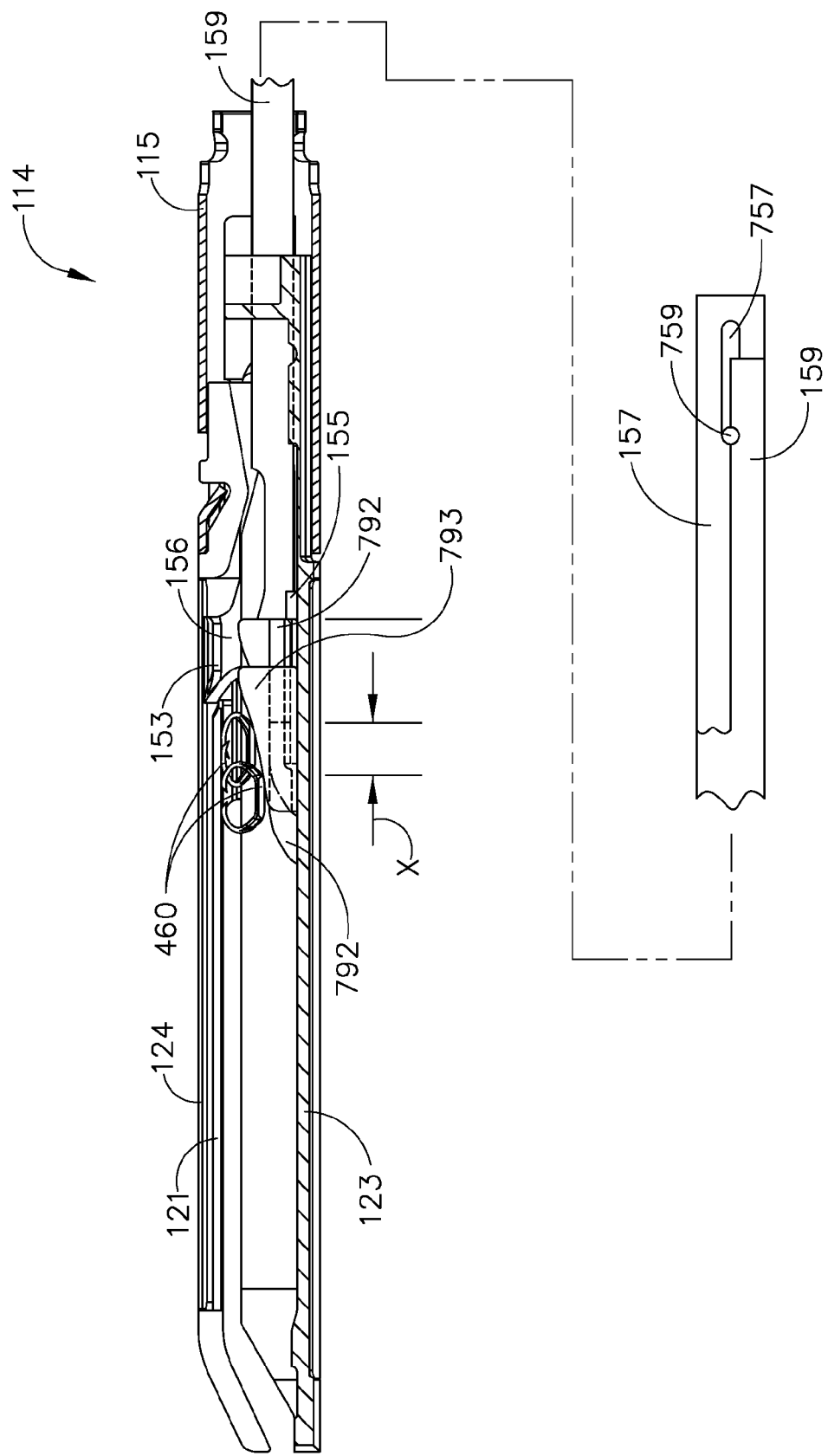
FIG. 78 is a cross-sectional view of the end effector of FIG. 65 illustrating the firing actuator in an advanced, extended condition and the knife member in an advanced position.
Figure 79:
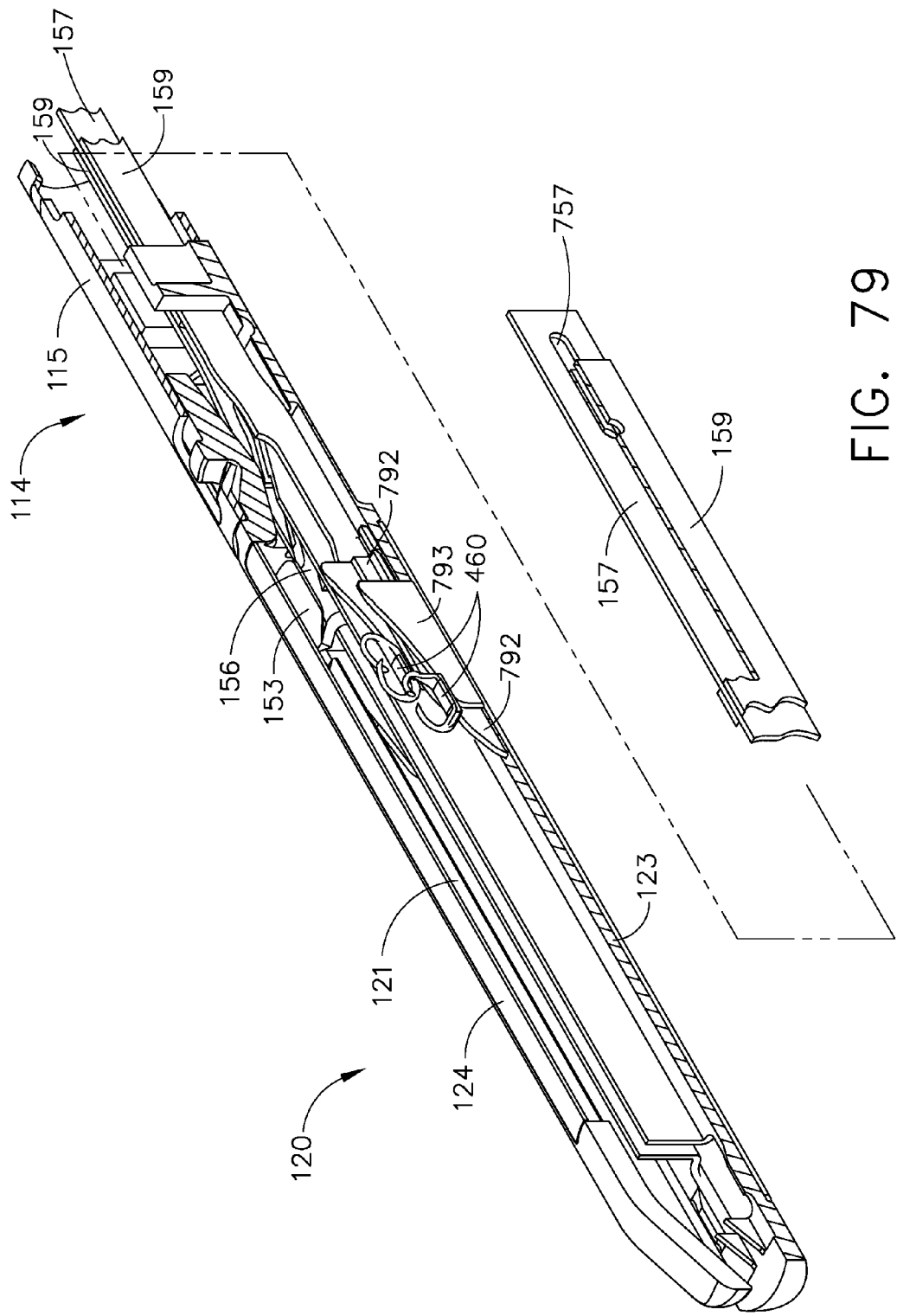
FIG. 79 is a cross-sectional perspective view of the end effector of FIG. 65 illustrated in the configuration depicted in FIG. 78.

As discussed above, the end effector 120 can be configured to staple and transect tissue at the same time. Referring again to FIG. 65, the end effector 120 can include a firing member, or knife bar, 156 comprising a knife edge 158 configured to transect the tissue as the knife bar 156 is advanced distally. Referring again to FIGS. 70 and 71, the initial distal movement of the pusher bar, or bars, 159 may not be transferred to the knife bar 156. Stated another way, the knife bar 156 may remain stationary, or at least substantially stationary, while the sled assembly 790 is moved between its retracted position (FIG. 70) and its extended position (FIG. 71). In such circumstances, relative movement between the pusher bars 159 and the knife bar 156 can occur, at least during the initial portion of the end effector firing stroke. Upon comparing FIGS. 74 and 77, it can be seen that, one, the pusher bars 159 have been advanced distally to extend the sled assembly 790 and, two, the knife bar 156 has not been advanced distally. Particular attention can be paid to the proximal ends of the knife bar 156 and the pusher bars 159. More particularly, the pusher bars 159 can include a drive pin 759 extending therebetween which extends through a drive slot 757 defined in the drive bar 157 extending proximally from the knife bar 156. When the pusher bars 159 are in their proximal unfired position, as illustrated in FIG. 74, the drive pin 759 is positioned in the proximal end of the drive slot 757. When the pusher bars 159 are advanced distally, as illustrated in FIG. 77, the drive pin 759 can slide distally within the drive slot 757 until the drive pin 759 reaches the distal end of the drive slot 757. In such a position, the sled 790 has been fully extended and the knife bar 156 has not yet been advanced distally with the pusher bars 159. Once the drive pin 759 is in contact with the distal end of the drive slot 757, as illustrated in FIGS. 78 and 79, the pusher bars 156 and the knife bar 159 can be advanced distally together.

Further to the above, the knife bar 156 can include flanges 153 and 155 which can be configured to engage the anvil 124 and the staple cartridge channel 123, respectively. When the knife bar 156 is in its proximal, unadvanced position, as illustrated in FIG. 77, the flange 153 can be positioned proximally with respect to a slot 121 defined in the anvil 124. In such a position of the knife bar 156, the flange 155 may or may not be positioned within a slot defined within and/or in the exterior of the cartridge channel 123. As the knife bar 156 is advanced distally, the flange 153 can enter into the anvil slot 121 and the flange 155 can be positioned within the cartridge channel slot. In such circumstances, the knife bar 156 can set the gap, or tissue gap distance, between the anvil 124 and the staple cartridge positioned within the cartridge channel 123. In various circumstances, the knife bar 156 can control the forming height and/or the compression of the tissue within the end effector 120 as the knife bar 156 is advanced distally.

The arrangement described above in which the pusher bars 159 move the sled assembly 790 before the pusher bars 159 advance the knife 158 can be advantageous in many circumstances. For instance, it is often desirable to staple tissue before it is incised and, thus, the formation of the staples leads, or at least sufficiently leads, the transection of the tissue by the knife bar 156. The staggered deployment of the sled 790 and the knife bar 156 can facilitate such a relative progression between the staple formation and the tissue incision. Moreover, the sled 790 can be compactly stored in the end effector 120 in its retracted, unfired configuration in order to permit a shorter proximal-to-distal, or longitudinal, length of the end effector 120. Stated another way, less longitudinal room may be required for a sled assembly that can begin its firing stroke in at least partially collapsed state. Furthermore, owing to the longitudinal extendibility of the sled assembly 790, the staple lifting surfaces of the sled assembly 790 can be longer and can include a shallower, or less aggressive, ramp angle than a unitary sled, for instance. Stated another way, the mechanical advantage of the sled assembly 790 can be improved owing to longer longitudinal lengths available for the ramps of the sled assembly 790.

Figure 82:
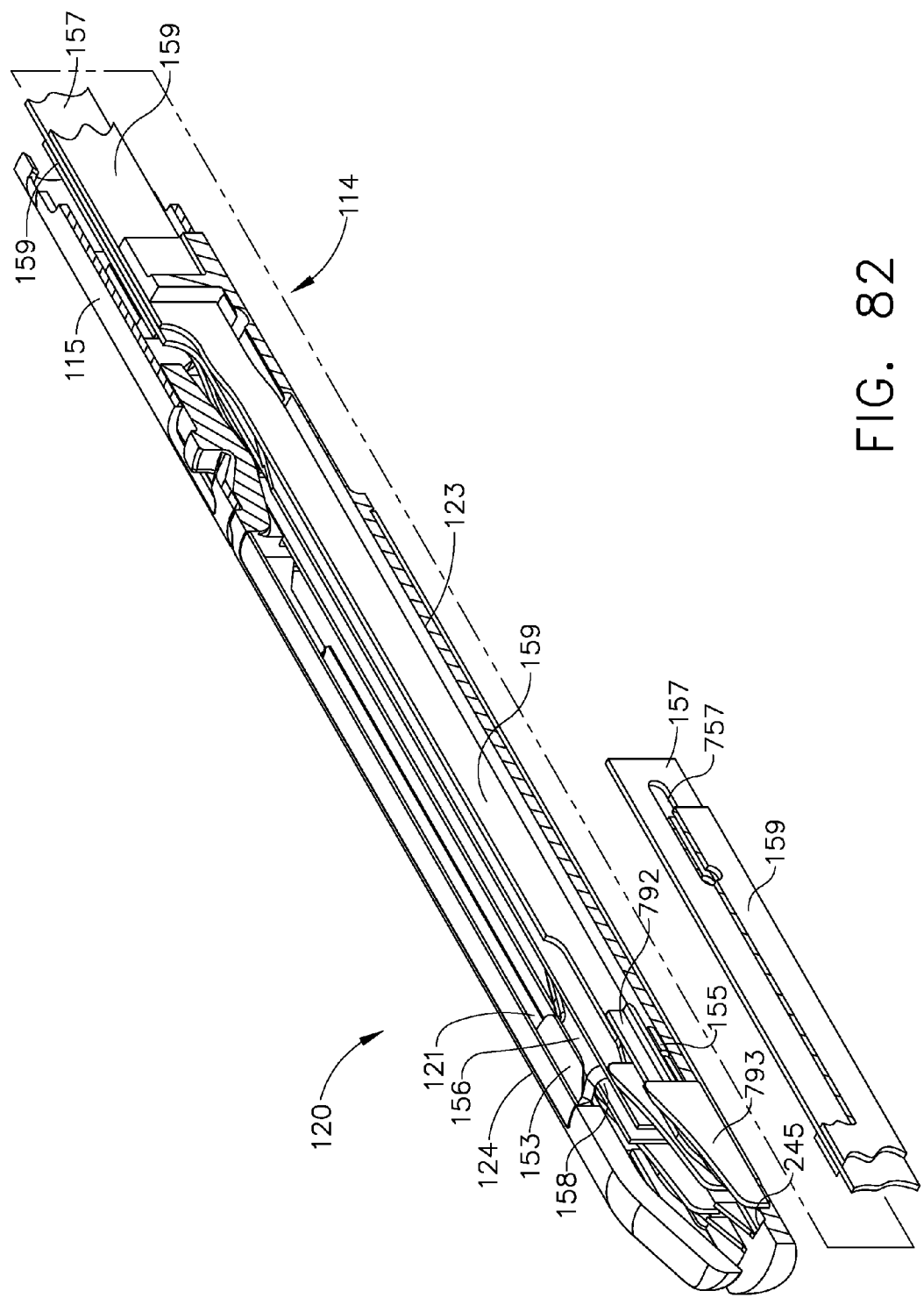
FIG. 82 is a cross-sectional perspective view of the end effector of FIG. 65 illustrated in the configuration depicted in FIG. 80.

Turning now to FIGS. 80-82, the sled assembly 790 and the knife bar 156 can be advanced distally toward the distal end of the end effector 120 to complete the firing stroke of the end effector 120. As the sled 790 approaches the distal end of the end effector 120, in various instances, the first sled portion 792 can contact a distal end 245 of the staple cartridge and retract relative to and/or within the second sled portion 793. More particularly, the distal end 245 can block the distal movement of the first sled portion 792 while the second sled portion 793 is advanced distally relative to the first sled portion 792 in order to complete the firing stroke. In various instances, the second sled portion 793 can be advanced distally until it also contacts the distal end 245 of the staple cartridge while, in other instances, the firing stroke can be completed before the second sled portion 793 contacts the distal end 245. In either event, in embodiments where the distal flanges 155 of the pusher bars 159 push the first sled portion 792 and the second sled portion 793 toward the distal end of the end effector 120, the first sled portion 792 may become disengaged from the pusher bars 159 when the first sled portion 792 reaches the distal end so that that the pusher bars 159 can push the second sled portion 793 relative to the first sled portion 792. In at least one such instance, referring primarily to FIG. 77, the distal end of the staple cartridge can include a boss 241 which can be configured to lift the first sled portion 792 upwardly toward the anvil 124 so that the pusher bars 159 can slide underneath the first sled portion 792. In such circumstances, the first sled portion 792 can be operatively disengaged from the second sled portion 793 and the pusher bars 159. In various instances, the boss 241 can be positioned and arranged such that the first sled portion 792 is lifted upwardly after all of the staples of the staple cartridge have been deployed and/or transferred to the second sled portion 793, as discussed above. Moreover, further to the above, the distal end of the staple cartridge can include a first boss 241 configured to lift a first sled portion 792 and a second boss 241 configured to lift an additional first sled portion 792. In various instances, the bosses 241 can be configured to synchronously lift the first sled portions 792 at the same time. In some instances, the bosses 241 can be configured to lift the first sled portions 792 sequentially.

Figure 86:
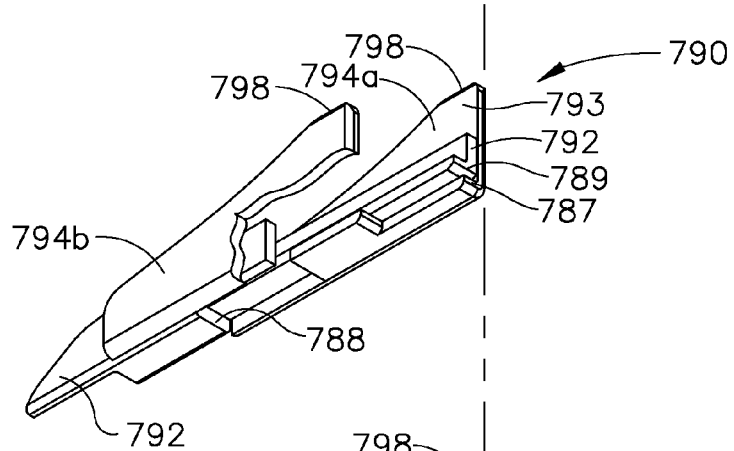
FIG. 86 is a perspective view of the firing member of the end effector of FIG. 65 illustrated in the extended configuration depicted in FIG. 77.
Figure 87:
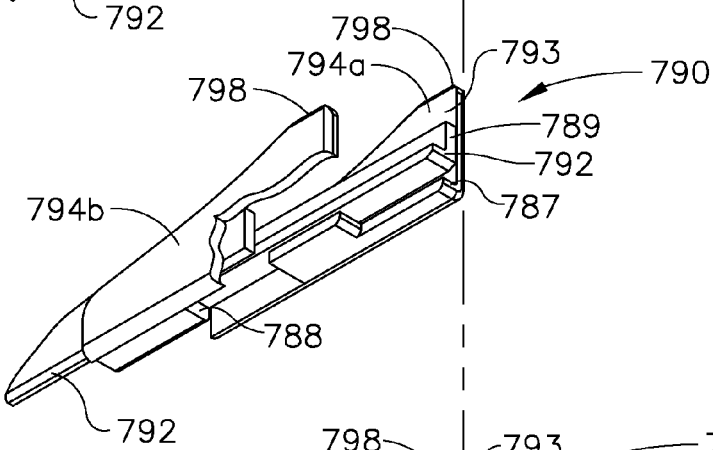
FIG. 87 is a perspective view of the firing member of the end effector of FIG. 65 illustrated in a configuration just prior to the fully-fired configuration depicted in FIG. 80.
Figure 88:
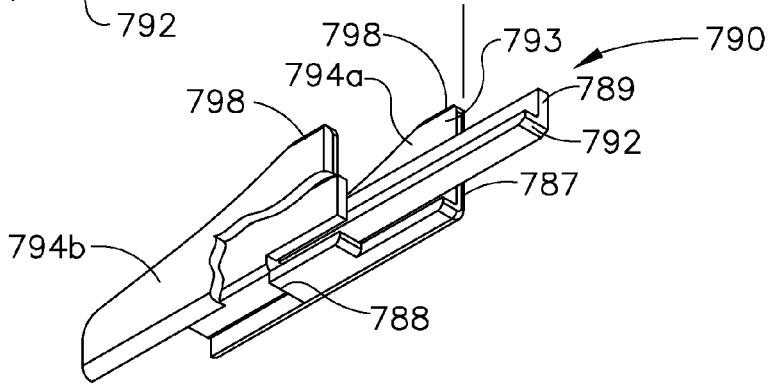
FIG. 88 is a perspective view of the firing member of the end effector of FIG. 65 illustrated in the fully-fired configuration depicted in FIG. 80.
Figure 91:
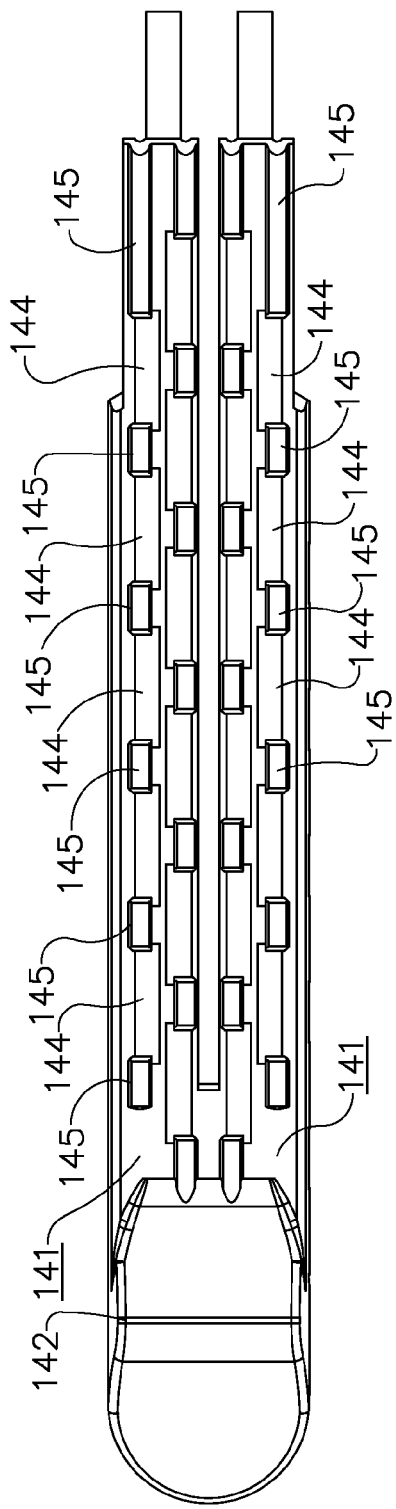
FIG. 91 is a plan view of a staple cartridge body of the end effector of FIG. 89.

Referring now to FIGS. 85-88, FIG. 85 depicts the sled assembly 790 in its initial, unfired configuration. Further to the above, a pusher bar 159 can contact a proximal end 789 of the first sled portion 792 and push the first sled portion 792 distally until the proximal end 789 of the first sled portion 792 is flush with a proximal end 787 of the second sled portion 793, as illustrated in FIG. 86. At such point, the first sled portion 792 can be fully extended relative to the second sled portion 793. Thereafter, the pusher bar 156 can push on the proximal end 787 and the proximal end 789 simultaneously to advance the sled assembly 790 distally. As also discussed above, referring now to FIG. 87, the first sled portion 792 can be stopped by the distal end 245 of the staple cartridge and lifted upwardly by the boss 241 of the staple cartridge, for instance. At such point, the first sled portion 792 can be elevated relative to the second sled portion 793, and the distal flange 155, such that the second sled portion 793 can be slid relative to, and at least partially underneath, the first sled portion 792, in order to collapse the sled assembly 790, as illustrated in FIG. 88. Upon comparing FIGS. 87 and 88, it can be seen that the second sled portion 793 is moved closer toward ledge 788 defined in the bottom surface of the first sled portion 792 and that the distal end 789 of the first sled portion 792 is no longer aligned with the distal end 787 of the second sled portion 793.

Figure 83:
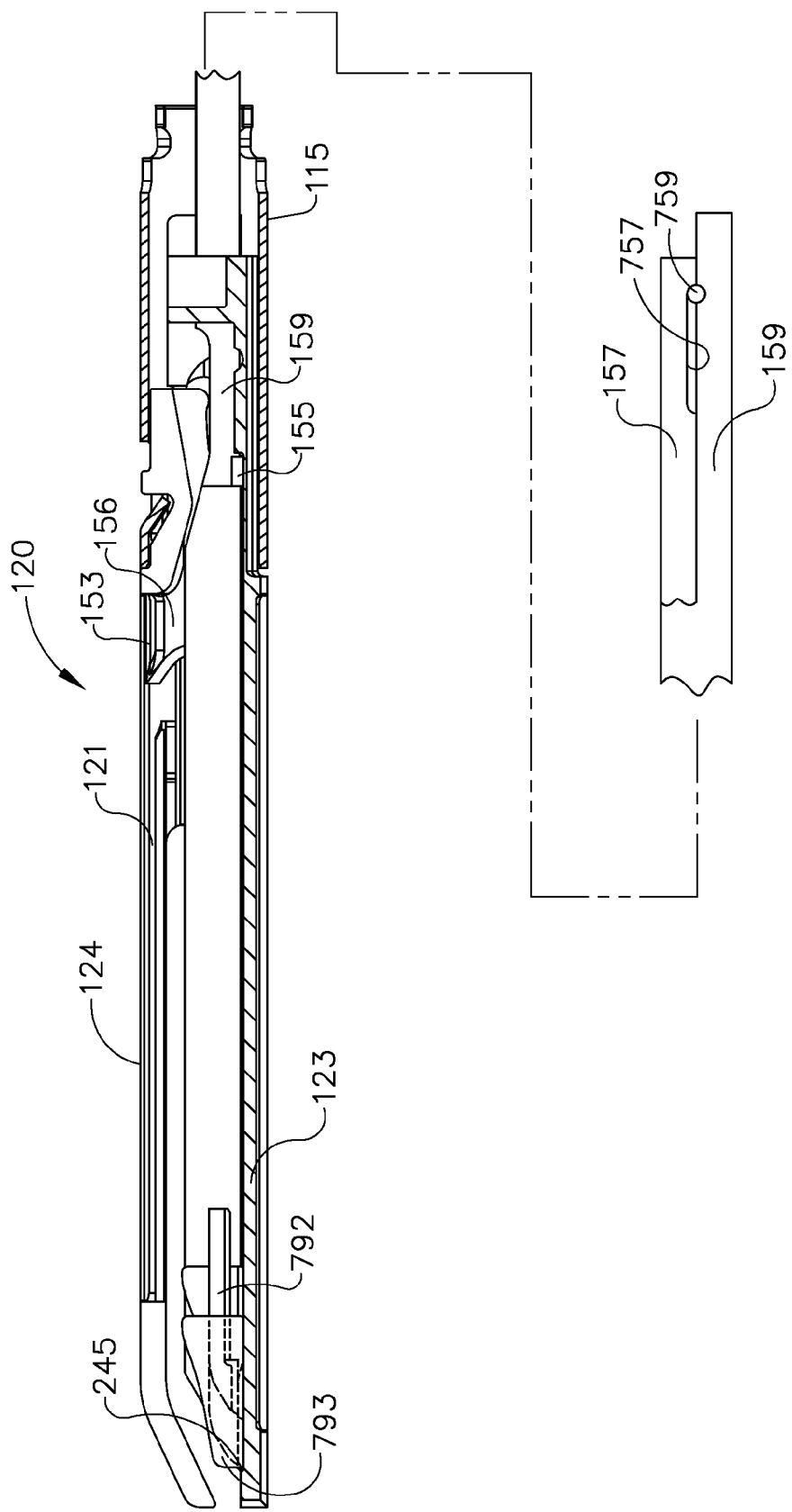
FIG. 83 is a cross-sectional elevational view of the end effector of FIG. 65 illustrating the knife member in a retracted position.
Figure 84:
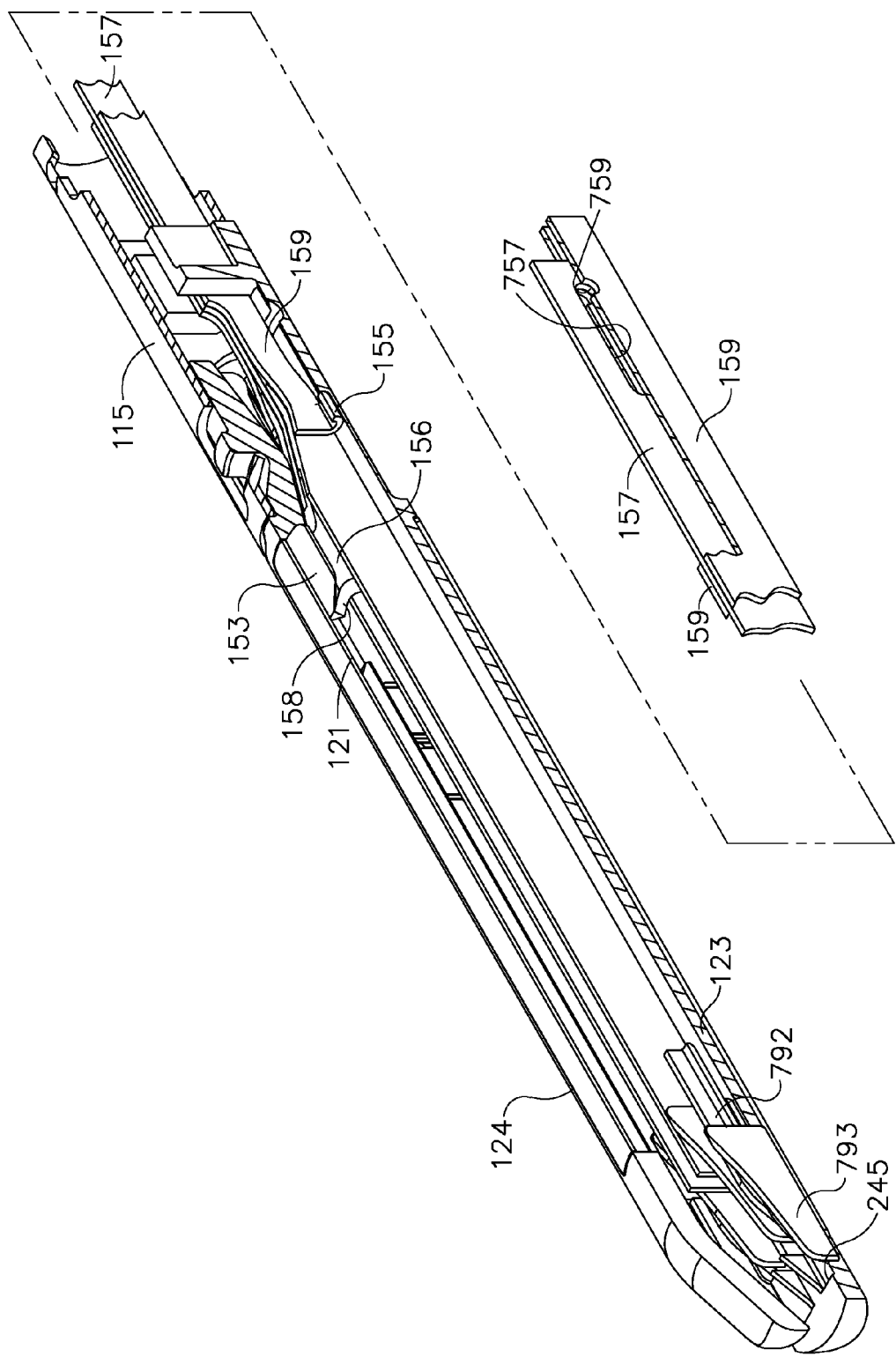
FIG. 84 is a cross-sectional perspective view of the end effector of FIG. 65 illustrated in the configuration depicted in FIG. 83.
Figure 85:
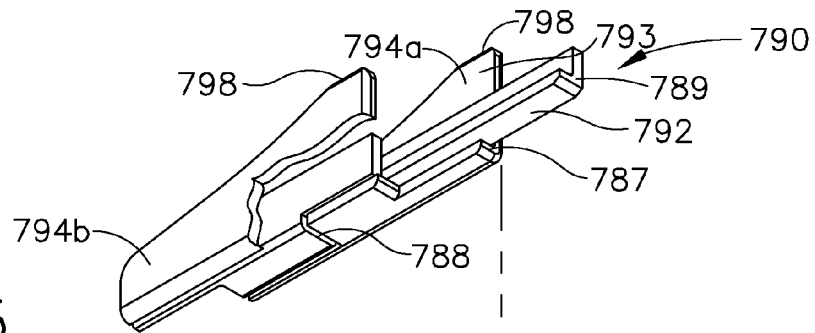
FIG. 85 is a perspective view of the firing member of the end effector of FIG. 65 illustrated in the unextended configuration depicted in FIG. 74.

After the firing stroke has been completed, referring now to FIGS. 83 and 84, the knife bar 156 and the pusher bars 159 can be retracted proximally. In various circumstances, the knife bar 156 can be pulled proximally by the pusher bars 159. More particularly, the pusher bars 159 can be retracted proximally relative to the knife bar 159 until the drive pin 759 contacts the proximal end of the drive slot 759. At such point, the pusher bars 159 can pull the knife bar 156 proximally until the flange 153 of the knife bar 156 is no longer positioned within the slot 121 of the anvil 124. Thereafter, the anvil 124 can be moved into its open position when the closure tube 115 is pulled proximally. In certain instances, the staple cartridge can comprise a replaceable staple cartridge. In such instances, the spent staple cartridge can be removed from the cartridge channel 122 and, if desired, an unspent staple cartridge can be positioned within the cartridge channel 122 so that the surgical instrument can be used once again.

As illustrated in FIGS. 83 and 84, the collapsed sled assembly 790 can be left behind in the distal end of the end effector 120 when the knife bar 156 and the pusher bars 159 are retracted. In the event that the spent staple cartridge is removed from the cartridge channel 122, the collapsed sled assembly 790 can be removed from the end effector 120 with the cartridge. In certain instances, a staple cartridge may not be completely spent before the pusher bars 159 and the knife bar 156 are retracted. In such instances, the sled assembly 790 may only be partially advanced within the staple cartridge and may not be collapsed back into its unextended configuration. When the staple cartridge is then removed from the cartridge channel 123, some of the staples may still be positioned within their staple cavities.

As discussed herein, a firing actuator, or sled, of a staple cartridge and/or stapling instrument can include one or more inclined ramp surfaces configured to lift, or deploy, staples between an unfired position and a fired position. For instance, a sled can include a first inclined ramp surface configured to deploy a first row of staples, a second inclined ramp surface configured to deploy a second row of staples, and so forth. Each inclined ramp surface can comprise a contiguous surface which is configured to engage each staple in the corresponding row of staples and lift the staples until they have been fully deformed against an anvil positioned opposite the staple cartridge. The contiguous surface which defines each inclined ramp surface can include any suitable number of contours such as, for instance, one or more linear surfaces and/or one or more curved surfaces. In various instances, the contiguous surface can directly engage each staple in the corresponding row of staples and can remain continuously engaged with a staple in that row as it moved from its unfired position to its fully-fired position. After a staple has reached its fully-fired position, the inclined ramp surface may become disengaged from that staple. This arrangement can be possible for sleds with relatively movable components, such as sled assembly 790, for instance, and/or sleds that are not comprised of relatively movable components, such as sleds comprised of a unitary piece of material, for example.

Figure 92:
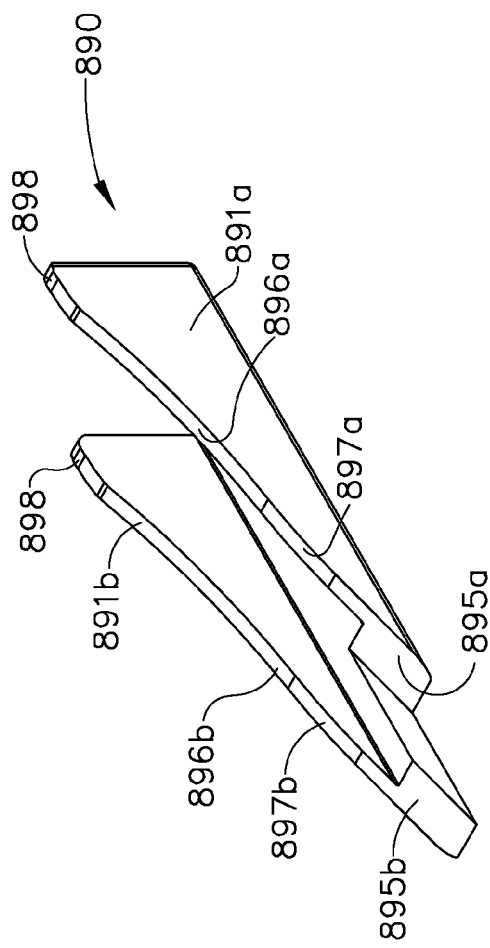
FIG. 92 is a perspective view of a firing actuator for use with the cartridge body of FIG. 91.

In various circumstances, a firing actuator, or sled, can comprise one or more inclined ramp surfaces, wherein each inclined ramped surface is comprised of two or more co-operating drive surfaces. For instance, turning now to FIG. 92, a sled 890 can include a first inclined ramp surface 891a which is comprised of an initial, or first, drive surface 895a and a second, or final, drive surface 896a. The initial drive surface 895a and the final drive surface 896a of the first inclined ramp surface 891a can be configured to co-operatively lift the staples in a first staple row between an unfired position and a fired position. As the sled 890 is moved distally through a staple cartridge, referring to FIGS. 89-92, the initial drive surface 895a can contact a staple 160, for instance, and lift the staple 160 from its unfired position (FIG. 89) to a partially-fired position (FIG. 90). Thereafter, the sled 890 can be advanced distally such that the final drive surface 896a can lift the staple 160 between its partially-fired position and its fully-fired position. In various instances, the initial drive surface 895a can contact the initial drive surfaces 180 of the staples 160 to lift the staples 160 into their partially-fired positions and the final drive surface 896a can contact the second drive surfaces 182 of the staples 160 to lift the staples 160 into their finally-fired positions. In such instances, the staples 160 can be transferred from the initial drive surface 895a to the final drive surface 896a to complete the deployment, or firing, thereof. Referring to FIG. 92, the deployment, or firing, of a staple 160 can be complete once the apex 898 of the first inclined ramp surface 891a has passed under the second drive surface 182 of the staple 160.

Further to the above, referring again to FIG. 92, the initial drive surface 895a and the final drive surface 896a of the first inclined ramp surface 891a can be configured to co-operatively deploy staples within a first row of staples. The sled 890 can include additional inclined ramp surfaces to deploy additional rows of staples. For instance, the sled 890 can include a second inclined ramp surface 891b comprising an initial drive surface 895b and a final drive surface 896b which can be configured to co-operatively deploy staples within a second row of staples. In various instances, the sled 890 can further include any suitable number of inclined ramp surfaces, such as a third inclined ramp surface, similar to first inclined ramp surface 891a, configured to deploy staples within a third row of staples and a fourth inclined ramp surface, similar to second inclined ramp surface 891b, configured to deploy staples within a fourth row of staples, for example. In any event, the drive surfaces of an inclined drive surface, such as drive surfaces 895a, 895b, 896a, and 896b, for example, can include any suitable configuration such as a linear profile and/or a curved profile, for example. With further reference to FIG. 92, the first inclined ramp surface 891a can include a transition drive surface 897a intermediate the initial drive surface 895a and the final drive surface 896a. Similarly, the second inclined ramp surface 891b can include a transition drive surface 897b intermediate the initial drive surface 895b and the final drive surface 896b. In various instances, a transition drive surface can comprise a transition between one drive surface and another drive surface. In some instances, a transition drive surface can comprise a surface which simultaneously drives the initial drive surface 180 and the second drive surface 182 of a staple 160, for example. In various instances, an inclined ramp surface can include any suitable number of drive surfaces.

In various instances, further to the above, the initial drive surface 895a can be positioned laterally with respect to the final drive surface 896a. In certain instances, the initial drive surface 895a and the final drive surface 896a can be connected to one another. In other instances, the initial drive surface 895a and the final drive surface 896a may not be connected to one another. In various circumstances, the initial drive surface 895a can be defined by a first height and the final drive surface 896a can be defined by a second height which is taller than the first height. In certain circumstances, the initial drive surface 895a can be defined along a first longitudinal axis and the final drive surface 896a can be defined along a second longitudinal axis. In certain instances, the first longitudinal axis and the second longitudinal axis can be parallel. In some instances, the initial drive surface 895a can be defined by a first plane and the final drive surface 896a can be defined by a second plane which is parallel to the first plane. In other instances, the first longitudinal axis and the second longitudinal axis can be non-parallel. In some instances, the first longitudinal axis and the second longitudinal axis can extend in directions which converge. In other instances, the first longitudinal axis and the second longitudinal axis can extend in directions which do not converge. In various instances, further to the above, the transition drive surface 897a of the first inclined surface 891a can be defined along an axis which is parallel to the first longitudinal axis and/or the second longitudinal axis. In certain instances, the transition drive surface 897a can be defined along an axis which is not parallel to the first longitudinal axis and/or the second longitudinal axis. In various instances, further to the above, the transition drive surface 897a of the first inclined surface 891a can be defined within a plane which is parallel to the first plane and/or the second plane. In some instances, the transition drive surface 897a can be co-planar with the initial drive surface 895a and/or the final drive surface 896a. In certain instances, the transition drive surface 897a can be defined within a plane which is different than the first plane and/or the second plane. In various instances, further to the above, the transition drive surface 897a can connect the initial drive surface 895a to the final drive surface 896a.

The discussion provided above in connection with inclined ramp surface 891a, initial drive surface 895a, final drive surface 896a, and transition drive surface 897a can be equally applicable to inclined ramp surface 891b, initial drive surface 895b, final drive surface 896b, and transition drive surface 897b, for example.

In various circumstances, further to the above, the first inclined ramp surface 891a can be parallel to the second inclined ramp surface 891b. In other instances, the first inclined ramp surface 891a may not be parallel to the second inclined ramp surface 891b. In various instances, the first inclined ramp surface 891a can be defined by a first height and the second inclined ramp surface 891b can be defined by a second height. In some instances, the first height can be the same as the second height. In such instances, a first row of staples formed by the first inclined ramp surface 891a and a second row of staples formed by the second inclined ramp surface 891b can be formed to the same height. In other instances, the first height can be different that the second height. In such instances, a first row of staples formed by the first inclined ramp surface 891a and a second row of staples formed by the second inclined ramp surface 891b can be formed to different heights. The disclosure of U.S. Pat. No. 8,317,070, entitled SURGICAL STAPLING DEVICES THAT PRODUCE FORMED STAPLES HAVING DIFFERENT LENGTHS, which issued on Nov. 27, 2012, is incorporated by reference in its entirety.

As discussed above, a sled can directly drive and deploy a staple and/or any other suitable fastener stored within a cartridge. Stated another way, the sled can directly contact the staples wherein a driver is not present intermediate the sled and the staples. Such an arrangement is different than arrangements which include a plurality of drivers which support the staples. In such arrangements, the sled engages the drivers to lift the staples. In these arrangements, the drivers are often configured to completely eject the staples from the staple cavities in which they are stored. More particularly, the drivers are configured to lift the staples such that the staples are completely positioned above the top surface, or deck, of the staple cartridge when the staples are in their fully-fired position. In order to completely lift the staples above the deck of the staple cartridge, the drivers may also be at least partially lifted above the deck. Such an arrangement can be characterized as overdriving the staples. Many of the teachings discussed herein can be applied to embodiments including one or more sleds which directly drive staples and, in addition, embodiments including a plurality of drivers which are driven by one or more sleds in order to drive the staples. For instance, sled 890 is discussed in connection with embodiments in which it directly drives staples 160; however, sled 890 could also be used in embodiments which include drivers configured to deploy staples from the staple cavities. In such embodiments, each driver could include a first drive surface similar to first drive surface 180 configured to be engaged by the initial drive surface 895a, for instance, and a second drive surface similar to second drive surface 182 configured to be engaged by the final drive surface 896a, for instance.

In the embodiments disclosed herein in which the staples are driven directly by the sled, i.e., without the use of drivers, further to the above, the staples can be completely lifted above the deck, or overdriven, by the sled itself. Turning now to FIGS. 91-94, the sled 890 is configured to partially extend above the deck surface 141 of the cartridge 142. More particularly, the apex 898 of the first inclined ramp surface 891a and the apex 898 of the second inclined ramp surface 891b can extend above the deck surface 141 as the inclined ramp surfaces 891a and 891b pass through and/or between the cavities 144 to eject the staples 160, for example, from the staple cavities 144. In such circumstances, the sled 890 is configured to partially extend above the staple cavity openings defined in the deck surface 141. In various instances, the cartridge 142 can further comprise a plurality of coverings 145 positioned within and/or aligned with the rows of staple cavities 144. For instance, a covering 145 can be positioned intermediate adjacent staple cavities 144 within a staple cavity row. In certain instances, a covering 145 can be positioned proximally and/or distally with respect to a staple cavity 144. In various instances, referring primarily to FIG. 94, the apexes 898 of the inclined ramp surfaces 891 can pass underneath the coverings 145. In such instances, each covering 145 can include a bottom surface, such as an arched bottom surface 147, for example, configured to permit the inclined ramp surfaces 891 to pass thereunder. With further reference to FIG. 94, the cartridge 142 can include a first longitudinal slot 149 configured to slidably receive the first inclined ramp surface 891a therein and a second longitudinal slot 149 configured to receive the second inclined ramp surface 891b, for example. In various instances, the cartridge 142 can include a plurality of longitudinal slots 149 configured to receive the inclined ramp surfaces of the sled 890. In certain instances, the longitudinal slots 149 can be defined by the coverings 145 and the staple cavities 144. In some circumstances, each longitudinal slot 149 can correspond to a longitudinal row of staple cavities 144 wherein a longitudinal slot 149 can place the staple cavities 144 within a staple cavity row in communication with each other such that an inclined ramp surface passing through the longitudinal slot 149 can pass through the staple cavities 144 as outlined above.

In various instances, the deck of a cartridge can be configured to directly contact the tissue being fastened and/or support the tissue being fastened. In certain circumstances, a cartridge assembly can include a layer positioned on the deck, such as a tissue thickness compensator, for example, which is disclosed in U.S. patent application Ser. No. 12/894,369, entitled IMPLANTABLE FASTENER CARTRIDGE COMPRISING A SUPPORT RETAINER, now U.S. Patent Application Publication No. 2012/0080344, which was filed on Sep. 30, 2010, U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336, which was filed on Apr. 29, 2011, and U.S. patent application Ser. No. 13/242,066, entitled CURVED END EFFECTOR FOR A STAPLING INSTRUMENT, now U.S. Patent Application Publication No. 2012/0080498, which was filed on Sep. 23, 2011. The entire disclosures of U.S. patent application Ser. No. 12/894,369, entitled IMPLANTABLE FASTENER CARTRIDGE COMPRISING A SUPPORT RETAINER, now U.S. Patent Application Publication No. 2012/0080344, which was filed on Sep. 30, 2010, U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336, which was filed on Apr. 29, 2011, and U.S. patent application Ser. No. 13/242,066, entitled CURVED END EFFECTOR FOR A STAPLING INSTRUMENT, now U.S. Patent Application Publication No. 2012/0080498, which was filed on Sep. 23, 2011, are incorporated herein by reference. In various instances, referring again to FIG. 93, the deck 141 and the coverings 145 can be configured to directly contact tissue. In such instances, coverings 145 can extend above the deck 141 and, as a result, the deck 141 and the coverings 145 can comprise an uneven support surface. The coverings 145, in various instances, can apply an additional compressive pressure to the tissue positioned directly above and/or adjacent to each longitudinal row of staples. This additional compressive pressure can push fluids present within the tissue away from the staple lines prior to, during, and/or after the staple forming process which, as a result, can promote better staple formation and/or staple retention within the tissue. The coverings 145 can also be configured to grip the tissue positioned between a staple cartridge and an anvil, especially along the staple lines where the staple formation occurs. The coverings can also be configured to support the staples as the staples are being ejected from the staple pockets to provide a localized control over the staple forming process. The entire disclosures of U.S. patent application Ser. No. 12/893,461, entitled STAPLE CARTRIDGE, now U.S. Pat. No. 8,733,613, which issued on May 27, 2014, and U.S. patent application Ser. No. 13/851,676, entitled TISSUE THICKNESS COMPENSATOR COMPRISING A CUTTING MEMBER PATH, now U.S. Patent Application Publication No. 2014/0291379, which was filed on Mar. 27, 2013, are incorporated by reference herein.

As discussed above, referring primarily to FIGS. 58, 61, and 64, a staple cavity, such as staple cavity 144, for example, can include a first sidewall 150a and a second sidewall 150b which can be configured to guide a staple, such as a staple 160, for example, as it is lifted between an unfired position and a fired position. In various instances, the sidewalls 150a, 150b can be configured and arranged such that the entirety of the staple 160 is positioned intermediate the sidewalls 150a, 150b when the staple 160 is in its unfired position. In other circumstances, referring primarily to FIGS. 22-31, the sidewalls 150 of the staple cavity 144 may be configured such that less than the entirety of the staple 160 is positioned intermediate the sidewalls 150 when the staple 160 is in its unfired position. For instance, the base 162 of the staples 160 in the outermost rows of staple cavities 144 defined in the cartridge body 142 may be unsupported by at least one of the sidewalls 150 when the staples 160 are in their unfired positions. As the staples 160 are lifted upwardly, however, the bases 162 of the staples 160 may then be supported by both of the sidewalls 150. Turning now to FIGS. 93 and 94, some of the staple cavities 144 of the cartridge 142, such as cavities 144a, for example, may only support both sides of the bases 162 at the end of their lifting motion. In any event, even though the sidewalls of the staple cavities 144 defined in the cartridge body 142 may not entirely support the staples 160 in their unfired positions, the cartridge channel 123 of jaw 122, referring again to FIGS. 3 and 65, may at least partially support the staples 160. Stated another way, the cartridge body 142 and the cartridge channel 123 may co-operate to define the staple cavities 144 in order to support and/or surround the staples 160 throughout the lifting motion of the staples 160. For instance, the cartridge body 142 and the cartridge channel 123 can co-operate to support and/or surround a staple 160 when the staple 160 is in its unlifted position. At some point during the lifting motion of the staple 160, in some circumstances, the cartridge channel 123 may no longer support and/or the staple 160 and, in such circumstances, the cartridge body 142 may entirely support the staple 160 for the remainder of the lifting motion. In at least one embodiment, the cartridge channel 123 and the cartridge body 142 may co-operate to support the staple 160 for half, or approximately half, of the lifting motion. In other embodiments, the cartridge channel 123 and the cartridge body 142 may co-operate to support the staple 160 for less than half or more than half of the lifting motion. In some instances, the cartridge body 142 and the cartridge channel 123 may co-operatively support and/or surround the staple 160 throughout the entire lifting motion of the staple 160.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Pat. No. 8,561,870, which issued on Oct. 22, 2013, which is hereby incorporated by reference in its entirety. Additionally, U.S. patent application Ser. No. 12/893,461, filed Sep. 29, 2012, entitled STAPLE CARTRIDGE, now U.S. Pat. No. 8,733,613, which issued on May 27, 2014, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. The entire disclosure of U.S. Pat. No. 7,845,537, entitled SURGICAL INSTRUMENT HAVING RECORDING CAPABILITIES, which issued on Dec. 7, 2010 is incorporated by reference herein. The entire disclosure of U.S. application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, which issued on Jul. 7, 2015, is incorporated by reference herein.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical system, comprising:
a sled comprising a driving surface, wherein the sled is configured to move along a longitudinal axis during a firing motion; and
a staple, comprising:
a first leg;
a second leg; and
a non-linear base, comprising:
a first end portion, wherein the first leg extends from the first end portion;
a second end portion, wherein the second leg extends from the second end portion;
a first drive surface;
a second drive surface laterally offset from the first drive surface, wherein the second drive surface is longitudinally offset from the first end portion and the second end portion, and wherein the second drive surface comprises a ramp, wherein the driving surface of the sled is configured to drivingly engage the ramp during the firing motion to move the staple in a direction orthogonal to the longitudinal axis; and a contour intermediate the first drive surface and the second drive surface.

2. The surgical system of claim 1, wherein the first drive surface is coplanar with the first leg and the second leg.

3. The surgical system of claim 1, wherein the second drive surface is laterally offset from the first leg and the second leg.

4. The surgical system of claim 1, wherein the second drive surface further comprises a flat surface.

5. The surgical system of claim 1, wherein the non-linear base further comprises a proximal portion, wherein the first leg extends from the proximal portion, and wherein the proximal portion further comprises the first drive surface.

6. The surgical system of claim 5, wherein the proximal portion further comprises a nub.

7. The surgical system of claim 1, wherein the base, the first leg, and the second leg define a unitary piece.

8. A surgical system, comprising:
a sled comprising a driving surface, wherein the sled is configured to move along a longitudinal axis during a firing motion; and
a staple, comprising:
a base comprising an integral drive surface, wherein the integral drive surface comprises an inclined surface, and wherein the driving surface of the sled is configured to drivingly engage the inclined surface during the firing motion to move the staple in a direction orthogonal to the longitudinal axis;
a first leg extending from the base; and
a second leg extending from the base;
wherein a staple midline bisects the base intermediate the first leg and the second leg, wherein the inclined surface of the integral drive surface extends across the staple midline, and wherein the integral drive surface is laterally offset from the first leg and the second leg.

9. The surgical system of claim 8, wherein the first leg and the second leg flank the integral drive surface.

10. The surgical system of claim 8, wherein the integral drive surface comprises a first integral drive surface, and wherein the base further comprises a second integral drive surface.

11. The surgical system of claim 10, wherein the second integral drive surface is laterally aligned with the first leg and the second leg.

12. The surgical system of claim 10, wherein the second integral drive surface is proximal to the integral drive surface.

13. The surgical system of claim 10, wherein a gap is defined between the second integral drive surface and the integral drive surface.

* * * * *